US009840486B2

(12) United States Patent
Hucul et al.

(10) Patent No.: US 9,840,486 B2
(45) Date of Patent: Dec. 12, 2017

(54) METHODS OF PRODUCING ALKYLFURANS

(71) Applicant: MICROMIDAS, INC., West Sacramento, CA (US)

(72) Inventors: Dennis A. Hucul, Midland, MI (US); Dimitri A. Hirsch-Weil, Sacramento, CA (US); Makoto Nathanael Masuno, Elk Grove, CA (US); John Albert Bissell, II, Sacramento, CA (US); Alex B. Wood, Sacramento, CA (US); Robert Joseph Araiza, Sacramento, CA (US); Daniel R. Henton, Midland, MI (US); Shawn M. Browning, Sacramento, CA (US); Ryan L. Smith, Sacramento, CA (US)

(73) Assignee: Micromidas, Inc., West Sacramento, CA (US)

( * ) Notice: Subject to any disclaimer, the term of this patent is extended or adjusted under 35 U.S.C. 154(b) by 0 days.

(21) Appl. No.: 15/503,681

(22) PCT Filed: Aug. 14, 2015

(86) PCT No.: PCT/US2015/045330
§ 371 (c)(1),
(2) Date: Feb. 13, 2017

(87) PCT Pub. No.: WO2016/025865
PCT Pub. Date: Feb. 18, 2016

(65) Prior Publication Data
US 2017/0267654 A1 Sep. 21, 2017

Related U.S. Application Data

(60) Provisional application No. 62/037,806, filed on Aug. 15, 2014.

(51) Int. Cl.
*C07D 307/36* (2006.01)
*C07C 2/86* (2006.01)

(52) U.S. Cl.
CPC ............ *C07D 307/36* (2013.01); *C07C 2/865* (2013.01)

(58) Field of Classification Search
CPC .................................................. C07D 307/36
USPC ........................................................ 549/506
See application file for complete search history.

(56) References Cited

U.S. PATENT DOCUMENTS

| 4,335,049 A | 6/1982 | Hamada et al. |
| 2011/0263880 A1 | 10/2011 | Rauchfuss et al. |
| 2014/0171699 A1 | 6/2014 | Wang et al. |
| 2016/0200700 A1 | 7/2016 | Hirsch-Weil et al. |

FOREIGN PATENT DOCUMENTS

| CN | 101434588 B | 8/2011 |
| EP | 2666540 A1 | 11/2013 |
| JP | 58-13576 A | 1/1983 |
| JP | 61-59633 B2 | 12/1986 |
| WO | 2015/023918 A2 | 2/2015 |
| WO | 2015/031753 A1 | 3/2015 |
| WO | 2016/025865 A1 | 2/2016 |

OTHER PUBLICATIONS

Albers et al., "Poisoning and Deactivation of Palladium Catalysts", Journal of Molecular Catalysis A: Chemical, vol. 17.3, 2001, pp. 275-286.
Binder et al "Simple Chemical Transformation of Lignocellulosic Biomass into Furans for Fuels and Chemicals", Journal American Chemical Society, vol. 131, No. 5, 2009, pp. 1979-1985.
Boudart, M., "Turnover Rates in Heterogeneous Catalysis", Chemical Reviews, vol. 95, No. 3, 1995, pp. 661-666.
Boyer et aL., "Mild Hydrogen-Transfer Reductions Using Sodium Hypophosphite", J. Org. Chem., vol. 50, No. 18, 1985, pp. 3408-3411.
Brunner, Erwin, "Solubility of Hydrogen in 10 Organic Solvents at 298.15, 323.15, and 373.15 K", Journal of Chemical and Engineering Data, vol. 30, No. 3, 1985, pp. 269-273.
Chatterjee et al. "Hydrogenation of 5-Hydroxymethylfurfural in Supercritical Carbon Dioxide—Water: A Tunable Approach to Dimethylfuran Selectivity", Green Chemistry, vol. 16, 2014, pp. 1543-1551.
Chidambaram et al., "A Two-Step Approach for the Catalytic Conversion of Glucose to 2,5-Dimethyl furan in Ionic Liquids", Green Chemistry, vol. 12, 2010, pp. 1253-1262.
Delidovich et al., "Alternative Monomers Based on Lignocellulose and Their Use for Polymer Production", Chemical Reviews, vol. 116, 2016, pp. 1540-1599.
Deutsch et al., "Active Species of Copper Chromite Catalyst in C—O Hydrogenolysis of 5-Methylfurfuryl Alcohol", Journal of Catalysis, vol. 285, 2012, pp. 235-241.
Dutta et al., "Novel Pathways to 2,5-Dimethylfuran via Biomass-Derived 5-(Chloromethyl) Furfural", Chemsuschem, vol. 7, 2014, pp. 3028-3030.
Hamada et al., "Novel Synthetic Route to 2,5-Disubstituted Furan Derivatives through Surface Active Agent-Catalyzed Dehydration of D-(-)-Fructose", J. Oleo Sci., vol. 50. No. 6, 2001, pp. 533-536. (English Abstract Submitted).
Harmon et al., "Hydrogenation of Organic Compounds Using Homogeneous Catalysts", Chemical Reviews, vol. 73, No. 1, 1973, pp. 21-52.

(Continued)

*Primary Examiner* — Taofiq A Solola
(74) *Attorney, Agent, or Firm* — Morrison & Foerster LLP

(57) ABSTRACT

Provided herein are methods of producing dialkylfurans, such as 2,5-dimethylfuran, and other alkyl furans, such as 2-methylfuran. For example, 2,5-dimethylfuran may be produced by hydrogenation of (5-methylfuran-2-yl) methanol or 2-(chloromethyl)-5-methylfuran in the presence of a solid supported metal catalyst having an excess of either basic or acidic sites (as determined by chemisorption of $CO_2$ or $NH_3$). The process could further include a urea reagent (TMU, DMPU, TMI) and an alkyl benzene.

36 Claims, 8 Drawing Sheets

(56) References Cited

OTHER PUBLICATIONS

Iqbal et al., "Conversion of Furfuryl Alcohol into 2-Methylfuran at Room Temperature using Pd/TiO$_2$ Catalyst", Catalysis Science & Technology, vol. 4, 2014, pp. 2280-2286.
Klusoň et al., "Ru—Sn Catalyst—A New Promising System for Selective Hydrogenation of a Carbonyl Group", Chem. Listy, vol. 91, 1997, pp. 100-104.
Kwon et al., "Electrocatalytic Hydrogenation of 5-Hydroxymethylfurfural in the Absence and Presence of Glucose", ChemSusChem, vol. 6, 2013, pp. 1659-1667.
Lange et al., "Furfural—A Promising Platform for Lignocellulosic Biofuels", ChemSusChem, vol. 5, 2012, pp. 150-166.
Lessard et al., "High Yield Conversion of Residual Pentoses into Furfural via Zeolite Catalysis and Catalytic Hydrogenation of Furfural to 2-Methylfuran", Topics in Catalysis, vol. 53, Sep. 2010, pp. 1231-1234.
Liu et al, "One-Pot Conversion of Carbohydrates into Furan Derivatives via Furfural and 5-Hydroxylmethylfurfural as Intermediates", ChemSusChem, vol. 9, 2016, pp. 2015-2036.
Luijkx et al., "Ether Formation in the Hydrogenolysis of Hydroxymethylfurfural over Palladium Catalysts in Alcoholic Solution", Heterocycles, vol. 77, No. 2, 2009, pp. 1037-1044.
Lund et al., "Electrochemical Reduction of Foran Derivatives Derived from Biomass", Acta Chemica Scandinavica, vol. 39 B, No. 6, 1985, pp. 429-435.
Luo et al., "Mechanisms for High Selectivity in the Hydrodeoxygenation of 5-Hydroxymethylfurfural over PtCo Nanocrystals", ACS Catalysis, vol. 6, 2016, pp. 4095-4104.
Luttringhaus et al., "Tetraethylurea as a Solvent and Reagent", Angew. Chem. International Edition. vol. 3, No. 4, 1964, pp. 260-269.
Marques et al., "Facile Hydrodehalogenation with H$_2$ and Pd/C Catalyst under Multiphase Conditions. 3. Selective Removal of Halogen from Functionalized Aryl Ketones. 4. Aryl Halide-Promoted Reduction of Benzyl Alcohols to Alkanes", J. Org. Chem. vol. 60, No. 8, 1995, pp. 2430-2435.
Mascal et al., "Direct, High-Yield Conversion of Cellulose into Biofuel", Angewandte Chemie International Edition, vol. 47, 2008, pp. 7924-7926.
Mitra et al., "Pd/C-Catalyzed Reactions of HMF: Decarbonylation, Hydrogenation, and Hydrogenolysis", Green Chemistry, 2014, 7 pages.
Nakagawa et al., "Catalytic Reduction of Biomass-Derived Furanic Compounds with Hydrogen", ACS Catalysis, vol. 3, 2013, pp. 2655-2668.
Nishimura et al., "Selective Hydrogenation of Biomass-Derived 5-Hydroxymethylfurfural (HMF) to 2,5-Dimethylfuran (DMF) under Atmospheric Hydrogen Pressure over Carbon Supported PdAu Bimetallic Catalyst", Catalysis Today, 2013, pp. 1-10.
International Preliminary Report on Patentability received for PCT Patent Application No. PCT/US2014/051209, dated Feb. 25, 2016, 7 pages.
International Search Report & Written Opinion received for PCT Patent Application No. PCT/US2014/051209, dated Nov. 13, 2014, 9 pages.
International Preliminary Report on Patentability received for PCT Patent Application No. PCT/US2015/045330, dated Mar. 2, 2017, 8 pages.
International Search Report and Written Opinion received for PCT Application No. PCT/US2015/045330, dated Nov. 20, 2015, 11 pages.
Pittman et al., "Sequential Catalytic Condensation-Hydrogenation of Ketones", J. Org. Chem. vol. 45, No. 25, 1980, pp. 5048-5052.
Román-Leshkov et al., "Production of Dimethylfuran for Liquid Fuels from Biomass-Derived Carbohydrates", Nature, vol. 447, Jun. 21, 2007, pp. 982-985.
Rosatella et al., "5-Hydroxymethylfurfural (HMF) as a Building Block Platform: Biological Properties, Synthesis and Synthetic Applications", Green Chemistry, vol. 13, 2011, pp. 754-793.
Schniepp et al., "The Preparation of Acetopropyl Alcohol and 1,4-Pentanediol from Methylfuran", J. Am. Chem. Soc., vol. 69, Mar. 1947, pp. 672-674.
Smith, Patrick B., "Bio-Based Sources for Terephthalic Acid", Green Polymer Chemistry: Biobased Materials and Biocatalysis, Chapter 27, 2015, pp. 453-469.
Stakheev et al., "Specific Features of the Catalytic Behavior of Supported Palladium Nanoparticles in Heterogeneous Catalytic Reactions", Russian Journal of General Chemistry, vol. 80, No. 3, 2010, pp. 618-629.
Thananatthanachon et al., "Efficient Production of the Liquid Fuel 2,5-Dimethylfuran from Fructose Using Formic Acid as a Reagent", Angewandte Chemie International Edition, vol. 49, 2010, pp. 6616-6618.
Wei et al., "One-Pot Production of 2,5-Dimethylfuran from Fructose over Ru/C and a Lewis-Brønsted Acid Mixture in N,N-Dimethylformamide", Catalysis Science & Technology, vol. 6, 2016, pp. 6217-6225.
Yinghuai et al., "Ionic Liquids in Catalytic Biomass Transformation", Chapter 1, Applications of Ionic Liquids in Science and Technology, 2011, pp. 3-26.
Zhang et al., "Highly Active Polymer Anchored Palladium Catalyst for the Hydrodehalogenation of Organic Halides under Mild Conditions", Tetrahedron Letters, vol. 35. No. 26, 1994, pp. 4599-4602.
Non-Final Office Action received for U.S. Appl. No. 14/912,052, dated Jun. 12, 2017, 6 pages.

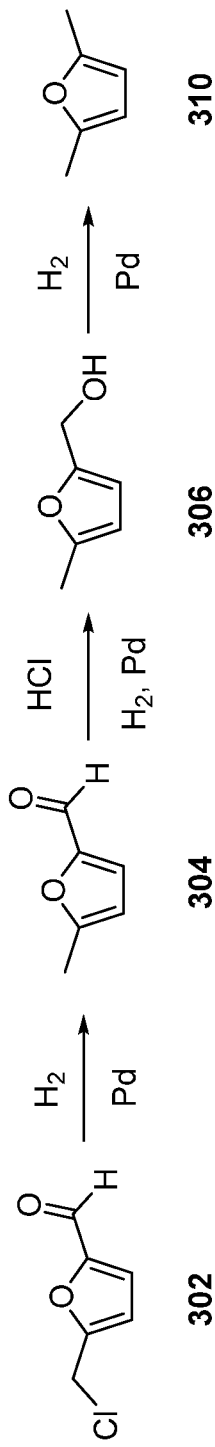
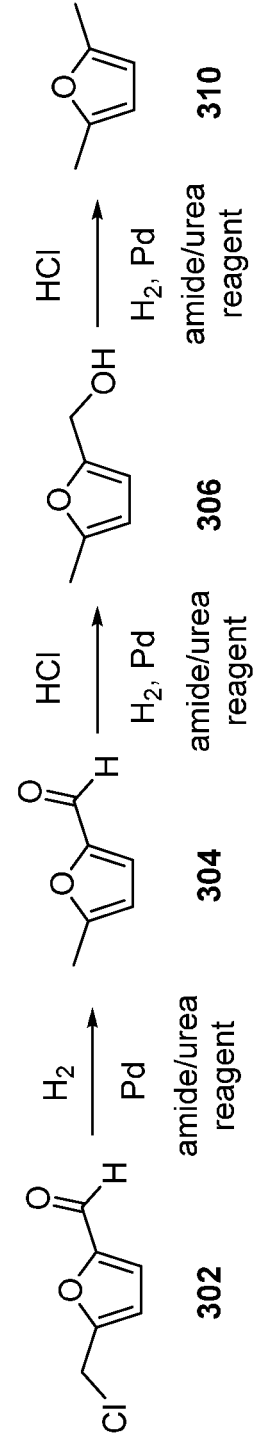
FIG. 3A
FIG. 3A'

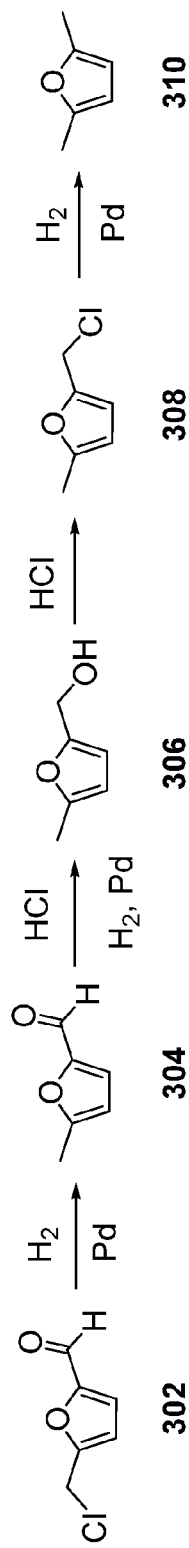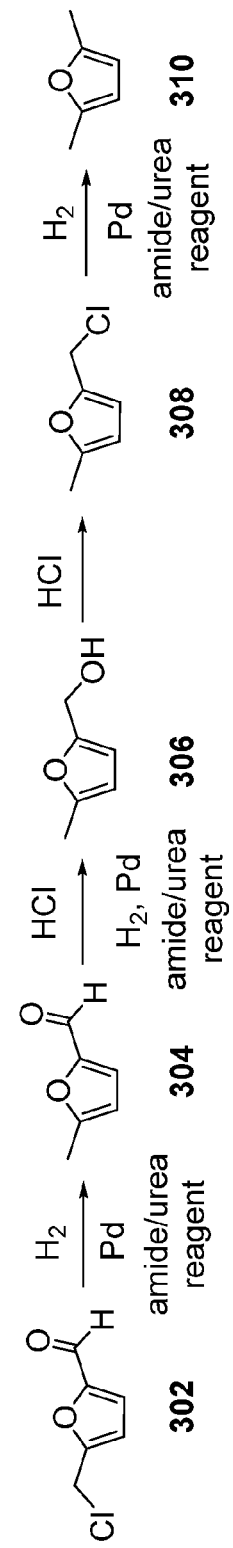
FIG. 3B
FIG. 3B'

600

METHODS OF PRODUCING ALKYLFURANS

CROSS-REFERENCE TO RELATED APPLICATIONS

This application is a U.S. National Phase Patent Application of PCT/US2015/045330, filed Aug. 14, 2015, which claims priority to U.S. Provisional Patent Application No. 62/037,806, filed Aug. 15, 2014, the disclosures of which are herein incorporated by reference in their entirety.

FIELD

The present disclosure relates generally to methods of producing dialkylfurans and other alkylfurans, and more specifically to methods of producing 2,5-dimethylfuran and 2-methylfuran.

BACKGROUND

Dialkylfurans, such as 2,5-dimethylfuran (DMF), and other alkylfurans have potential applications for use as biofuels. Several methods are known in the art to produce 2,5-dimethylfuran. Current methods known in the art to produce 2,5-dimethylfuran from other furan compounds have been challenging with respect to minimizing the furan ring reduction. Thus, what is needed in the art are methods of selectively reducing furan compounds to produce 2,5-dimethylfuran and other alkylfurans.

BRIEF SUMMARY

Provided herein are methods to reduce furan compounds to produce alkylfurans. In some aspects, provided is a method of producing a compound of formula (I'):

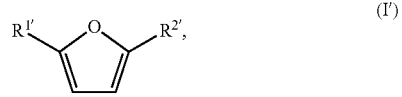

(I')

wherein:
  $R^{1'}$ is $C_m$ alkyl, wherein m is an integer greater than or equal to 0, provided that when m is 0, $R^{1'}$ is H; and
  $R^{2'}$ is $C_n$ alkyl, wherein n is an integer greater than or equal to 1,
by reducing a compound of formula (A) to produce the compound of formula (I'), wherein the compound of formula (A) is:

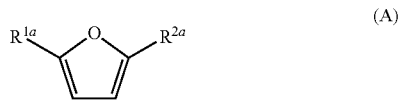

(A)

wherein:
  $R^{1a}$ is $C_m$ alkyl, $-(CH_2)_{m-1}CH(O)$, $-(CH_2)_m OH$, or $-(CH_2)_m Y$, wherein:
    m is as defined for formula (I'), provided that when m is 0, $R^{1a}$ is H; and
    Y is halo; and
  $R^{2a}$ is $-(CH_2)_{n-1}CH(O)$, $-(CH_2)_n OH$, or $-(CH_2)_n X$, wherein:
    n is as defined for formula (I'); and
    X is halo.

In some embodiments, the compound of formula (A) is reduced to produce the compound of formula (I') in the presence of:
  hydrogen,
  a catalyst, and
  a reagent of formula (i), (ii) or (iii), or any combinations thereof,
wherein:
  the reagent of formula (i) is:

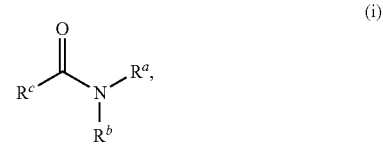

(i)

wherein:
  each $R^a$, $R^b$ and $R^c$ is independently H, aliphatic, aryl, or heteroaryl; or
  $R^a$ and $R^b$ are taken together with the nitrogen atoms to which they are connected to form a cyclic moiety having at least 3 ring atoms; and
the reagent of formula (ii) is:

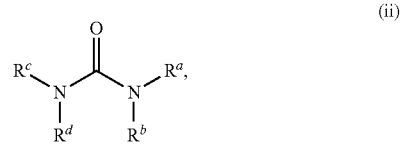

(ii)

wherein:
  (A) each $R^a$, $R^b$, $R^c$ and $R^d$ is independently H, aliphatic, aryl or heteroaryl; or
  (B) $R^a$ and $R^b$ are taken together with the nitrogen atoms to which they are connected to form a cyclic moiety having at least 3 ring atoms; and each $R^c$ and $R^d$ is independently H, aliphatic, aryl or heteroaryl; or
  (C) each $R^a$ and $R^b$ is independently H, aliphatic, aryl or heteroaryl; and $R^c$ and $R^d$ are taken together with the nitrogen atoms to which they are connected to form a cyclic moiety having at least 3 ring atoms; or
  (D) $R^a$ and $R^b$ are taken together with the nitrogen atoms to which they are connected to form a cyclic moiety having at least 3 ring atoms; and $R^c$ and $R^d$ are taken together with the nitrogen atoms to which they are connected to form a cyclic moiety having at least 3 ring atoms; or
  (E) each $R^a$ and $R^c$ is independently H, aliphatic, aryl or heteroaryl; and $R^b$ and $R^d$ are taken together with the nitrogen atoms to which they are connected to form a cyclic moiety having at least 5 ring atoms; or
  (F) each $R^b$ and $R^d$ is independently H, aliphatic, aryl or heteroaryl; and $R^a$ and $R^c$ are taken together with the nitrogen atoms to which they are connected to form a cyclic moiety having at least 5 ring atoms; and the reagent formula (iii) is:

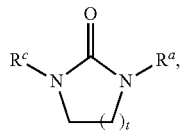

wherein:
  each $R^a$ and $R^c$ is independently H, aliphatic, aryl or heteroaryl; and
  t is an integer greater than or equal to 0.

In some variations of the reagent of formula (iii), t is an integer greater than or equal to 1.

In some variations, the catalyst includes:
(i) a metal; or
(ii) at least two metals; or
(iii) a solid support selected from carbon, silica, alumina, titania, magnesium silicate, aluminosilicate, magnesium oxide, calcium oxide, and zinc oxide, or any combination thereof; or
(iv) both (i) or (iii), or both (ii) or (iii); or
(v) palladium and a solid support selected from silica, titania, magnesium silicate, aluminosilicate, magnesium oxide, calcium oxide, and zinc oxide, or any combination thereof; or
(vi) platinum and a solid support selected from carbon, silica, alumina, titania, magnesium silicate, aluminosilicate, magnesium oxide, calcium oxide, and zinc oxide, or any combination thereof; or
(vii) palladium, and wherein the catalyst is homogeneous.

In some variations, the catalyst is prepared in situ.

In some aspects, provided is a method of producing a compound of formula (I'), as described herein, by converting a compound of formula (A), as described herein, to the compound of formula (I') in the presence of (1) hydrogen and (2) a solid-supported metal catalyst comprising a metal component and a basic solid support.

In other aspects, provided is a method of producing a compound of formula (I'), as described herein, by converting a compound of formula (A), as described herein, to the compound of formula (I') in the presence of (1) hydrogen, (2) a catalyst comprising a metal component and an acidic or neutral solid support, and (3) an amide reagent or a urea reagent, or a combination thereof.

In other aspects, provided is a method of producing a compound of formula (I'), as described herein, by converting a compound of formula (A), as described herein, to the compound of formula (I') in the presence of (1) hydrogen, (2) a catalyst comprising a metal component and a solid support, and (3) an amide reagent or a urea reagent, or a combination thereof, under acidic conditions. In some variations, acidic conditions can be achieved by the use of an acidic solid support in the catalyst, or by addition of an acid, or by generation of an acid in situ.

In yet other aspects, provided is a method of producing a compound of formula (I'), as described herein, by converting a compound of formula (A) to the compound of formula (I') in the presence of (1) hydrogen, (2) a catalyst comprising a metal component and a solid support, (3) an amide reagent or a urea reagent, or a combination thereof, and (4) an acid.

In some variations, provided is a method of producing a compound of formula (I'), as described herein, by converting a compound of formula (A) to the compound of formula (I') in the presence of (1) hydrogen, (2) a catalyst comprising a metal component and a solid support, (3) an amide reagent or a urea reagent, or a combination thereof, (4) an acid, and (5) an aromatic reagent. In certain variations, a urea reagent is used. In one variation, the urea reagent is a cyclic urea reagent.

In yet other aspects, provided is a method of producing a compound of formula (I'):

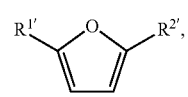

wherein:
  $R^{1'}$ is $C_m$ alkyl, wherein m is an integer greater than or equal to 0, provided that when m is 0, $R^{1'}$ is H; and
  $R^{2'}$ is $C_n$ alkyl, wherein n is an integer greater than or equal to 1,
by:
  a) converting a compound of formula (B) to a compound of formula (C), wherein:
  the compound of formula (B) is:

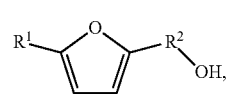

wherein:
    $R^1$ is $C_m$ alkyl, wherein m is as defined for formula (I'); and
    $R^2$ is $—(CH_2)_n—$, wherein n is as defined for formula (I'),
  the compound of formula (C) is:

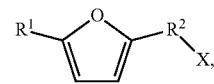

wherein:
    $R^1$ and $R^2$ are as defined for formula (B); and
    X is halo; and
  b) reducing the compound of formula (C) to produce the compound of formula (I').

In some variations, the compound of formula (C) is reduced to produce the compound of formula (I') in the presence of:
  hydrogen,
  a catalyst, and
  any one of reagents of formula (i), (ii) and (iii) described herein, or any combinations thereof.

In one aspect, provided is a method of producing 2,5-dimethylfuran, by:
  a) providing (5-methylfuran-2-yl)methanol; and
  b) selectively reducing the (5-methylfuran-2-yl)methanol to produce 2,5-dimethylfuran.

In some embodiments, the (5-methylfuran-2-yl)methanol is selectively reduced in the presence of hydrogen and a catalyst.

In another aspect, provided is a method of producing 2,5-dimethylfuran, by:
a) providing (5-methylfuran-2-yl)methanol;
b) converting the (5-methylfuran-2-yl)methanol to 2-(chloromethyl)-5-methylfuran in the presence of an acid; and
c) selectively reducing the 2-(chloromethyl)-5-methylfuran to produce 2,5-dimethylfuran.

In some embodiments, the 2-(chloromethyl)-5-methylfuran is selectively reduced in the presence of hydrogen and a catalyst.

In other embodiments, the (5-methylfuran-2-yl)methanol is provided by:
i) providing 5-methylfuran-2-carbaldehyde; and
ii) converting the 5-methylfuran-2-carbaldehyde to (5-methylfuran-2-yl)methanol in the presence of acid, hydrogen and a catalyst.

In yet other embodiments, the (5-methylfuran-2-yl)methanol is provided by:
i) providing 5-(chloromethyl)furfural;
ii) converting the 5-(chloromethyl)furfural to 5-methylfuran-2-carbaldehyde in the presence of hydrogen and a catalyst; and
iii) converting the 5-methylfuran-2-carbaldehyde to the (5-methylfuran-2-yl)methanol in the presence of acid, hydrogen and a catalyst.

In one embodiment, the catalyst is a palladium catalyst.

In other aspects, provided herein are also compositions that include any of the compounds of formula (A), catalysts, hydrogen, and amine and/or urea reagents described herein. In some embodiments, the compositions may also include any of the acids and/or solvents described herein.

In other aspects, provided herein are also methods of producing a compound of formula (J):

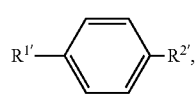

(J)

wherein:
R$^{1'}$ is C$_m$ alkyl, wherein m is an integer greater than or equal to 0, provided that when m is 0, R$^{1'}$ is H; and
R$^{2'}$ is C$_n$ alkyl, wherein n is an integer greater than or equal to 1,
by combining a compound of formula (I') produced according to any of the methods described herein and ethylene to produce the compound of formula (J).

For example, in some embodiments, the compound of formula (I') is 2,5-dimethylfuran; and the compound of formula (J) is para-xylene. In other embodiments, the compound of formula (I') is 2-methylfuran; and the compound of formula (J) is toluene.

In some variations, the compound of formula (J) may be further oxidized, and optionally further polymerized.

DESCRIPTION OF THE FIGURES

The present application can be best understood by reference to the following description taken in conjunction with the accompanying figures, in which like parts may be referred to by like numerals.

DETAILED DESCRIPTION

The following description sets forth exemplary methods, parameters and the like. It should be recognized, however, that such description is not intended as a limitation on the scope of the present disclosure but is instead provided as a description of exemplary embodiments.

Provided herein are methods of producing dialkylfurans, such as 2,5-dialkylfurans, and other alkylfurans, such as 2-alkylfurans.

Figure 1:
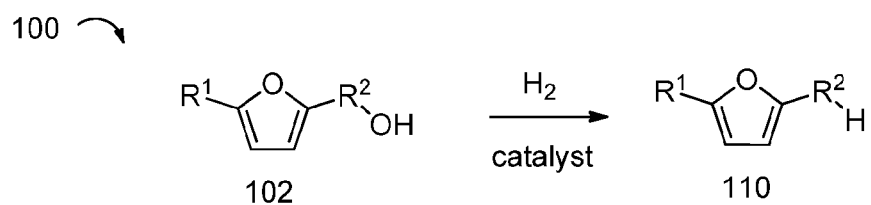
FIGS. 1 and 2 depict exemplary reaction schemes to produce a dialkylfuran.

For example, in one aspect, provided is a method of producing 2,5-dimethylfuran from (5-methylfuran-2-yl)methanol. With reference to FIG. 1, process 100 is an exemplary reaction scheme for producing dialkylfurans 110. In some embodiments, R$^1$ is alkyl, and R$^2$ is —(CH$_2$)$_n$—, where n is an integer and at least 1. In one embodiment, R$^1$ is methyl and R$^2$ is —(CH$_2$)—, such that compound 102 is (5-methylfuran-2-yl)methanol and compound 110 is 2,5-dimethylfuran. Compound 102 may be selectively reduced in the presence of hydrogen and a catalyst, such as palladium (Pd) catalyst. (5-Methylfuran-2-yl)methanol may be converted into 2,5-dimethylfuran by selectively reducing the alcohol functional group of (5-methylfuran-2-yl)methanol without reducing, or by minimizing the prevalence of the reduction of, the furan ring.

Figure 2:
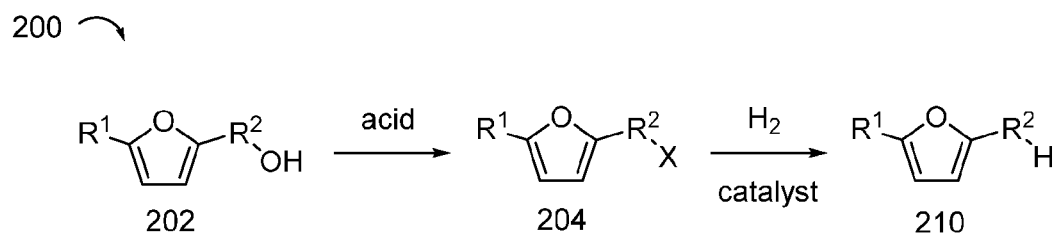

In another aspect, with reference to FIG. 2, process 200 is another exemplary reaction scheme for producing dialkylfurans 210. In some embodiments, R$^1$ is alkyl, and R$^2$ is —(CH$_2$)$_n$—, where n is an integer and at least 1. In one embodiment, R$^1$ is methyl and R$^2$ is —(CH$_2$)—, such that compound 202 is (5-methylfuran-2-yl)methanol, compound 204 is 2-(halomethyl)-5-methylfuran (wherein X is halo), and compound 210 is 2,5-dimethylfuran. (5-Methylfuran-2-yl)methanol may be converted under acidic conditions into 2-(halomethyl)-5-methylfuran, such as 2-(chloromethyl)-5-methylfuran. In one example, (5-methylfuran-2-yl)methanol may be reacted with hydrochloric acid and a salt (e.g., lithium chloride salt) to produce 2-(chloromethyl)-5-methylfuran. With reference again to FIG. 2, 2-(halomethyl)-5-methylfuran, such as 2-(chloromethyl)-5-methylfuran, may subsequently be converted into 2,5-dimethylfuran by selectively reducing the halide functional group of 2-(halomethyl)-5-methylfuran without reducing, or by minimizing the prevalence of the reduction of, the furan ring.

In some embodiments, compounds 102 (FIG. 1) and 202 (FIG. 2) may be obtained from any commercially available sources or produced according to any suitable methods known in the art.

In other embodiments, for example, with reference to FIG. 3A, 5-(chloromethyl)furfural 302 may be converted to 5-methylfuran-2-carbaldehyde 304 in the presence of hydrogen and a catalyst, such as a palladium (Pd) catalyst. In one variation, with reference again to FIG. 3A, 5-methylfuran-2-carbaldehyde 304 may then be reacted with an acid, such as hydrochloric acid, in the presence of hydrogen and a metal catalyst, such as a palladium (Pd) catalyst, to produce (5-methylfuran-2-yl)methanol 306, which may then be reduced to form 2,5-dimethylfuran 310. In other variations, an acid may not be present in the conversion of 5-methylfuran-2-carbaldehyde 304 to (5-methylfuran-2-yl)methanol 306.

In another variation, with reference to FIG. 3A', 5-(chloromethyl)furfural 302 may be converted to 5-methylfuran-2-carbaldehyde 304 in the presence of hydrogen, a catalyst, such as a palladium (Pd) catalyst, and an amide reagent, or a urea reagent, or a combination thereof as described herein. In one variation, with reference again to FIG. 3A', 5-methylfuran-2-carbaldehyde 304 may then be reacted with an acid, such as hydrochloric acid, in the presence of hydrogen, a metal catalyst, such as a palladium (Pd) catalyst, and an amide reagent, or a urea reagent, or a combination thereof as described herein, to produce (5-methylfuran-2-yl)methanol 306, which may then be reduced to form 2,5-dimethylfuran 310. In other variations, an acid may not be present in the conversion of 5-methylfuran-2-carbaldehyde 304 to (5-methylfuran-2-yl)methanol 306. In certain variations, the catalyst used in FIGS. 3A and 3A' may be the same or different. In certain variations, the amide or urea reagents used in FIG. 3A' may be the same or different. In other variations, a combination of amide and urea reagents may be used.

In yet other embodiments, with reference to FIG. 3B, 5-(chloromethyl)furfural 302 may be converted to 5-methylfuran-2-carbaldehyde 304 in the presence of hydrogen and a catalyst, such as a palladium (Pd) catalyst. 5-Methylfuran-2-carbaldehyde 304 may then be reacted with an acid, such as hydrochloric acid, in the presence of hydrogen and a metal catalyst, such as a palladium (Pd) catalyst, to produce (5-methylfuran-2-yl)methanol 306, which may then be converted to 2-(chloromethyl)-5-methylfuran 308, and in turn reduced to form 2,5-dimethylfuran 310. In other variations, an acid may not be present in the conversion of 5-methylfuran-2-carbaldehyde 304 to (5-methylfuran-2-yl)methanol 306.

In yet other embodiments, with reference to FIG. 3B', 5-(chloromethyl)furfural 302 may be converted to 5-methylfuran-2-carbaldehyde 304 in the presence of hydrogen, a catalyst, such as a palladium (Pd) catalyst, and an amide reagent, or a urea reagent, or a combination thereof as described herein. 5-Methylfuran-2-carbaldehyde 304 may then be reacted with an acid, such as hydrochloric acid, in the presence of hydrogen and a metal catalyst, such as a palladium (Pd) catalyst, and an amide reagent, or a urea reagent, or a combination thereof as described herein, to produce (5-methylfuran-2-yl)methanol 306, which may then be converted to 2-(chloromethyl)-5-methylfuran 308, and in turn reduced to form 2,5-dimethylfuran 310. In other variations, an acid may not be present in the conversion of 5-methylfuran-2-carbaldehyde 304 to (5-methylfuran-2-yl)methanol 306. In certain variations, the catalyst used in FIGS. 3B and 3B' may be the same or different. In certain variations, the amide or urea reagents used in FIG. 3B' may be the same or different. In other variations, a combination of amide and urea reagents may be used.

In some embodiments, the reaction may be performed as a "one pot" reaction, in the same reaction vessel and/or without isolating, for example, 5-methylfuran-2-carbaldehyde or (5-methylfuran-2-yl)methanol as depicted in FIGS. 3A, 3A', 3B and 3B'. In other variations, 5-methylfuran-2-carbaldehyde may be isolated prior to conversion to (5-methylfuran-2-yl)methanol.

Figure 3C:
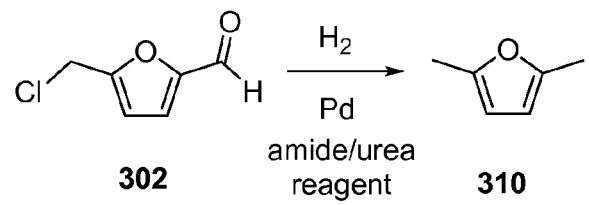
FIGS. 3A, 3A', 3B, 3B', 3C, 3D and 3E depict exemplary reaction schemes to convert 2-(chloromethyl)furfural to 2,5-dimethylfuran.

An example of a one pot reaction is provided in FIG. 3C. Thus, in one variation, with reference to FIG. 3C, 5-(chloromethyl)furfural 302 may be converted to 2,5-dimethylfuran 310 in a one pot reaction. As depicted in the exemplary scheme of FIG. 3C, this conversion may be performed in the presence of hydrogen, a palladium catalyst, and an amide reagent, or a urea reagent, or a combination thereof as described herein. In another variation, this conversion may be performed in the further presence of an acid. In other variations, however, this conversion may be performed with acid generated in situ, in the presence of a palladium catalyst, hydrogen and an amide reagent, or a urea reagent, or a combination thereof as described herein. In other variations, a combination of amide and urea reagents may be used.

Figure 3D:
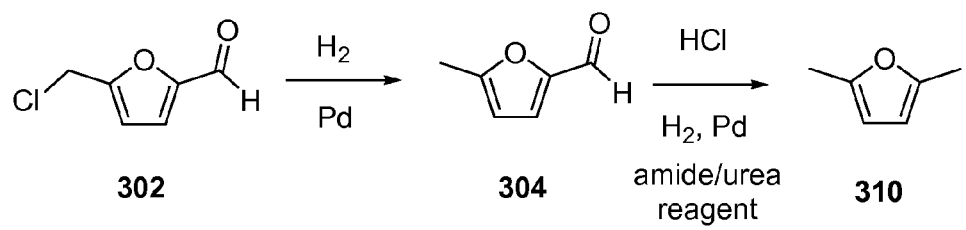

With reference to FIG. 3D, in another exemplary reaction scheme, 5-(chloromethyl)furfural 302 may be converted to 5-methylfuran-2-carbaldehyde 304 in the presence of hydrogen and a catalyst, such as a palladium catalyst. 5-Methylfuran-2-carbaldehyde 304 may in turn be reduced to form 2,5-dimethylfuran 310 in the presence of acid, such as hydrochloric acid, hydrogen, a palladium catalyst (such as palladium on carbon), and an amide reagent, or a urea reagent, or a combination thereof as described herein. In other variations, however, this reduction may be performed with acid generated in situ, in the presence of hydrogen, a palladium catalyst (such as palladium chloride), activated carbon, and an amide reagent, or a urea reagent, or a combination thereof as described herein. In other variations, a combination of amide and urea reagents may be used.

Figure 3E:
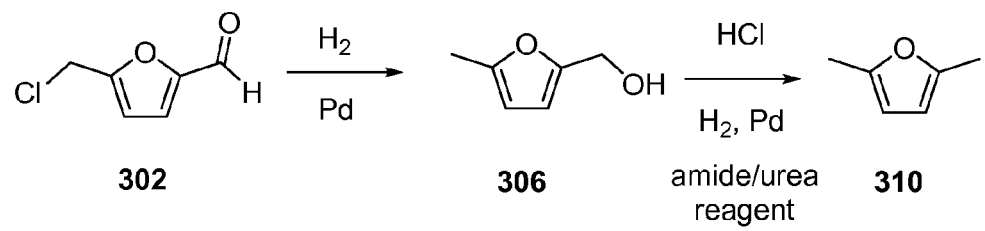

With reference to FIG. 3E, in another exemplary reaction scheme, 5-(chloromethyl)furfural 302 may be converted to (5-methylfuran-2-yl)methanol 306, which may then be reduced to form 2,5-dimethylfuran 310 in the presence of acid, such as hydrochloric acid, hydrogen, a palladium catalyst (such as palladium on carbon), and an amide reagent, or a urea reagent, or a combination thereof as described herein. In other variations, however, this reduction may be performed with acid generated in situ, in the presence of hydrogen, a palladium catalyst (such as palladium chloride), activated carbon, and an amide reagent, or a urea reagent, or a combination thereof as described herein. In other variations, a combination of amide and urea reagents may be used.

5-(Halomethyl)furfural 302 used in the exemplary reaction schemes depicted in FIGS. 3A-3E may be obtained from any commercially available sources or produced by any suitable methods known in the art.

Figure 4A:
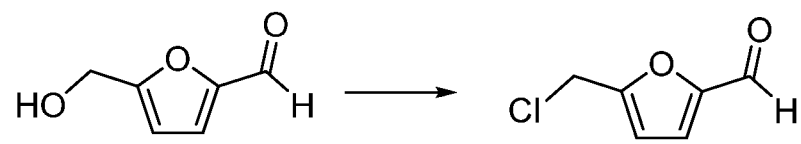
FIGS. 4A and 4B depict exemplary reaction schemes to produce 5-(chloromethyl)furfural.
Figure 4B:
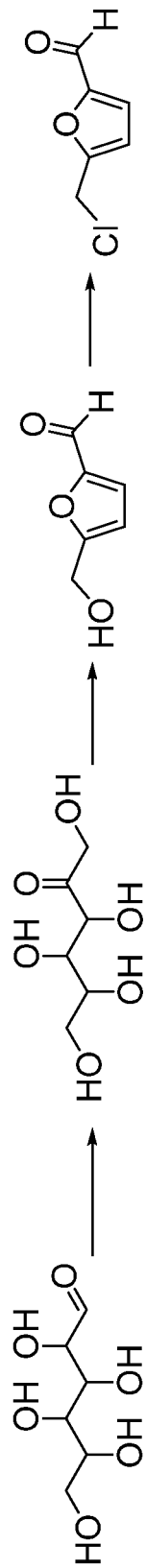

In some embodiments, 5-(halomethyl)furfural may be produced from 5-(hydroxymethyl)furfural, as depicted in the exemplary reactions of FIGS. 4A and 4B. With reference to FIG. 4A, 5-(hydroxymethyl)furfural may be converted into 5-(chloromethyl)furfural in the presence of an acid. In one example, 5-(hydroxymethyl)furfural may be reacted with 10N HCl at room temperature. In another example, 5-(hydroxymethyl)furfural may be reacted with 5N $H^+$ and 11N $Cl^-$ at room temperature.

With reference to FIG. 4B, glucose may be converted to fructose in the presence of an acid and/or salt. For example, in an exemplary reaction, glucose may be converted to fructose using 1N $H^+$, 12N $Cl^-$, 11N $Li^+$, and toluene as a solvent at elevated temperatures (e.g., 110° C.). Fructose may then be converted to 5-(hydroxymethyl)furfural, which may in turn be converted to 5-(chloromethyl)furfural as described above. In other variations, the 5-(chloromethyl) furfural may be produced from fructose or cellulose.

Figure 5A:
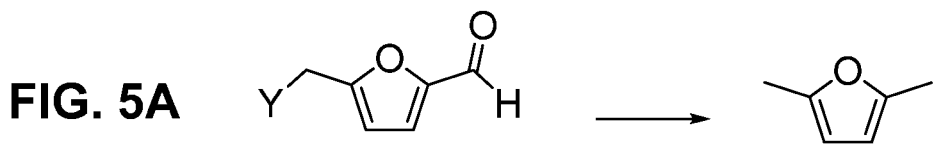
FIGS. 5A-5D, 5H and 5I depict exemplary reaction schemes to produce 2,5-dimethylfuran.
Figure 5B:
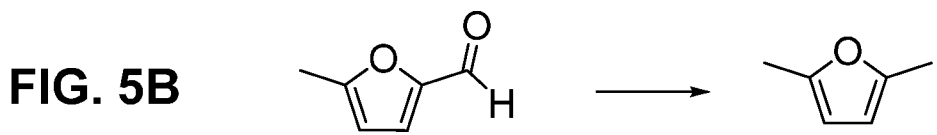
Figure 5C:
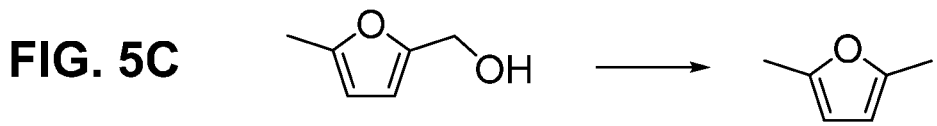
Figure 5D:
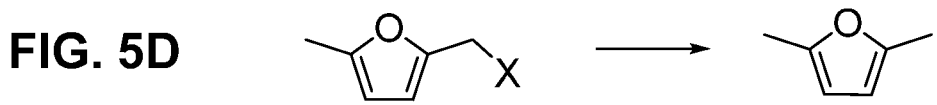

Thus, provided herein are methods to produce alkylfurans from various furan compounds. For example, various furan compounds may be used to produce 2,5-dimethylfuran as shown in the exemplary reaction schemes in FIGS. 5A-5D, 5H and 5I. Such furan compounds may include, for example, 5-(halomethyl)furfural (or also referred to as 5-(halomethyl)furan-2-carbaldehyde; FIG. 5A; where Y is halo), 5-methylfuran-2-carbaldehyde (FIG. 5B), (5-methylfuran-2-yl)methanol (FIG. 5C), 2-(halomethyl)-5-methylfuran (FIG. 5D; where X is halo); furan-2,5-dicarbaldehyde (FIG. 5H); and furan-2,5-diyldimethanol (FIG. 5I).

Figure 5E:
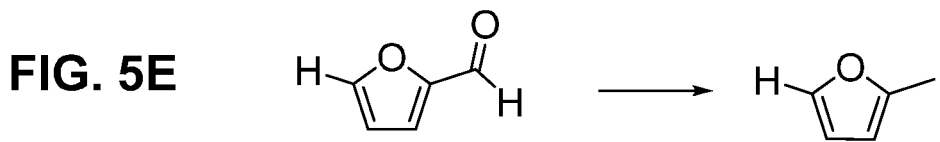
FIGS. 5E-5G depict exemplary reaction schemes to produce 2-methylfuran.
Figure 5F:
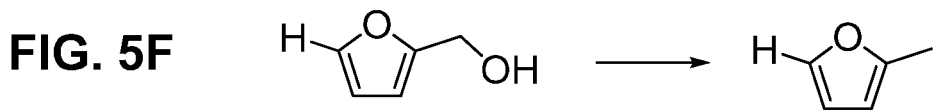
Figure 5G:
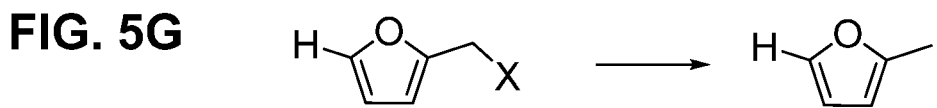
Figure 5H:
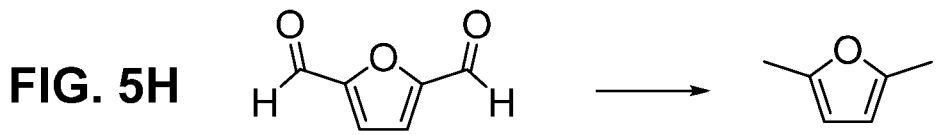
Figure 5I:
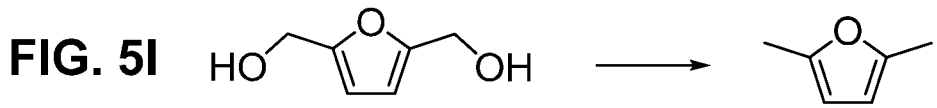

In other examples, various furan compounds may be used to produce 2-methylfuran as shown in the exemplary reaction schemes in FIGS. 5E-5G. Such furan compounds may including, for example, furfural (or also referred to as furan-2-carbaldehyde; FIG. 5E), furan-2-ylmethanol (FIG. 5F), and 2-(halomethyl)furan (FIG. 5G; where X is halo).

Figure 6:
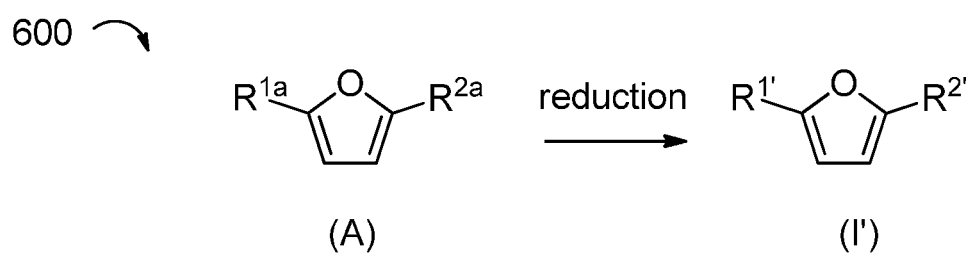
FIG. 6 depicts an exemplary reaction scheme to produce an alkylfuran having the structure of formula (I') from a compound having the structure of formula (A).

With reference in FIG. 6, in some variations, the alkylfurans are compounds having the structure of formula (I'):

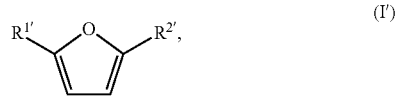

(I')

wherein:

$R^{1'}$ is $C_m$ alkyl, wherein m is an integer greater than or equal to 0, provided that when m is 0, $R^{1'}$ is H; and $R^{2'}$ is $C_n$ alkyl, wherein n is an integer greater than or equal to 1.

Thus, with reference to process 600 in FIG. 6, in certain aspects, provided is a method of producing a compound of formula (I') by reducing a compound of formula (A) having the structure:

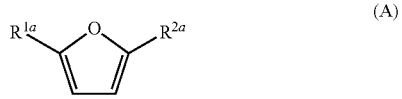

(A)

wherein:

$R^{1a}$ is $C_m$ alkyl, —$(CH_2)_{m-1}CH(O)$, —$(CH_2)_mOH$, or —$(CH_2)_mY$, wherein m is as defined for formula (I'), provided that when m is 0, $R^{1a}$ is H; and Y is halo; and $R^{2a}$ is —$(CH_2)_{n-1}CH(O)$, —$(CH_2)_nOH$, or —$(CH_2)_nX$, wherein n is as defined for formula (I'), and X is halo.

In one variation, the compound of formula (A) is reduced to produce the compound of formula (I') in the presence of a catalyst, and hydrogen. In another variation, the compound of formula (A) is reduced to produce the compound of formula (I') in the presence of a catalyst, hydrogen, and one or more reagents having an amide or urea moiety. In yet another variation, the compound of formula (A) is reduced to produce the compound of formula (I') in the presence of a catalyst, hydrogen, one or more reagents having an amide or urea moiety, and solvent.

The alkylfurans (e.g., the compounds of formula (I')), the furan compounds (e.g., the compounds of formula (A)), the catalysts, the acids, the hydrogen, the amine and urea reagents and the solvents, as well as the reaction conditions to produce the compounds of formula (I') are each described in further detail below.

Alkylfurans

In some aspects, the methods provided herein produce alkylfurans that are compounds having the structure of formula (I"):

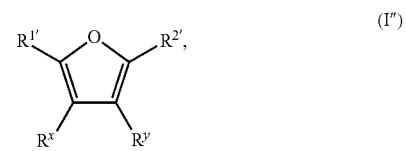

(I")

wherein:

$R^{1'}$ is $C_m$ alkyl, wherein m is an integer greater than or equal to 0, provided that when m is 0, $R^{1'}$ is H;

$R^{2'}$ is $C_n$ alkyl, wherein n is an integer greater than or equal to 1; and $R^x$ and $R^y$ are independently H or alkyl.

In some variations, $R^x$ and $R^y$ are each H. In other variations, $R^x$ and $R^y$ are independently alkyl. In certain variations, $R^x$ is H, and $R^y$ is alkyl; or $R^x$ is alkyl, and $R^y$ is H. In one variation, the alkyl is methyl or ethyl.

In some aspects, the methods provided herein produce alkylfurans that are compounds having the structure of formula (I'):

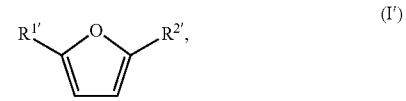

(I')

wherein:

$R^{1'}$ is $C_m$ alkyl, wherein m is an integer greater than or equal to 0, provided that when m is 0, $R^{1'}$ is H; and $R^{2'}$ is $C_n$ alkyl, wherein n is an integer greater than or equal to 1.

In some variations, the methods provided herein produce compounds having the structure of formula (I'), wherein m is 0, and thus $R^{1'}$ is H. Examples of such compounds include compounds of formula (I-a):

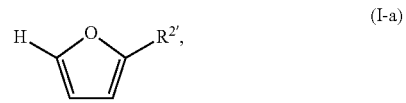

(I-a)

wherein:

$R^{2'}$ is $C_n$ alkyl, wherein n is an integer greater than or equal to 1.

Thus, in some variations, provided herein are methods of producing a compound of formula (I-a) from a compound of formula (A).

In other variations, the methods provided herein produce compounds having the structure of formula (I'), wherein $R^{1'}$ is $C_m$ alkyl, wherein m is an integer greater than or equal to 1. Examples of such compounds include compounds of formula (I-b):

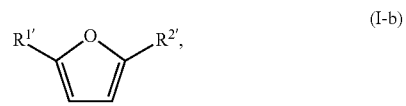

(I-b)

wherein:

R$^{1'}$ is C$_m$ alkyl, wherein m is an integer greater than or equal to 1; and R$^{2'}$ is C$_n$ alkyl, wherein n is an integer greater than or equal to 1.

Thus, in some variations, provided herein are methods of producing a compound of formula (I-b) from a compound of formula (A).

In some aspects, the methods provided herein produce dialkylfurans having the structure of formula (I):

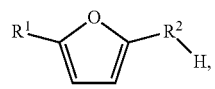

(I)

wherein:

R$^1$ is C$_m$ alkyl, wherein m is an integer greater than or equal to 1; and

R$^2$ is —(CH$_2$)$_n$—, wherein n is an integer greater than or equal to 1.

Thus, in some variations, provided herein are methods of producing a dialkylfuran of formula (I) from a compound of formula (A).

In some variations of the compounds of formula (I") or (I'), m is 0. In other variations of the compound of formula (I"), (I'), (I) or (I-b), m is between 1 and 50, between 1 and 25, between 1 and 20, between 1 and 15, between 1 and 10, or between 1 and 5. In certain variations, m is 1, 2, 3, 4, or 5. In one variation, m is 1.

In some variations of the compounds of formula (I"), (I'), (I), (I-a) or (I-b), n is between 1 and 50, between 1 and 25, between 1 and 20, between 1 and 15, between 1 and 10, or between 1 and 5. In certain variations, n is 1, 2, 3, 4, or 5. In one variation, n is 1.

In other variations of the compounds of formula (I"), (I'), (I), (I-a) or (I-b), it should be understood that any combinations of variables m and n described above can be used. For example, in certain variations of the compounds of formula (I"), (I'), (I) or (I-b), m is between 1 and 50; and n is between 1 and 50. In one variation, m is 1, and n is 2. In another variation of the compounds of formula (I") or (I'), m is 0, and n is 1. Variables m and n may, in certain embodiments, be the same integer or a different integer.

In certain embodiments, the compounds of formula (I"), (I') or (I-a) may be an alkylfuran such as:

(i.e., 2-methylfuran), wherein m is 0 and n is 1.

In certain embodiments, the compounds of formula (I"), (I'), (I) or (I-b) may be a dialkylfuran such as:

(i.e., 2,5-dimethylfuran), wherein m is 1, and n is 1; or (i.e., 2-ethyl-5-methylfuran), wherein m is 2, and n is 1; or m is 1, and n is 2.

It should be understood that the methods described herein to produce the compounds of formulae (I") and (I') also apply to the compounds of formulae (I), (I-a) and (I-b), to the extent that is chemically feasible.

Compounds of Formula (A)

In some aspects, the methods provided herein produce compounds of formula (I") from compounds of formula (A"):

(A")

wherein:

R$^{1a}$ is C$_m$ alkyl, —(CH$_2$)$_{m-1}$CH(O), —(CH$_2$)$_m$OH, or —(CH$_2$)$_m$Y, wherein:

m is an integer greater than or equal to 0, provided that when m is 0, R$^{1a}$ is H; and Y is halo;

R$^{2a}$ is —(CH$_2$)$_{n-1}$CH(O), —(CH$_2$)$_n$OH, or —(CH$_2$)$_n$X, wherein:

n is an integer greater than or equal to 1; and

X is halo; and

R$^x$ and R$^y$ are independently H or alkyl.

In some variations, R$^x$ and R$^y$ are each H. In other variations, R$^x$ and R$^y$ are independently alkyl. In certain variations, R$^x$ is H, and R$^y$ is alkyl; or R$^x$ is alkyl, and R$^y$ is H. In one variation, the alkyl is methyl or ethyl.

In some aspects, the methods provided herein produce compounds of formula (I') from compounds of formula (A):

(A)

wherein:

R$^{1a}$ is C$_m$ alkyl, —(CH$_2$)$_{m-1}$CH(O), —(CH$_2$)$_m$OH, or —(CH$_2$)$_m$Y, wherein:

m is an integer greater than or equal to 0, provided that when m is 0, R$^{1a}$ is H; and Y is halo; and R$^{2a}$ is —(CH$_2$)$_{n-1}$CH(O), —(CH$_2$)$_n$OH, or —(CH$_2$)$_n$X, wherein:

n is an integer greater than or equal to 1; and

X is halo.

In some embodiments, R$^{1a}$ is C$_m$ alkyl or —(CH$_2$)$_m$Y. In other embodiments, R$^{1a}$ is —(CH$_2$)$_{m-1}$CH(O) or —(CH$_2$)$_m$OH.

In some variations, the methods provided herein produce compounds having the structure of formula (I'), wherein m is 0, and thus R$^{1'}$ is H, from compounds of formula (A-i):

(A-i)

wherein:

R$^{2a}$ is —(CH$_2$)$_{n-1}$CH(O), —(CH$_2$)$_n$OH, or —(CH$_2$)$_n$X, wherein n is as defined for formula (I'), and X is halo.

In other variations, the methods provided herein produce compounds having the structure of formula (I'), wherein $R^{1'}$ is $C_m$ alkyl, wherein m is an integer greater than or equal to 1. Examples of such compounds include compounds of formula (A-ii):

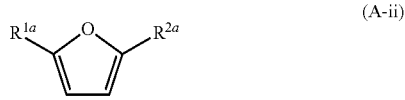

wherein:
$R^{1a}$ is $C_m$ alkyl, or $-(CH_2)_mY$, wherein:
m is an integer greater than or equal to 1; and
Y is halo; and
$R^{2a}$ is $-(CH_2)_{n-1}CH(O)$, $-(CH_2)_nOH$, or $-(CH_2)_nX$, wherein:
n is an integer greater than or equal to 1, and
X is halo.

In some variations of the compounds of formulae (A") and (A), $R^{1a}$ is H. Examples of such compounds include:

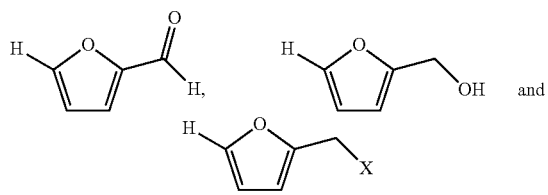

(wherein X is halo).

In other variations of the compounds of formulae (A") and (A), $R^{1a}$ is $C_m$ alkyl. For example, in one variation, $R^{1a}$ is methyl (i.e., $C_1$ alkyl), ethyl (i.e., $C_2$ alkyl), or propyl (i.e., $C_3$ alkyl). Examples of such compounds include:

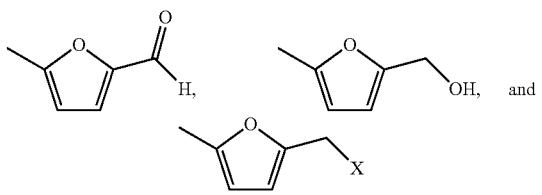

(wherein X is halo).

In yet other variations of the compounds of formulae (A"), (A) and (A-ii), $R^{1a}$ is $-(CH_2)_mY$. For example, in one variation, $R^{1a}$ is $-CH_2Y$, $-CH_2CH_2Y$, or $-CH_2CH_2CH_2Y$. In one embodiment, Y is chloro. In another embodiments, Y is bromo. In yet another embodiment, Y is fluoro. Examples of such compounds include:

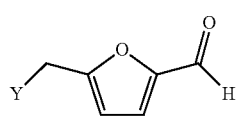

(wherein Y is halo).

In some variations of the compounds of formulae (A"), (A), (A-i) and (A-ii) that may be combined with any of the foregoing variations, $R^{2a}$ is $-(CH_2)_{n-1}CH(O)$. Examples of such compounds include:

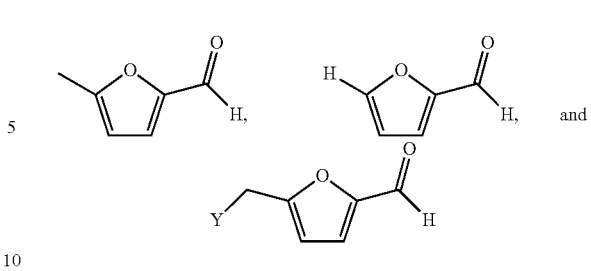

(wherein Y is halo).

In other variations of the compounds of formulae (A"), (A), (A-i) and (A-ii) that may be combined with any of the foregoing variations, $R^{2a}$ is $-(CH_2)_nOH$. Examples of such compounds include:

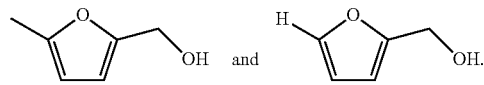

In other variations of the compounds of formulae (A"), (A), (A-i) and (A-ii) that may be combined with any of the foregoing variations, $R^{2a}$ is $-(CH_2)_nX$. In one embodiment, X is chloro. In another embodiments, X is bromo. In yet another embodiment, X is fluoro. Examples of such compounds include:

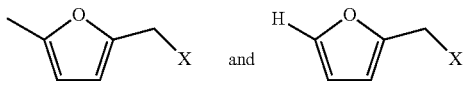

(wherein X is halo).

It should be understood that any variations of $R^{1a}$ and $R^{2a}$ may be combined as if each and every variation was individually listed. For example, with reference to FIG. 5A, the compound of formula (A) is

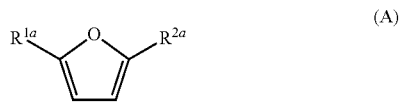

wherein:
$R^{1a}$ is $-(CH_2)_mY$, wherein:
m is an integer greater than or equal to 1; and
Y is halo; and
$R^{2a}$ is $-(CH_2)_{n-1}CH(O)$, wherein:
n is an integer greater than or equal to 1.

In one variation, the compound of formula (A) is:

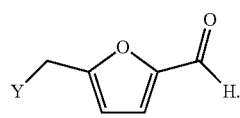

In another example, with reference to FIG. 5B, the compound of formula (A) is:

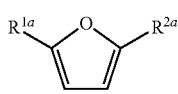
(A)

wherein:
$R^{1a}$ is $C_m$ alkyl, wherein:
m is an integer greater than or equal to 1; and
$R^{2a}$ is —$(CH_2)_{n-1}CH(O)$, wherein:
n is an integer greater than or equal to 1.
In one variation, the compound of formula (A) is:

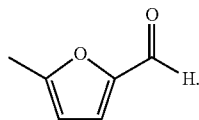

In another example, with reference to FIG. 5C, the compound of formula (A) is:

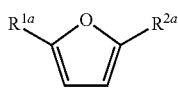
(A)

wherein:
$R^{1a}$ is $C_m$ alkyl, wherein:
m is an integer greater than or equal to 1; and
$R^{2a}$ is —$(CH_2)_n OH$, wherein:
n is an integer greater than or equal to 1.
In one variation, the compound of formula (A) is:

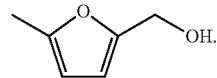

In yet another example, with reference to FIG. 5D, the compound of formula (A) is:

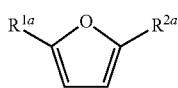
(A)

wherein:
$R^{1a}$ is $C_m$ alkyl, wherein:
m is an integer greater than or equal to 1; and
$R^{2a}$ is —$(CH_2)_n X$, wherein:
n is an integer greater than or equal to 1; and
X is halo.
In one variation, the compound of formula (A) is:

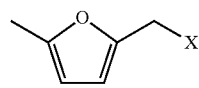

(wherein X is halo).
In another example, with reference to FIG. 5E, the compound of formula (A) is:

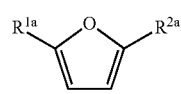
(A)

wherein:
$R^{1a}$ is H; and
$R^{2a}$ is —$(CH_2)_{n-1}CH(O)$, wherein:
n is an integer greater than or equal to 1.
In one variation, the compound of formula (A) is:

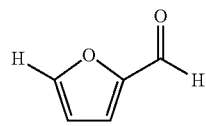

In yet another example, with reference to FIG. 5F, the compound of formula (A) is:

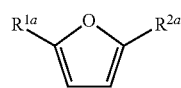
(A)

wherein:
$R^{1a}$ is H; and
$R^{2a}$ is —$(CH_2)_n OH$, wherein:
n is an integer greater than or equal to 1.
In one variation, the compound of formula (A) is:

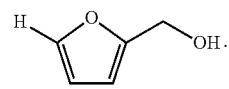

In yet another example, with reference to FIG. 5G, the compound of formula (A) is:

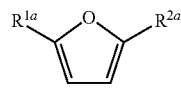
(A)

wherein:
$R^{1a}$ is H; and
$R^{2a}$ is —$(CH_2)_n X$, wherein:
n is an integer greater than or equal to 1; and
X is halo.
In one variation, the compound of formula (A) is:

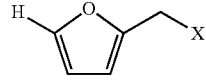

(wherein X is halo).
In yet another example, with reference to FIG. 5H, the compound of formula (A) is:

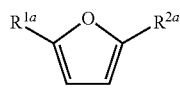

(A)

wherein:
R$^{1a}$ is —(CH$_2$)$_{m-1}$CH(O), wherein:
  m is an integer greater than or equal to 0; and
R$^{2a}$ is —(CH$_2$)$_{n-1}$CH(O) wherein:
  n is an integer greater than or equal to 1.
In one variation, the compound of formula (A) is:

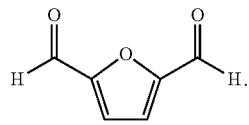

In yet another example, with reference to FIG. 5I, the compound of formula (A) is:

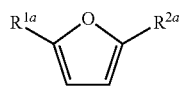

(A)

wherein:
R$^{1a}$ is —(CH$_2$)$_m$OH, wherein:
  m is an integer greater than or equal to 0; and
R$^{2a}$ is —(CH$_2$)$_n$OH, wherein:
  n is an integer greater than or equal to 1.
In one variation, the compound of formula (A) is:

In some variations of the compounds of formula (A") and (A), m is 0. In some variations of the compound of formula (A"), (A), (A-i) or (A-ii), m is between 1 and 50, between 1 and 25, between 1 and 20, between 1 and 15, between 1 and 10, or between 1 and 5. In certain variations, m is 1, 2, 3, 4, or 5. In one variation, m is 1.

In some variations of the compounds of formula (A"), (A), (A-i) or (A-ii), n is between 1 and 50, between 1 and 25, between 1 and 20, between 1 and 15, between 1 and 10, or between 1 and 5. In certain variations, n is 1, 2, 3, 4, or 5. In one variation, n is 1.

In other variations of the compounds of formula (A"), (A), (A-i) or (A-ii), it should be understood that any combinations of variables m and n described above can be used. For example, in certain variations of the compound of formula (I') or (I), m is between 1 and 50; and n is between 1 and 50. In one variation, m is 1, and n is 2. In another variation, m is 0, and n is 1. Variables m and n may, in certain embodiments, be the same integer or a different integer.

In certain embodiments, the compounds of formula (A"), (A) or (A-i) may be:

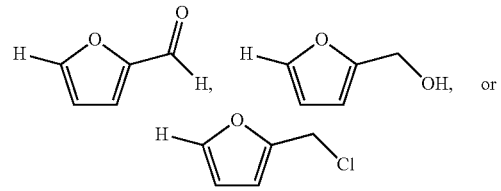

(wherein m is 0 and n is 1 in each instance).

In certain embodiments, the compounds of formula (A"), (A) or (A-ii) may be:

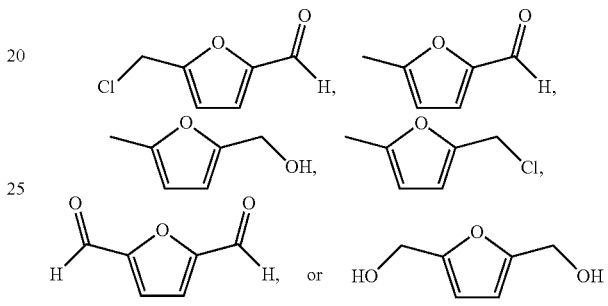

(wherein m is 1 and n is 1 in each instance).

Catalysts

In some variations of the methods provided herein to produce alkylfurans (e.g., compounds of formulae (I"), (I'), (I), (I-a) and (I-b)), the corresponding compounds of formulae (A"), (A), (A-i) and (A-ii) may be reduced in the presence of a catalyst. The catalysts used herein may be obtained from any commercially available sources or prepared according to any suitable methods known in the art. Suitable catalysts include any catalysts that can improve selectivity of the formation of dialkylfurans and other alkylfurans, while minimizing the formation of other products.

In certain embodiments, the catalyst is a metal catalyst. In some variations, the catalyst includes a noble metal. Noble metals include, for example, ruthenium, rhodium, palladium, silver, osmium, iridium, platinum, and gold.

In other variations, the catalyst includes at least one transition metal. In one embodiment, the catalyst includes only one metal. In other embodiments, the catalyst includes two or more metals. In certain embodiments, the catalyst includes two metals or three metals.

In some variations, the catalyst includes at least one Group 10 metal, either alone or in combination with another Group 10 metal or with at least one Group 11 metal. It should be understood that the group number used for the metals follow the IUPAC or long-form nomenclature, which is well-known in the art. In one embodiment, the Group 10 metal is palladium or platinum. Thus, in some variations, the catalyst includes palladium, platinum, or a combination thereof. For example, in one variation, the catalyst is palladium on carbon (Pd/C) or palladium chloride (PdCl$_2$).

In certain variations, the catalyst further includes at least one Group 11 metal. In one variation, the Group 11 metal is copper, gold, or silver. Thus, in some variations, the catalyst includes (i) palladium or platinum, and (ii) at least one additional metal selected from the group consisting of gold, silver, and copper, or any combination thereof.

In some embodiments, the catalyst includes:
(i) palladium;
(ii) palladium and platinum;
(iii) palladium and gold;
(iv) palladium and copper;
(v) palladium and silver;
(vi) platinum;
(vii) platinum and gold;
(viii) platinum and copper; or
(ix) platinum and silver.

In certain embodiments, the catalyst includes:
(i) palladium;
(ii) palladium and platinum;
(iii) palladium and gold;
(iv) palladium and copper;
(v) palladium and silver;
(vi) platinum and copper;
(vii) platinum and gold; or
(viii) platinum and silver.

In certain embodiments, the catalyst includes:
(i) palladium and platinum;
(ii) palladium and gold;
(iii) palladium and copper;
(iv) palladium and silver;
(v) platinum and gold;
(vi) platinum and copper; or
(vii) platinum and silver.

In one embodiment, the catalyst includes:
(i) palladium and platinum;
(ii) palladium and gold; or
(iii) palladium and silver.

In other embodiments, the catalyst further includes a promoter, which may alter the acid/base characteristics of the catalyst. For example, the promoter may be any substance that can further improve selectivity of the formation of dialkylfurans and other alkylfurans. In certain embodiments, the promoter acts as a base. For example, in some variations, the promoter is an alkali metal. In certain variations, the promoter is selected from Group 1 or Group 2. In one variation, the promoter is potassium. An example of a catalyst that includes a promoter may be a catalyst made up of palladium, gold and potassium.

The amount of metal present in the catalyst may vary. For example, in some embodiments where the catalyst includes palladium and at least one additional metal, the palladium and the at least one additional metal are present in the catalyst in a weight ratio of 0.5 to 20. In other embodiments where the catalyst includes platinum and at least one additional metal, the palladium and the at least one additional metal are present in the catalyst in a weight ratio of 0.5 to 20. In some variations, the amounts of the metal present described above do not include the amount of promoter present in the catalyst.

In other embodiments, the catalyst has a total metal loading between 0.1% to 15% by weight. It should be understood that the "total metal loading" of a catalyst refers to the sum of the weight percent of the metals (e.g., Group 10 metal, Group 11 metal) present in the catalyst. In some variations, the total metal loading described above does not include the weight percent of a promoter (if present).

In some embodiments, the catalyst may be a homogeneous or heterogeneous catalyst in the reaction mixture. In one variation, the catalyst is homogeneous in the reaction mixture. Such homogeneous catalysts may include, for example, palladium chloride, palladium acetate, (2,2'-bipyridine)dichloropalladium(II), bis(triphenylphosphine)palladium(II) dichloride, tris(dibenzylideneacetone)dipalladium (0).

In another variation, the catalyst is heterogeneous in the reaction mixture. In certain embodiments, the catalyst further includes a solid support. Thus, in some embodiments, the catalyst is a solid-supported catalyst. In one embodiment, the catalyst is a solid-supported metal catalyst. In some variations, the solid-supported metal catalyst used herein is metal catalyst where the metal is deposited or impregnated onto a support. In other variations, the solid-supported metal catalyst is metal catalyst where the metal is precipitated onto a support.

In some variations, the solid support includes carbon, a Group 3 metal oxide, a Group 13 metal oxide, a Group 4 metal oxide, a Group 14 metal oxide, or a Group 5 metal oxide, or any combination thereof. In certain variations, the solid support includes carbon, silica, alumina, titania, magnesium silicate, aluminosilicate, magnesium oxide, calcium oxide, or zinc oxide, or any combination thereof. In one variation, the solid support includes carbon, alumina, magnesium oxide, or zeolite, or any combination thereof.

In some variations, examples of suitable catalysts used herein may include:
Pd/Al$_2$O$_3$;
Pd/C;
Pd+Pt/MgO;
Pd+Au/MgO;
Pd/MgO;
Pd/ZSM5;
Pd/Beta zeolite;
Pd+Au+K/C;
Pd+Ag/C;
Pd+Pt/C;
Pt+Cu/C;
Pt+Au/C;
Pt+Ag/C; or
Pd+Au/C; or
or any combination thereof.

In one variation, the catalyst is:
Pd/Al$_2$O$_3$;
Pd/C;
2.5% Pd+1.5% Pt/MgO;
3% Pd+0.5% Au/MgO;
4% Pd/MgO;
4% Pd/ZSM5;
4% Pd/Beta zeolite;
4% Pd/C;
3% Pd+0.5% Au+0.6% K/C;
3% Pd+0.5% Au+0.3% K/C;
3% Pd+1.0% Ag/C;
3% Pd+0.5% Au/C;
3% Pd+1% Au/C;
2% Pd+2% Pt/C;
2% Pd+2% Ag/C;
4% Pt+0.5% Cu/C;
3% Pt+2.0% Au/C;
3% Pt+1% Ag/C;
3% Pd+1.0% Au/C; or
3% Pt+1.0% Ag/C,
or any combination thereof.

It should be understood that the metal loading on a support is given in weight % for a specific metal based on the weight of the catalyst. For example, a 3% Pd+0.5% Au/MgO has 3 weight % palladium (as the zero valent metal) and 0.5 weight % gold on a magnesium oxide support. In some variations where the catalyst includes a promoter, the metal loading described above does not include the weight percent of the promoter.

Any suitable methods or techniques known in the art may be employed to prepare the catalysts, including the solid-supported catalysts, used in the methods provided herein to produce dialkylfurans. For example, supported metal catalysts can be prepared by impregnation, deposition-precipitation, and chemical vapor deposition.

In some embodiments, the metal catalysts provided herein are prepared by impregnation. In one variation, metal may be added to a support by incipient wetness. One of skill in the art would recognize that incipient wetness impregnation is a commonly used technique for the synthesis of heterogeneous catalysts. The active metal precursor may be dissolved in an aqueous or organic solution. Then, the metal-containing solution may be added to a catalyst support containing the same pore volume as the volume of the solution that was added. Capillary action draws the solution into the pores. Solution added in excess of the support pore volume may cause the solution transport to change from a capillary action process to a diffusion process, which is typically slower. The catalyst can then be dried and calcined to drive off the volatile components within the solution, depositing the metal on the catalyst surface. The maximum loading is limited by the solubility of the precursor in the solution. After drying, the catalyst can be treated in hydrogen (or other reducing agent) to convert the metal component to a lower valent form (e.g., "0" valent).

In another example, for some of the palladium catalysts described herein, palladium chloride may be used as a precursor. For other bimetallic systems, other chloride containing precursors were used for the second metal, for example cupric chloride, hexachloroplatinic acid, gold chloride trihydrate. For other systems, such as a Pd/Ag bimetallic catalyst, silver nitrate and palladium nitrate (or diamine palladium dinitrite) may be used. The metal precursors are typically dissolved in water, but some non-aqueous preparations may also be used. In another example, a bimetallic Pd/Au system may be prepared on a MgO support. In this case, palladium acetate and gold acetate may be used as precursors and dissolved in acetonitrile.

Solid-Supported Metal Catalysts with Basic Solid Support

In some embodiments of the methods provided herein to produce alkylfurans, the compound of formula (A") or (A) is converted to the alkylfuran in the presence of (1) hydrogen and (2) a solid-supported metal catalyst that includes a metal component and a basic solid support.

The metal component may include any of the metals described herein. In some variations, the metal component includes at least one, at least two, or at least three metals; or between one and five, between one and four, or between one and three metals; or one, two or three metals. In one variation, the metal components includes a noble metal. In another variation, the metal component includes at least one Group 10 metal. In another variation, the metal component includes (i) at least one Group 10 metal, and (ii) at least one Group 11 metal. For example, in one variation, the metal component includes (i) palladium, or platinum, or a combination thereof; and (ii) gold, silver, or copper, or any combination thereof.

In one variation, the metal component includes palladium and at least one additional metal, wherein the palladium and the least one additional metal are present in the catalyst in a weight ratio of 0.1 to 20; 0.2 to 20, 0.3 to 20; 0.4 to 20; 0.5 to 20; 0.6 to 20; 0.7 to 20; 0.8 to 20; 0.9 to 20; 1 to 20; 5 to 20; 10 to 20; 0.1 to 15; 0.2 to 15, 0.3 to 15; 0.4 to 15; 0.5 to 15; 0.6 to 15; 0.7 to 15; 0.8 to 15; 0.9 to 15; 1 to 15; 5 to 15; 10 to 15; 0.1 to 10; 0.2 to 10, 0.3 to 10; 0.4 to 10; 0.5 to 10; 0.6 to 10; 0.7 to 10; 0.8 to 10; 0.9 to 10; 1 to 10; or 5 to 10.

In some variations, the metal component includes:
(i) palladium;
(ii) palladium and platinum;
(iii) palladium and gold;
(iv) palladium and copper;
(v) palladium and silver;
(vi) platinum;
(vii) platinum and gold;
(viii) platinum and copper; or
(ix) platinum and silver.

In certain variations, the catalyst has a total metal loading between 0.1% to 20% by weight; between 0.1% to 15% by weight; between 0.1% to 10% by weight; between 0.1% to 5% by weight; or between 0.1% to 1% by weight.

In some embodiments, a basic solid support is a solid support that (i) has more basic sites than acidic sites and (ii) chemisorbs at least 0.001 g carbon dioxide/g solid support. In some variations, the basic solid support chemisorbs at least 0.005 g carbon dioxide/g solid support, at least 0.01 g carbon dioxide/g solid support, at least 0.05 g carbon dioxide/g solid support, at least 0.1 g carbon dioxide/g solid support, at least 0.2 g carbon dioxide/g solid support, at least 0.25 g carbon dioxide/g solid support, at least 0.3 g carbon dioxide/g solid support, at least 0.35 g carbon dioxide/g solid support, at least 0.4 g carbon dioxide/g solid support, at least 0.45 g carbon dioxide/g solid support, at least 0.5 g carbon dioxide/g solid support, at least 0.55 g carbon dioxide/g solid support, at least 0.6 g carbon dioxide/g solid support, at least 0.65 g carbon dioxide/g solid support, or at least 0.7 g carbon dioxide/g solid support; or between 0.005 g carbon dioxide/g solid support and 0.75 g carbon dioxide/g solid support, between 0.001 g carbon dioxide/g solid support and 0.75 g carbon dioxide/g solid support, between 0.01 g carbon dioxide/g solid support and 0.75 g carbon dioxide/g solid support, between 0.1 g carbon dioxide/g solid support and 0.75 g carbon dioxide/g solid support, between 0.15 g carbon dioxide/g solid support and 0.75 g carbon dioxide/g solid support, between 0.2 g carbon dioxide/g solid support and 0.75 g carbon dioxide/g solid support, between 0.25 g carbon dioxide/g solid support and 0.75 g carbon dioxide/g solid support, between 0.3 g carbon dioxide/g solid support and 0.75 g carbon dioxide/g solid support, between 0.35 g carbon dioxide/g solid support and 0.75 g carbon dioxide/g solid support, between 0.4 g carbon dioxide/g solid support and 0.75 g carbon dioxide/g solid support, between 0.45 g carbon dioxide/g solid support and 0.75 g carbon dioxide/g solid support, between 0.5 g carbon dioxide/g solid support and 0.75 g carbon dioxide/g solid support, between 0.55 g carbon dioxide/g solid support and 0.75 g carbon dioxide/g solid support, between 0.6 g carbon dioxide/g solid support and 0.75 g carbon dioxide/g solid support, between 0.65 g carbon dioxide/g solid support and 0.75 g carbon dioxide/g solid support, between 0.005 g carbon dioxide/g solid support and 0.7 g carbon dioxide/g solid support, between 0.005 g carbon dioxide/g solid support and 0.65 g carbon dioxide/g solid support, between 0.005 g carbon dioxide/g solid support and 0.6 g carbon dioxide/g solid support, between 0.005 g carbon dioxide/g solid support and 0.55 g carbon dioxide/g solid support, between 0.005 g carbon dioxide/g solid support and 0.5 g carbon dioxide/g solid support, between 0.005 g carbon dioxide/g solid support and 0.45 g carbon dioxide/g solid support, between 0.005 g carbon dioxide/g solid support and 0.4 g carbon dioxide/g solid support, between 0.005 g carbon dioxide/g solid support and 0.35 g carbon dioxide/g solid support, between 0.005 g carbon dioxide/g solid support and 0.3 g carbon dioxide/g solid support, between 0.005 g carbon dioxide/g solid support and 0.25 g carbon dioxide/g solid support, between 0.005 g carbon dioxide/g solid support and 0.2 g carbon dioxide/g solid support, between 0.005 g carbon dioxide/g solid support and 0.15 g carbon dioxide/g solid support, between 0.005 g carbon dioxide/g solid support and 0.1 g carbon dioxide/g solid support, between 0.005 g carbon dioxide/g solid support and 0.01 g carbon dioxide/g solid support, or between 0.25 g carbon dioxide/g solid support and 0.5 g carbon dioxide/g solid support.

One of skill in the art would recognize that a basic site is a site that can chemically react with an acidic adsorbate, including, for example, carbon dioxide ($CO_2$). In one variation, a basic solid support chemisorbs more moles of carbon dioxide ($CO_2$) than ammonia ($NH_3$). Any suitable techniques or methods known in the art to determine the basicity of a material (e.g., a solid support) based on carbon dioxide adsorption (e.g., carbon dioxide chemisorbtion) may be employed.

In some variations, the number of acidic sites of the basic solid support may be at least 2-fold, at least 5-fold, at least 10-fold, at least 50-fold, at least 100-fold, at least 150-fold, or at least 200-fold, or between 100-fold and 500-fold, between 100-fold and 250-fold than the number of basic sites.

It should generally be understood that the basicity of the solid support refers to the overall basicity of the solid support. One of skill in the art would also appreciate that solid bases can generally be classified by their main or predominant surface property, for example, as set forth in Chapter 5 entitled "Solid Acid and Base Catalysts" by K. Tanabe in Anderson & Boudart, Catalysis—Science & Technology, Vol. 2 (1981).

In some variations, the basic solid support includes a metal oxide. In certain variations, the basic solid support includes a basic metal oxide. In certain variations, a basic metal oxide is a metal oxide that has more basic sites than acidic sites. In some variations, the number of acidic sites of the basic metal oxide may be at least 2-fold, at least 5-fold, at least 10-fold, at least 50-fold, at least 100-fold, at least 150-fold, or at least 200-fold, or between 100-fold and 500-fold, between 100-fold and 250-fold lower than the number of basic sites. It should generally be understood that the basicity of the metal oxide refers to the overall basicity of the metal oxide.

In other variations, the basic solid support includes an alkali earth metal oxide.

In some embodiments, the metal oxides that make up the basic solid support are selected from BeO, MgO, CaO, SrO, BaO, ZnO, $Al_2O_3$, $Y_2O_3$, $La_2O_3$, $CeO_2$, $ThO_2$, $TiO_2$, $ZrO_2$ and $SnO_2$. In certain embodiments, the metal oxides that make up the basic solid support are selected from BeO, MgO, CaO, SrO, BaO, $Y_2O_3$, and $La_2O_3$. In one variation, the metal oxide is MgO.

It should generally be understood that certain metal oxides, such as $Al_2O_3$, may also be used in the acidic solid support, as further described below, if the $Al_2O_3$ has more acidic sites than basic sites; and the $Al_2O_3$ used in a basic solid support has more basic sites than acidic sites.

In other variations, the basic solid support includes a mixed metal oxide. In some embodiments, the mixed metal oxides in the basic solid support are selected from $SiO_2$—MgO, $SiO_2$—CaO, $SiO_2$—SrO, $SiO_2$—BaO, $SiO_2$—ZnO, $SiO_2$—$Al_2O_3$, $SiO_2$—$ThO_2$, $SiO_2$—$TiO_2$, $SiO_2$—ZrO, $SiO_2$—$MoO_3$, $SiO_2$—$WO_3$, $Al_2O_3$—MgO, $Al_2O_3$—$ThO_2$, $Al_2O_3$—$TiO_2$, $Al_2O_3$—$ZrO_2$, $Al_2O_3$—$Mn_2O_3$, $Al_2O_3$—$WO_3$, $ZrO_2$—ZnO, $ZrO_2$—$TiO_2$, and $TiO_2$—MgO.

Any combinations of the metal oxides and mixed metal oxides described herein may be included in the basic solid support.

In other variations, the basic solid support is a base-modified solid support. A solid support may be modified to make the solid support basic in nature. Various methods may be employed to modify the solid support to make the solid support basic in nature. For example, a solid support may be combined with an alkali metal or alkali earth metal, or treated with a base (e.g., at a high temperature). Such base may include, for example, ammonia.

In certain variations, an acidic solid support or a neutral solid support may be modified to make the solid support basic in nature. For example, the acidic solid support or the neutral solid support may be combined with an alkali metal or alkali earth metal, or treated with a base (e.g., at a high temperature), after which the solid support is overall basic.

In one variation, carbon, aluminum oxide (also known in the art as alumina) or silicon dioxide (also known in the art as silica) may be combined with an alkali metal or alkali earth metal to produce a base-modified solid support. In another example, carbon, aluminum oxide or silicon dioxide may be treated with a base to produce a base-modified solid support. The carbon, aluminum oxide or silicon dioxide may be treated with ammonia to produce a base-modified solid support. The carbon, aluminum oxide or silicon dioxide may also be treated at elevated temperatures to produce the base-modified solid support.

Examples of solid-supported metal catalyst that includes the metal component and the basic solid support described herein include: Pd+Pt/MgO, Pd+Au/MgO, and Pd/MgO. Any combinations of such solid-supported metal catalysts may also be used in the methods described herein.

Such basic solid supports may be obtained from any commercially available sources. Alternatively, any suitable methods known in the art and as described herein to prepare the solid-supported metal catalyst may be employed. For example, the solid-supported metal catalysts can be prepared by impregnation, deposition-precipitation, and chemical vapor deposition. In one variation, the metal component is impregnated or deposited onto the basic solid support. In another variation the metal component is precipitated onto the basic solid support.

Solid-Supported Metal Catalysts with Acidic Solid Support

In some embodiments of the methods provided herein to produce alkylfurans, the compound of formula (A") or (A) is converted to the alkylfuran in the presence of (1) hydrogen and (2) a solid-supported metal catalyst that includes a metal component and an acidic solid support.

The metal component may include any of the metals described herein. In some variations, the metal component includes at least one, at least two, or at least three metals; or between one and five, between one and four, or between one and three metals; or one, two or three metals. In one variation, the metal components includes a noble metal. In another variation, the metal component includes at least one Group 10 metal. In another variation, the metal component includes (i) at least one Group 10 metal, and (ii) at least one Group 11 metal. For example, in one variation, the metal component includes (i) palladium, or platinum, or a combination thereof; and (ii) gold, silver, or copper, or any combination thereof.

In one variation, the metal component includes palladium and at least one additional metal, wherein the palladium and the least one additional metal are present in the catalyst in a weight ratio of 0.1 to 20; 0.2 to 20, 0.3 to 20; 0.4 to 20; 0.5 to 20; 0.6 to 20; 0.7 to 20; 0.8 to 20; 0.9 to 20; 1 to 20; 5 to 20; 10 to 20; 0.1 to 15; 0.2 to 15, 0.3 to 15; 0.4 to 15; 0.5 to 15; 0.6 to 15; 0.7 to 15; 0.8 to 15; 0.9 to 15; 1 to 15; 5 to 15; 10 to 15; 0.1 to 10; 0.2 to 10, 0.3 to 10; 0.4 to 10; 0.5 to 10; 0.6 to 10; 0.7 to 10; 0.8 to 10; 0.9 to 10; 1 to 10; or 5 to 10.

In some variations, the metal component includes:
(i) palladium;
(ii) palladium and platinum;
(iii) palladium and gold;
(iv) palladium and copper;
(v) palladium and silver;
(vi) platinum;
(vii) platinum and gold;
(viii) platinum and copper; or
(ix) platinum and silver.

In certain variations, the catalyst has a total metal loading between 0.1% to 20% by weight; between 0.1% to 15% by weight; between 0.1% to 10% by weight; between 0.1% to 5% by weight; or between 0.1% to 1% by weight.

In some embodiments, an acidic solid support is a solid support that (i) has more acidic sites than basic sites, and (ii) chemisorbs at least 0.001 g ammonia/g solid support. In some variations, the acidic solid support chemisorbs at least 0.002 g ammonia/g solid support, at least 0.003 g ammonia/g solid support, at least 0.004 g ammonia/g solid support, at least 0.005 g ammonia/g solid support, at least 0.001 g ammonia/g solid support, at least 0.05 g ammonia/g solid support, at least 0.01 g ammonia/g solid support, at least 0.1 g ammonia/g solid support, at least 0.2 g ammonia/g solid support, at least 0.25 g ammonia/g solid support, at least 0.3 g ammonia/g solid support, at least 0.35 g ammonia/g solid support, at least 0.4 g ammonia/g solid support, at least 0.45 g ammonia/g solid support, or at least 0.5 g ammonia/g solid support; or between 0.001 g ammonia/g solid support and 0.5 g ammonia/g solid support, between 0.002 g ammonia/g solid support and 0.5 g ammonia/g solid support, between 0.003 g ammonia/g solid support and 0.5 g ammonia/g solid support, between 0.004 g ammonia/g solid support and 0.5 g ammonia/g solid support, between 0.005 g ammonia/g solid support and 0.5 g ammonia/g solid support, between 0.006 g ammonia/g solid support and 0.5 g ammonia/g solid support, between 0.007 g ammonia/g solid support and 0.5 g ammonia/g solid support, between 0.008 g ammonia/g solid support and 0.5 g ammonia/g solid support, between 0.009 g ammonia/g solid support and 0.5 g ammonia/g solid support, between 0.01 g ammonia/g solid support and 0.5 g ammonia/g solid support, between 0.05 g ammonia/g solid support and 0.5 g ammonia/g solid support, between 0.1 g ammonia/g solid support and 0.5 g ammonia/g solid support, between 0.2 g ammonia/g solid support and 0.5 g ammonia/g solid support, between 0.3 g ammonia/g solid support and 0.5 g ammonia/g solid support, between 0.4 g ammonia/g solid support and 0.5 g ammonia/g solid support, between 0.1 g ammonia/g solid support and 0.3 g ammonia/g solid support, between 0.2 g ammonia/g solid support and 0.25 g ammonia/g solid support, or between 0.25 g ammonia/g solid support and 0.5 g ammonia/g solid support.

One of skill in the art would recognize that an acidic site is a site that can chemically react with a basic adsorbate, including, for example, ammonia ($NH_3$). Any suitable techniques or methods known in the art to determine the acidity of a material (e.g., a solid support) based on ammonia adsorption (e.g., ammonia chemisorbtion) may be employed.

In some variations, the number of basic sites of the acidic solid support may be at least 2-fold, at least 5-fold, at least 10-fold, at least 50-fold, at least 100-fold, at least 150-fold, or at least 200-fold, or between 100-fold and 500-fold, between 100-fold and 250-fold lower than the number of acidic sites.

It should generally be understood that the acidity of the solid support refers to the overall acidity of the solid support. One of skill in the art would appreciate that solid acids can generally be classified by their main or predominant surface property, for example, as set forth in Chapter 5 entitled "Solid Acid and Base Catalysts" by K. Tanabe in Anderson & Boudart, Catalysis—Science & Technology, Vol. 2 (1981).

In some variations, the acidic solid support includes a metal oxide. In certain variations, the acidic solid support includes an acidic metal oxide. In certain variations, an acidic metal oxide is a metal oxide that has more acidic sites than basic sites. In some variations, the number of basic sites of the acidic metal oxide may be at least 2-fold, at least 5-fold, at least 10-fold, at least 50-fold, at least 100-fold, at least 150-fold, or at least 200-fold, or between 100-fold and 500-fold, between 100-fold and 250-fold lower than the number of acidic sites. It should generally be understood that the acidity of the metal oxide refers to the overall acidity of the metal oxide.

In some embodiments, the metal oxides in the acidic solid support are selected from $SiO_2$, $ZnO$, $CdO$, $Al_2O_3$, $CeO_2$, $ThO_2$, $TiO_2$, $ZrO_2$, $SnO_2$, $PbO$, $As_2O_3$, $Bi_2O_3$, $Sb_2O_5$, $V_2O_5$, $Cr_2O_3$, $MoO_3$ and $WO_3$. In one variation, the metal oxide is $SiO_2$. In another variation, the metal oxide is $Al_2O_3$.

It should generally be understood that certain metal oxides, such as $Al_2O_3$, may also be used in the basic solid support, as further described above, if the $Al_2O_3$ has more basic sites than acidic sites; and the $Al_2O_3$ used in an acidic solid support has more acidic sites than basic sites.

In other variations, the acidic solid support includes a mixed metal oxide. In some embodiments, the mixed metal oxides in the acidic solid support are selected from $SiO_2$—$Al_2O_3$, $SiO_2$—$TiO_2$, $SiO_2$—$SnO_2$, $SiO_2$—$ZrO_2$, $SiO_2$—$BeO$, $SiO_2$—$MgO$, $SiO_2$—$CaO$, $SiO_2$—$SrO$, $SiO_2$—$ZnO$, $SiO_2$—$Ga_2O_3$, $SiO_2$—$YrO_3$, $Si$—$O_2$—$La_2O_3$, $SiO_2$—$MoO_3$, $SiO_2$—$WO_3$, $SiO_2$—$V_2O_5$, $SiO_2$—$ThO_2$, $Al_2O_3$—$MgO$, $Al_2O_3$—$ZnO$, $Al_2O_3$—$CdO$, $Al_2O_3$—$B_2O_3$, $Al_2O_3$—$ThO_2$, $Al_2O_3$—$TiO_2$, $Al_2O_3$—$ZrO_2$, $Al_2O_3$—$V_2O_5$, $Al_2O_3$—$MoO_3$, $Al_2O_3$—$WO_3$, $Al_2O_3$—$Cr_2O_3$, $Al_2O_3$—$Mn_2O_3$, $Al_2O_3$—$Fe_2O_3$, $Al_2O_3$—$Co_3O_4$, $Al_2O_3$—$NiO$, $TiO_2$—$CuO$, $TiO_2$—$MgO$, $TiO_2$—$ZnO$, $TiO_2$—$CdO$, $TiO_2$—$ZrO_2$, $TiO_2$—$SnO_2$, $TiO_2$—$Bi_2O_3$, $TiO_2$—$Sb_2O_5$, $TiO_2$—$V_2O_5$, $TiO_2$—$Cr_2O_3$, $TiO_2$—$MoO_3$, $TiO_2$—$WO_3$, $TiO_2$—$Mn_2O_3$, $TiO_2$—$Fe_2O_3$, $TiO_2$—$Co_3O_4$, $TiO_2$—$NiO$, $ZrO_2$—$CdO$, $ZnO$—$MgO$, $ZnO$—$Fe_2O_3$, $MoO_3$—$CoO$—$Al_2O_3$, $MoO_3$—$NiO$—$Al_2O_3$, $TiO_2$—$SiO_2$—$MgO$, and $MoO_3$—$Al_2O_3$—$MgO$. Any combinations of the metal oxides and mixed metal oxides described herein may be included in the acidic solid support.

In yet other variations, the acidic solid support includes a zeolite. For example, such zeolites may include ZSM5 and Beta zeolite.

In other variations, the acidic solid support is an acid-modified solid support. A solid support may be modified to make the solid support acidic in nature. Various methods may be employed to modify the solid support to make the solid support acidic in nature. In certain variations, an basic solid support may be modified to make the acidic support basic in nature.

Examples of such solid-supported metal catalyst that includes the metal component and the acidic solid support described herein include: $Pd/Al_2O_3$; $Pd/ZSM5$; $Pd/Beta$ zeolite; $Pd+Au/Al_2O_3$; $Pd+Ag/Al_2O_3$; and $Pd+Cu/Al_2O_3$. In one variation, the solid-supported metal catalyst is $Pd/Al_2O_3$. Any combinations of such solid-supported metal catalysts may also be used in the methods described herein.

Such acidic solid supports may be obtained from any commercially available sources. Alternatively, any suitable methods known in the art and as described herein to prepare the solid-supported metal catalyst may be employed. For example, the solid-supported metal catalysts can be prepared by impregnation, deposition-precipitation, and chemical vapor deposition. In one variation, the metal component is impregnated or deposited onto the acidic solid support. In another variation the metal component is precipitated onto the acidic solid support.

In some embodiments of the methods described herein, when an acidic solid support is used in the solid-supported metal catalyst, an amide reagent, or a urea reagent, or a combination thereof, may also be used. Any of the amide and urea reagents described herein may be used. In other embodiments, when an acidic solid support is used in the solid-supported metal catalyst, an aromatic reagent may also be used. Any of the aromatic reagents described herein may be used.

Solid-Supported Metal Catalysts with Neutral Solid Support

In some embodiments of the methods provided herein to produce alkylfurans, the compound of formula (A") or (A) is converted to the alkylfuran in the presence of (1) hydrogen and (2) a solid-supported metal catalyst that includes a metal component and a neutral solid support.

The metal component may include any of the metals described herein. In some variations, the metal component includes at least one, at least two, or at least three metals; or between one and five, between one and four, or between one and three metals; or one, two or three metals. In one variation, the metal components includes a noble metal. In another variation, the metal component includes at least one Group 10 metal. In another variation, the metal component includes (i) at least one Group 10 metal, and (ii) at least one Group 11 metal. For example, in one variation, the metal component includes (i) palladium, or platinum, or a combination thereof; and (ii) gold, silver, or copper, or any combination thereof.

In one variation, the metal component includes palladium and at least one additional metal, wherein the palladium and the least one additional metal are present in the catalyst in a weight ratio of 0.1 to 20; 0.2 to 20, 0.3 to 20; 0.4 to 20; 0.5 to 20; 0.6 to 20; 0.7 to 20; 0.8 to 20; 0.9 to 20; 1 to 20; 5 to 20; 10 to 20; 0.1 to 15; 0.2 to 15, 0.3 to 15; 0.4 to 15; 0.5 to 15; 0.6 to 15; 0.7 to 15; 0.8 to 15; 0.9 to 15; 1 to 15; 5 to 15; 10 to 15; 0.1 to 10; 0.2 to 10, 0.3 to 10; 0.4 to 10; 0.5 to 10; 0.6 to 10; 0.7 to 10; 0.8 to 10; 0.9 to 10; 1 to 10; or 5 to 10.

In some variations, the metal component includes:
(i) palladium;
(ii) palladium and platinum;
(iii) palladium and gold;
(iv) palladium and copper;
(v) palladium and silver;
(vi) platinum;
(vii) platinum and gold;
(viii) platinum and copper; or
(ix) platinum and silver.

In certain variations, the catalyst has a total metal loading between 0.1% to 20% by weight; between 0.1% to 15% by weight; between 0.1% to 10% by weight; between 0.1% to 5% by weight; or between 0.1% to 1% by weight.

A neutral solid support is any solid support other than a basic solid support and an acidic solid support, as described herein.

In some variations, the neutral solid support is carbon. In one variation, the neutral solid support is activated carbon.

Such neutral solid supports may be obtained from any commercially available sources. Alternatively, any suitable methods known in the art and as described herein to prepare the solid-supported metal catalyst may be employed. For example, the solid-supported metal catalysts can be prepared by impregnation, deposition-precipitation, and chemical vapor deposition. In one variation, the metal component is impregnated or deposited onto the neutral solid support. In another variation the metal component is precipitated onto the neutral solid support.

Examples of such solid-supported metal catalyst that includes the metal component and the neutral solid support described herein include: Pd/C; Pd+Au+K/C; Pd+Ag/C; Pd+Pt/C; Pt+Cu/C; Pt+Au/C; Pt+Ag/C; and Pd+Au/C. In some variations, the solid-supported metal catalyst is Pd+Au+K/C; Pd+Ag/C; Pd+Pt/C; Pt+Cu/C; Pt+Au/C; Pt+Ag/C; and Pd+Au/C. Any combinations of such solid-supported metal catalysts may also be used in the methods described herein.

In some embodiments of the methods described herein, when a neutral solid support is used in the solid-supported metal catalyst, an amide reagent, or a urea reagent, or a combination thereof, may also be used. Any of the amide and urea reagents described herein may be used. In other embodiments, when an neutral solid support is used in the solid-supported metal catalyst, an aromatic reagent may also be used. Any of the aromatic reagents described herein may be used.

Catalyst Regeneration

The catalysts used in the methods described herein can be regenerated and recycled. For example, the solid-supported metal catalyst used in the conversion of the compound of formula (A") or (A) to the alkylfurans described herein may become a residual solid-supported metal catalyst. In some variations, the methods described herein further includes isolating the residual metal catalyst. In other variations, the methods described herein further includes: regenerating the residual solid-supported metal catalyst to produce a regenerated solid-supported metal catalyst; and combining the regenerated solid-supported metal catalyst with additional compound of formula (A") or (A) to produce the alkylfurans described herein.

Any suitable methods known in the art may be used to regenerate the catalysts. For example, the residual metal catalyst can be treated with air and heat at elevated temperatures (e.g., 500° C.), followed by reduction with $H_2$ and heat (e.g., 225° C.).

Acid

In some variations of the methods provided herein to produce alkylfurans, the compounds of formula (A") or (A) are converted to alkylfurans in the presence of (1) hydrogen and (2) a catalyst comprising a metal component and a solid support. In certain variations of the methods provided herein to produce alkylfurans, the compounds of formula (A") or (A) are converted to alkylfurans in the presence of (1) hydrogen, (2) a catalyst comprising a metal component and a solid support, and (3) an amide reagent, or a urea reagent, or a combination thereof under acidic conditions. For example, the use of an acidic solid support and/or the addition of an acid or generation of acid in situ may contribute to the acidic conditions.

In some variations of the methods provided herein to produce alkylfurans, the compounds of formula (A") or (A) may be reduced in the further presence of acid. In certain variations of the methods provided herein to produce alkylfurans, the compounds of formula (A") or (A) are converted to alkylfurans in the presence of (1) hydrogen, (2) a catalyst comprising a metal component and a solid support, (3) an amide reagent, or a urea reagent, or a combination thereof, and (4) an acid.

In some embodiments, the acid is a Bronsted acid. In some embodiments, the acid has a formula H—X, where X is halo. In one variation where the acid is H—X, X is chloro. In another variation, X is bromo. In yet another variation, X is fluoro.

In other embodiments, the acid is sulfonic acid. In yet other variations, the acid is a solid acid.

Such acid may be added to the reaction mixture or generated in situ from the catalysts described herein. For example, in one variation, hydrochloric acid may be generated in situ in the reaction mixture from 5-(chloromethyl)furfural in the presence of hydrogen. In other variations, hydrochloric acid may be generated in situ in the reaction mixture from 5-(chloromethyl)furfural in the presence of a catalyst and/or carbon (e.g., activated carbon).

The amounts of acid present in the reaction mixture may vary based on the compound of formula (A") or (A), the catalyst, the amount of hydrogen, and the amide reagent, or the urea reagent, or a combination thereof reagent. In certain variations, the amount of acid present in the reaction mixture does not exceed an amount that would decrease the activity of the catalyst.

In other variations, the amount of acid present in the reaction mixture is an amount that results in a yield of at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99%, with respect to the compound of formula (I"), (I), (I'), (I-a) or (I-b).

Amide and Urea Reagents

In some variations of the methods provided herein to produce alkylfurans, the compounds of formula (A") or (A) may be reduced in the presence of a reagent that has an amide or urea moiety. The reagents described herein may, under certain conditions, also act as a solvent.

In some embodiments, the reagent is a compound of formula (i):

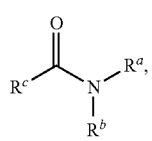

(i)

wherein:
each $R^a$, $R^b$ and $R^c$ is independently H, aliphatic, aryl, or heteroaryl; or
$R^a$ and $R^b$ are taken together with the nitrogen atoms to which they are connected to form a cyclic moiety having at least 3 ring atoms.

In some variations of the reagent of formula (i), each $R^a$, $R^b$ and $R^c$ is independently H, alkyl, aryl, or heteroaryl. In certain variations, each $R^a$ and $R^b$ is independently alkyl. In one variation, each $R^a$ and $R^b$ is independently $C_{1-4}$ alkyl. In other variations, $R^c$ is H, alkyl, or aryl. In certain variations, $R^c$ is H, $C_{1-4}$ alkyl, or $C_{5-12}$ aryl. In one variation, $R^c$ is H, methyl, ethyl, or phenyl.

In yet other variations, $R^c$ is alkyl, aryl or heteroaryl. In certain variations, the reagent of formula (i) is other than N,N-dimethylformamide and N,N-dimethylacetamide. In other variations of the reagent of formula (i), when $R^c$ is H or methyl, then one of $R^a$ and $R^b$ is other than methyl.

In other embodiments, the reagent is a compound of formula (ii):

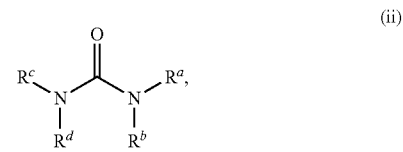

(ii)

wherein:
(A) each $R^a$, $R^b$, $R^c$ and $R^d$ is independently H, aliphatic, aryl or heteroaryl; or
(B) $R^a$ and $R^b$ are taken together with the nitrogen atoms to which they are connected to form a cyclic moiety having at least 3 ring atoms; and each $R^c$ and $R^d$ is independently H, aliphatic, aryl or heteroaryl; or
(C) each $R^a$ and $R^b$ is independently H, aliphatic, aryl or heteroaryl; and $R^c$ and $R^d$ are taken together with the nitrogen atoms to which they are connected to form a cyclic moiety having at least 3 ring atoms; or
(D) $R^a$ and $R^b$ are taken together with the nitrogen atoms to which they are connected to form a cyclic moiety having at least 3 ring atoms; and $R^c$ and $R^d$ are taken together with the nitrogen atoms to which they are connected to form a cyclic moiety having at least 3 ring atoms; or
(E) each $R^a$ and $R^c$ is independently H, aliphatic, aryl or heteroaryl; and $R^b$ and $R^d$ are taken together with the nitrogen atoms to which they are connected to form a cyclic moiety having at least 5 ring atoms; or
(F) each $R^b$ and $R^d$ is independently H, aliphatic, aryl or heteroaryl; and $R^a$ and $R^c$ are taken together with the nitrogen atoms to which they are connected to form a cyclic moiety having at least 5 ring atoms.

In some variations of the reagent of formula (ii), each $R^a$, $R^b$ and $R^c$ is independently H, alkyl, aryl, or heteroaryl. In certain variations, each $R^a$ and $R^b$ is independently alkyl. In one variation, each $R^a$ and $R^b$ is independently $C_{1-4}$ alkyl. In other variations, $R^c$ is H, alkyl, or aryl. In certain variations, $R^c$ is H, $C_{1-4}$ alkyl, or $C_{5-12}$ aryl. In one variation, $R^c$ is H, methyl, ethyl, or phenyl.

In some variations of the reagent of formula (ii), $R^a$ and $R^b$ are taken together with the nitrogen atoms to which they are connected to form a cyclic moiety having at least 4, or at least 5, or between 3 and 20, or between 3 and 15, or between 4 and 20, or between 4 and 15, or between 4 and 10, or between 4 and 8 ring atoms.

In some variations of the reagent of formula (ii), $R^c$ and $R^d$ are taken together with the nitrogen atoms to which they are connected to form a cyclic moiety having at least 4, or at least 5, or between 3 and 20, or between 3 and 15, or between 4 and 20, or between 4 and 15, or between 4 and 10, or between 4 and 8 ring atoms.

In some variations of the reagent of formula (ii), $R^b$ and $R^d$ are taken together with the nitrogen atoms to which they are connected to form a cyclic moiety having at least 6, or at least 7, or between 6 and 20, or between 6 and 15, or between 7 and 20, or between 7 and 15, or between 7 and 10 ring atoms.

In some variations of the reagent of formula (ii), $R^a$ and $R^c$ are taken together with the nitrogen atoms to which they are connected to form a cyclic moiety having at least 6, or at least 7, or between 6 and 20, or between 6 and 15, or between 7 and 20, or between 7 and 15, or between 7 and 10 ring atoms.

In other embodiments, the reagent is a compound of formula (iii):

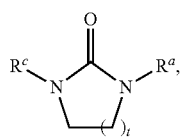

(iii)

wherein:

each $R^a$ and $R^c$ is independently H, aliphatic, aryl or heteroaryl; and t is an integer greater than or equal to 0, In some variations of the reagent of formula (iii), each $R^a$ and $R^c$ is independently H, alkyl, aryl, or heteroaryl. In certain variations, $R^a$ is alkyl. In one variation, $R^a$ is $C_{1-4}$ alkyl. In other variations, $R^c$ is H, alkyl, or aryl. In certain variations, $R^c$ is H, $C_{1-4}$ alkyl, or $C_{5-12}$ aryl. In one variation, $R^c$ is H, methyl, ethyl, or phenyl.

In some variations of the reagent of formula (iii), t is an integer greater than or equal to 1. In certain variations, t is an integer between 1 and 12, between 1 and 10, between 1 and 9, between 1 and 8, between 1 and 7, between 1 and 6, or 5, 4, 3, 2 or 1.

In some embodiments of the methods described herein, exemplary amide and urea reagents suitable for use in the methods provided herein include:

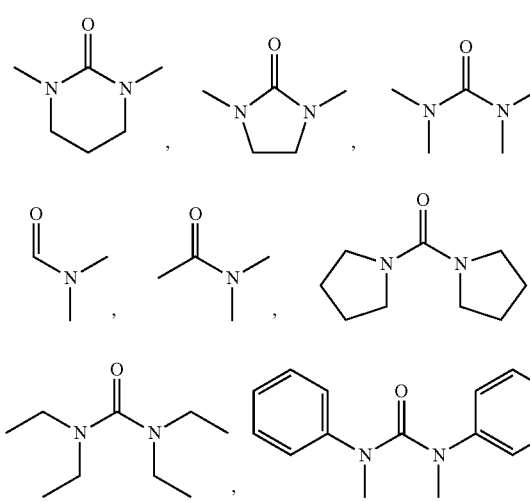

-continued

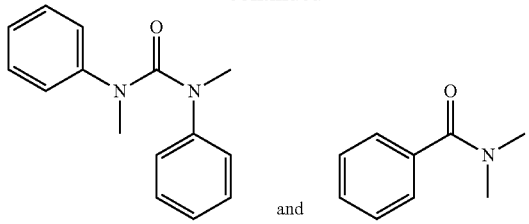

and

In other variations, the reagent is

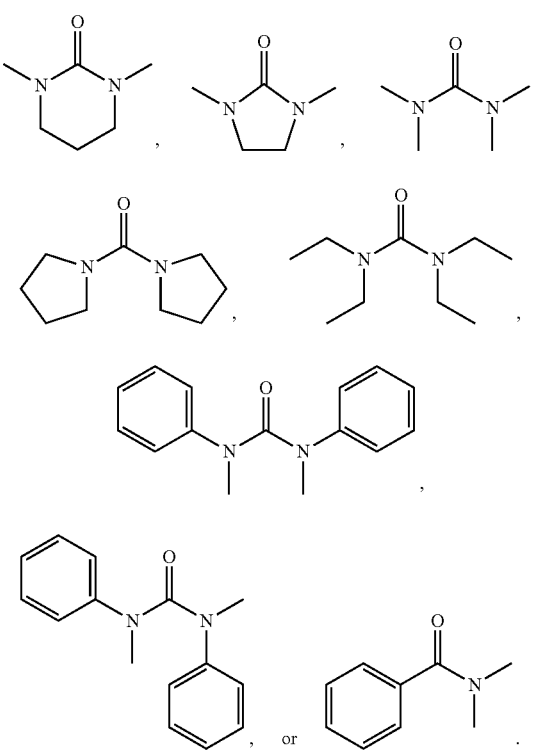

, or

In one variation, the reagent is:

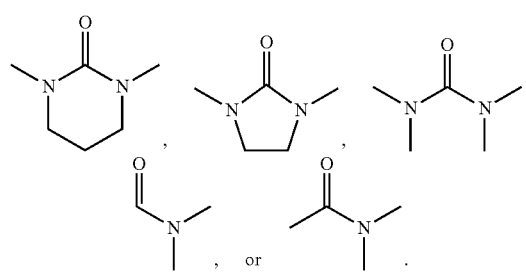

, or

In yet another variation, the reagent is:

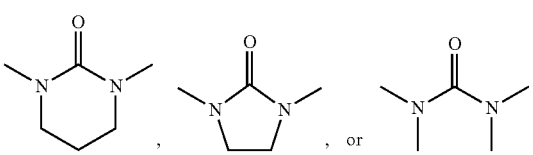

, or

In one variation, the reagent is

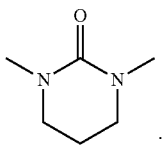

In another variation, the reagent is

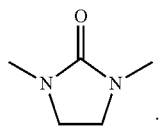

Any combination of the reagents described herein, including the reagents having the formula (i), (ii) and (iii), and the specific examples of reagents described above, may also be used.

Hydrogen

In some embodiments, the compound of formula (A") or (A) is reduced to produce the compound of formula (I"), (I'), (I), (I-a) or (I-b) in the presence of hydrogen. The hydrogen may be provided in the form of hydrogen gas or by transfer hydrogenation (e.g., by addition of cyclohexene or cyclohexadiene to the reaction mixture as the hydrogen source).

In certain variations, the compound of formula (A") or (A) is reduced to produce the compound of formula (I"), (I'), (I), (I-a) or (I-b) in the presence of hydrogen gas. In one variation, the compound of formula (A") or (A) is reduced at a pressure of at least 1 psi, or at least 10 psi; or between 1 psi and 1500 psi, between 1 psi and 1000 psi, between 500 psi to 1500 psi, between 1 psi and 50 psi, between 1 psi and 100 psi, between 1 psi and 80 psi, between 1 psi and 75 psi, or between 30 psi and 60 psi. It should be understood that the hydrogen gas may be dissolved, or at least partially dissolved, in the reagents and/or other solvents described herein.

In certain variations, the compound of formula (A") or (A) and the hydrogen (e.g., hydrogen gas) are present in a mass ratio between 1:2.9 and 1:3.8, or about 1:3.

Aromatic Reagent

In some embodiments of the methods described herein, the compound of formula (A") or (A) is converted to alkylfurans in the further presence of an aromatic reagent. Any of the aromatic reagents described herein may be used. As noted above, the reagents described herein may, under certain conditions, also act as a solvent. Any combinations or mixtures of the aromatic reagents described herein may also be used.

In some variations, the aromatic reagent is a mono-aryl compound, a di-aryl compound, or a tri-aryl compound. In certain variations, the aromatic reagent is toluene or xylene. In one variation, the aromatic reagent is para-xylene. In certain variations, the aromatic reagent is toluene or benzene.

In certain embodiments, the aromatic reagent is an alkyl phenyl solvent, such as a linear alkyl benzene. As used herein, "an alkyl phenyl reagent" refers to a class of reagents that have one or more alkyl chains attached to one or more phenyl or phenyl-containing ring systems. The alkyl phenyl reagent may be referred to as an alkylbenzene or a phenylalkane. One skilled in the art would recognize that certain phenylalkanes may also be interchangeably referred to as an alkylbenzene. For example, (1-phenyl)dodecane and dodecylbenzene refer to the same solvent.

In certain embodiments, the aromatic reagent is an alkylbenzene. Examples may include (monoalkyl)benzenes, (dialkyl)benzenes, and (polyalkyl)benzenes. In certain embodiments, the alkylbenzene has one alkyl chain attached to one benzene ring. The alkyl chain may have one or two points of attachment to the benzene ring. Examples of alkylbenzenes with one alkyl chain having one point of attachment to the benzene ring include dodecylbenzene. In embodiments where the alkyl chain has two points of attachment to the benzene ring, the alkyl chain may form a fused cycloalkyl ring to the benzene. Examples of alkylbenzenes with one alkyl having two points of attachment to the benzene ring include tetralin. It should be understood that the fused cycloalkyl ring may be further substituted with one or more alkyl chains.

In other embodiments, the alkylbenzene has two or more alkyl chains (e.g., 2, 3, 4, 5, or 6 alkyl chains) attached to one benzene ring.

In yet other embodiments, the alkylbenzene is an alkyl-substituted fused benzene ring system. The fused benzene ring system may include benzene fused with one or more heterocyclic rings. In one embodiment, the fused benzene ring system may be two or more fused benzene rings, such as naphthalene. The fused benzene ring system may be optionally substituted by one or more alkyl chains. For example, such alkyl-substituted fused benzene ring system may include tetramethylnaphthalene.

In some embodiments, the aromatic reagent is a phenylalkane. Examples may include (monophenyl)alkanes, (diphenyl)alkanes, and (polyphenyl)alkanes. In certain embodiments, the phenylalkane has one phenyl ring attached to one alkyl chain. In one embodiment, the alkyl chain attached to the phenyl ring may be an alkyl chain with at least eight carbons (e.g., $C_{8+}$ alkyls), such as a $C_{8-20}$ alkyl or a $C_{13-20}$ alkyl. The phenyl ring may be attached to any carbon along the alkyl chain. For example, the phenyl alkyl having one alkyl chain may be (1-phenyl)dodecane or (2-phenyl)dodecane.

In other embodiments, the phenylalkane has two or more phenyl rings attached to one alkyl chain. The alkyl phenyl solvents may be linear or branched, based on the alkyl chain(s) attached to the phenyl or phenyl-containing ring systems. Thus, the alkyl chain may be linear or branched. Linear alkyl chains may include, for example, n-propyl, n-butyl, n-hexyl, n-heptyl, n-octyl, n-nonanyl, n-decyl, n-undecyl, and n-dodecyl. Branched alkyl chains may include, for example, isopropyl, sec-butyl, isobutyl, tert-butyl, and neopentyl. In some embodiments where the solvent includes two or more alkyl chains, certain alkyl chains may be linear, whereas other alkyl chains may be branched. In other embodiments where the solvent includes two or more alkyl chains, all the alkyl chains may be linear or all the alkyl chains may be branched.

For example, the aromatic reagent is a linear alkylbenzene ("LAB"). Linear alkylbenzenes are a class of reagents having the formula $C_6H_5C_nH_{2n+1}$. For example, in one embodiment, the linear alkylbenzene is dodecylbenzene. Dodecylbenzene is commercially available, and may be "hard type" or "soft type". Hard type dodecylbenzene is a mixture of branched chain isomers. Soft type dodecylbenzene is a mixture of linear chain isomers. In one embodiment, the solvent includes hard type dodecylbenzene.

In some embodiments, the aromatic reagent is any of the alkyl phenyl solvents described above, in which the phenyl ring is substituted with one or more halogen atoms. In certain embodiments, the aromatic reagent is an alkyl(halobenzene). For example, the alkyl(halobenzene) may include alkyl(chlorobenzene). In one embodiment, the halo substituent for the phenyl ring may be, for example, chloro, bromo, or any combination thereof.

In some embodiments, the aromatic reagent is a $C_{6-20}$ aromatic reagent, or a $C_{6-15}$ aromatic reagent. In one embodiment, the aromatic reagent is naphthalene, naphthenic oil, alkylated naphthalene, diphenyl, a polychlorinated biphenyl, or a polycyclic aromatic hydrocarbon.

In certain embodiments, the aromatic reagent is an alkyl benzene. In one embodiment, the aromatic reagent is dodecylbenzene. An example of such dodecylbenzene is Marlican®. In other embodiments, the alkyl benzene may have alkyl side chains having at least 10 carbon atoms, at least 13 carbon atoms, or 10 to 40 carbon atoms, or 10 to 20 carbon atoms, or 10 to 13 carbon atoms, or 13 to 30 carbon atoms. Suitable alkyl benzenes may include, for example, Wibaryl® (e.g., benzene substituted with $C_{10-13}$ alkyl chain), Wibaryl® F (heavy alkylate), Wibaryl® A (diphenylalkanes, wherein the alkyl chains are $C_{10-13}$ alkyl chains), Wibaryl® B (dialkylbenzenes, wherein the alkyl chains are $C_{10-13}$ alkyl chains), Wibaryl® AB (a mixture of diphenylalkanes and dialkylbenzenes), Wibaryl® R (oligo- and polyalkylbenzenes), Cepsa Petrelab® 500-Q (linear alkylbenzene containing side alkyl chains of 10-13 carbon atoms), Cepsa Petrelab® 550-Q (linear alkylbenzene containing side alkyl chains of 10-13 carbon atoms), Cepsa Petrene® 900-Q (heavy alkylbenzene containing primarily dialkylbenzenes), Synnaph® AB 3 (heavy alkyl benzene), Synnaph® DAB4 (dialkylbenzene), and Therminol® 55 (benzene substituted with $C_{13-30}$ alkyl chains).

In other embodiments, the aromatic reagent is a phenyl ethers, including monophenyl ethers, diphenyl ethers and polyphenyl ethers. Suitable phenyl ethers include, for example, Santovac® 5 and Santovac® 7. In yet other embodiments, the aromatic reagent may include at least one alkyl chain substituent, and such aromatic reagents may include monocyclic aromatic ring system or bicyclic or polycyclic aromatic systems (including fused ring systems). Examples of such aromatic reagents include, for example, naphthalene, anthracene, Dowtherm® (mixture of biphenyl and diphenyl oxide), Dowtherm® G (di- and tri-aryl ethers), Dowtherm® Q (a mixture of diphenylethane and alkylated aromatics), and Dowtherm® MX (a mixture of alkylated aromatics).

In one variation, the aromatic reagent is toluene, benzene, xylene, or mesitylene.

As discussed above, any combinations or mixtures of such aromatic reagents may also be used.

In some embodiments of the methods described herein, an aromatic reagent is used with an amide reagent, or a urea reagent, or a combination thereof and hydrogen to produce alkylfurans. In certain variations, when an acidic or neutral solid support is used, an aromatic reagent is used with an amide reagent, or a urea reagent, or a combination thereof and hydrogen to produce alkylfurans. In certain variations, the amide or urea reagent and the aromatic reagent are present in a mass ratio of between 1:10 and 10:1, or between 1:9 and 3:1.

Solvent

In some embodiments, the compound of formula (A") or (A) is reduced to produce the compounds of formula (I"), (I'), (I), (I-a) or (I-b) in the presence of solvent. In some variations, a solvent is a component in a reaction mixture that can dissolve or partially dissolve one or more of the other reagents, including, for example, the compound of formula (A") or (A), the catalyst, and/or the amide reagent, or the urea reagent, or a combination thereof reagent. The solvents used may be obtained from any source, including any commercially available source. Any combinations or mixture of the solvents described herein may also be used.

In certain embodiments, the solvent includes organic solvent. In some variations, the solvents suitable for use in the methods provided herein may include, for example, aromatic solvents (including, for example, alkyl phenyl solvents), alkyl solvents, halogenated solvents, or any combinations or mixtures thereof.

Such solvents may have a boiling point or a boiling point range above the boiling point of the compound of formula I. It should be understood that a solvent may fall within one or more classes described above. For example, Wibaryl® A is an aromatic solvent that can more specifically be classified as an alkyl phenyl solvent.

In some embodiments, the solvent includes an aromatic solvent or a mixture of aromatic solvents. In some variations, the solvent includes at least one mono-aryl compound, at least one di-aryl compound, or at least one tri-aryl compound, or any mixtures thereof. In one variation, the solvent includes toluene or para-xylene.

In certain embodiments, the solvent may include one or more alkyl phenyl solvents, such as one or more linear alkyl benzenes. As used herein, "an alkyl phenyl solvent" refers to a class of solvents that have one or more alkyl chains attached to one or more phenyl or phenyl-containing ring systems. The alkyl phenyl solvent may be referred to as an alkylbenzene or a phenylalkane. One skilled in the art would recognize that certain phenylalkanes may also be interchangeably referred to as an alkylbenzene. For example, (1-phenyl)dodecane and dodecylbenzene refer to the same solvent.

In certain embodiments, the solvent includes one or more alkylbenzenes. Examples may include (monoalkyl)benzenes, (dialkyl)benzenes, and (polyalkyl)benzenes. In certain embodiments, the alkylbenzene has one alkyl chain attached to one benzene ring. The alkyl chain may have one or two points of attachment to the benzene ring. Examples of alkylbenzenes with one alkyl chain having one point of attachment to the benzene ring include dodecylbenzene. In embodiments where the alkyl chain has two points of attachment to the benzene ring, the alkyl chain may form a fused cycloalkyl ring to the benzene. Examples of alkylbenzenes with one alkyl having two points of attachment to the benzene ring include tetralin. It should be understood that the fused cycloalkyl ring may be further substituted with one or more alkyl chains.

In other embodiments, the alkylbenzene has two or more alkyl chains (e.g., 2, 3, 4, 5, or 6 alkyl chains) attached to one benzene ring.

In yet other embodiments, the alkylbenzene is an alkyl-substituted fused benzene ring system. The fused benzene ring system may include benzene fused with one or more heterocyclic rings. In one embodiment, the fused benzene ring system may be two or more fused benzene rings, such as naphthalene. The fused benzene ring system may be optionally substituted by one or more alkyl chains. For example, such alkyl-substituted fused benzene ring system may include tetramethylnaphthalene.

In some embodiments, the solvent includes phenylalkane. Examples may include (monophenyl)alkanes, (diphenyl)alkanes, and (polyphenyl)alkanes. In certain embodiments, the phenylalkane has one phenyl ring attached to one alkyl chain. In one embodiment, the alkyl chain attached to the phenyl ring may be an alkyl chain with at least eight carbons (e.g., $C_{8+}$ alkyls), such as a $C_{8-20}$ alkyl or a $C_{13-20}$ alkyl. The phenyl ring may be attached to any carbon along the alkyl chain. For example, the phenyl alkyl having one alkyl chain may be (1-phenyl)dodecane or (2-phenyl)dodecane.

In other embodiments, the phenylalkane has two or more phenyl rings attached to one alkyl chain. The alkyl phenyl solvents may be linear or branched, based on the alkyl chain(s) attached to the phenyl or phenyl-containing ring systems. Thus, the alkyl chain may be linear or branched. Linear alkyl chains may include, for example, n-propyl, n-butyl, n-hexyl, n-heptyl, n-octyl, n-nonanyl, n-decyl, n-undecyl, and n-dodecyl. Branched alkyl chains may include, for example, isopropyl, sec-butyl, isobutyl, tert-butyl, and neopentyl. In some embodiments where the solvent includes two or more alkyl chains, certain alkyl chains may be linear, whereas other alkyl chains may be branched. In other embodiments where the solvent includes two or more alkyl chains, all the alkyl chains may be linear or all the alkyl chains may be branched.

For example, the solvent may include one or more linear alkylbenzenes ("LABs"). Linear alkylbenzenes are a class of solvents having the formula $C_6H_5C_nH_{2n+1}$. For example, in one embodiment, the linear alkylbenzene is dodecylbenzene. Dodecylbenzene is commercially available, and may be "hard type" or "soft type". Hard type dodecylbenzene is a mixture of branched chain isomers. Soft type dodecylbenzene is a mixture of linear chain isomers. In one embodiment, the solvent includes hard type dodecylbenzene.

In some embodiments, the solvent may include any of the alkyl phenyl solvents described above, in which the phenyl ring is substituted with one or more halogen atoms. In certain embodiments, the solvent includes an alkyl(halobenzene). For example, the alkyl(halobenzene) may include alkyl(chlorobenzene). In one embodiment, the halo substituent for the phenyl ring may be, for example, chloro, bromo, or any combination thereof.

In some embodiments, the solvent may include one or more heavy alkanes. "Heavy alkanes" include saturated hydrocarbon chains containing at least 8 carbon atoms (e.g., $C_{8+}$ alkane), at least 10 carbon atoms (e.g., $C_{10+}$ alkane), or at least 13 carbon atoms (e.g., $C_{13+}$ alkane). In some embodiments, the heavy alkane may have 8 to 100 carbon atoms (e.g., $C_{8-100}$ alkanes), 8 to 50 carbon atoms (e.g., $C_{8-50}$ alkanes), 8 to 25 carbon atoms (e.g., $C_{8-25}$ alkanes), or 10 to 20 carbon atoms (e.g., $C_{10-20}$ alkanes). In other embodiments, the solvent may include one or more heavy alkanes, wherein at least one heavy alkane has at least 13 carbon atoms. In one embodiment, the solvent may include hexadecane, heptadecane, octadecane, icosane, heneicosane, docosane, tricosane, tetracosane, or any combinations or mixtures thereof.

In other embodiments, the solvent may include one or more esters. In some embodiments, the esters may be fatty acids. In certain embodiments, the esters may be (heavy alkyl)-esters, e.g., $C_{8+}$ alkyl-(O)OH. In some embodiments, the (heavy alkyl)-esters may have 8 to 100 carbon atoms (e.g., $C_{8-100}$ alkyl-(O)OH), 8 to 50 carbon atoms (e.g., $C_{8-50}$ alkyl-(O)OH), 8 to 25 carbon atoms (e.g., $C_{8-25}$ alkyl-(O)OH), or 10 to 20 carbon atoms (e.g., $C_{10-20}$ alkyl-(O)OH). In one embodiment, the solvent may include hexadecanoic acid.

In other embodiments, the solvent may include one or more aromatic solvents. In some embodiments, the aromatic solvent is a $C_{6-20}$ aromatic solvent, or a $C_{6-15}$ aromatic solvent. In one embodiment, the solvent includes naphthalene, naphthenic oil, alkylated naphthalene, diphenyl, poly-chlorinated biphenyls, polycyclic aromatic hydrocarbons, or any combinations or mixtures thereof.

In yet other embodiments, the solvent may include one or more silicone oils. In certain embodiments, the solvent includes one or more alkyl siloxanes.

The solvent may be a single solvent or may include a mixture of solvents. If the solvent is a mixture of solvents, the solvent mixture has a boiling point at or above the boiling point of the 5-(halomethyl)furfural at the operating pressure. For example, in some embodiments, the solvent may be a mixture of (i) one or more alkyl phenyl solvents, and (ii) one or more aromatic solvents. For example, in another embodiment, the solvent may be a mixture of toluene and one or more other solvents such as camphor, anthracene, and anthraquinone. It should be understood that if the solvent mixture has a range of boiling points, such range may encompass the boiling point of the 5-(halomethyl)furfural at the operating pressure but the entire range need not be above the boiling point of the 5-(halomethyl)furfural at the operating pressure.

It should also be understood that the solvent may include any substance that is a liquid at the operating temperature and pressure, but such substance may not be a liquid at standard temperature and pressure.

Exemplary solvents that may be used in the methods and compositions described herein include alkyl benzenes, sulfolane, heavy alkanes, diphenyl ethers and polyphenyl ethers, and other aromatic solvents. In certain embodiments, the solvent includes alkyl benzenes. In one embodiment, the solvent includes dodecylbenzene. An example of such dodecylbenzene is Marlican®. In other embodiments, the alkyl benzene may have alkyl side chains having at least 10 carbon atoms, at least 13 carbon atoms, or 10 to 40 carbon atoms, or 10 to 20 carbon atoms, or 10 to 13 carbon atoms, or 13 to 30 carbon atoms. Suitable alkyl benzenes may include, for example, Wibaryl® (e.g., benzene substituted with $C_{10-13}$ alkyl chain), Wibaryl® F (heavy alkylate), Wibaryl® A (diphenylalkanes, wherein the alkyl chains are $C_{10-13}$ alkyl chains), Wibaryl® B (dialkylbenzenes, wherein the alkyl chains are $C_{10-13}$ alkyl chains), Wibaryl® AB (a mixture of diphenylalkanes and dialkylbenzenes), Wibaryl® R (oligo- and polyalkylbenzenes), Cepsa Petrelab® 500-Q (linear alkylbenzene containing side alkyl chains of 10-13 carbon atoms), Cepsa Petrelab® 550-Q (linear alkylbenzene containing side alkyl chains of 10-13 carbon atoms), Cepsa Petrene® 900-Q (heavy alkylbenzene containing primarily dialkylbenzenes), Synnaph® AB 3 (heavy alkyl benzene), Synnaph® DAB4 (dialkylbenzene), and Therminol® 55 (benzene substituted with $C_{13-30}$ alkyl chains).

In other embodiments, the solvent includes phenyl ethers, including monophenyl ethers, diphenyl ethers and polyphenyl ethers. Suitable phenyl ethers include, for example, Santovac® 5 and Santovac® 7. In yet other embodiments, the solvent includes other aromatic solvents. The aromatic solvent may include at least one alkyl chain substituent, and such aromatic solvents may include monocyclic aromatic ring system or bicyclic or polycyclic aromatic systems (including fused ring systems). Examples of such aromatic solvents include, for example, naphthalene, anthracene, Dowtherm® (mixture of biphenyl and diphenyl oxide), Dowtherm® G (di- and tri-aryl ethers), Dowtherm® Q (a mixture of diphenylethane and alkylated aromatics), and Dowtherm® MX (a mixture of alkylated aromatics). As discussed above, any combinations or mixtures of such solvents may also be used.

In other embodiments, as discussed above, the reagents of formula (i), (ii) and (iii), or any combinations thereof, may act as a solvent. Thus, in one variation, no additional solvent is added where the reagents of formula (i), (ii) and (iii), or any combinations thereof, are used. In another variation, the compound of formula (A″) or (A) is reduced to produce the compound of formula (I″), (I′), (I), (I-a) or (I-b) in the presence of a reagent of formula (i), (ii) or (iii), or any combinations thereof, and any of the other solvents described herein.

Reaction Conditions

The operating temperature refers to the average temperature of the reaction mixture in the vessel. In some embodiments, the operating temperature may be at least 10° C., at least 15° C., at least 25° C., at least 100° C., or at least 150° C.; or between 0° C. and 250° C., between 0° C. and 200° C., between 0° C. and 150° C., between 0° C. and 100° C., between 5° C. and 80° C., or between 10° C. and 75° C., between 15° C. and 65° C., or between 130° C. and 250° C.

In some variations, the operating temperature is less than 50° C. or less than 45° C.; or between −20° C. and 45° C., between −10° C. and 45° C., between 0° C. and 45° C., between 10° C. and 45° C., between 20° C. and 45° C., or between 30° C. and 45° C.

The operating pressure refers to the average absolute internal pressure of the vessel. In some embodiments, the operating pressure may be at least 1 psi, or at least 10 psi; or between 1 psi and 1500 psi, between 1 psi and 1000 psi, between 500 psi to 1500 psi, between 1 psi and 50 psi, between 1 psi and 100 psi, between 1 psi and 80 psi, between 1 psi and 75 psi, or between 30 psi and 60 psi.

In some variations, the operating temperature is between 0.1 psia and 100 psia, between 0.1 psia and 1000 psia, between 10 psia and 100 psia, or between 20 psia and 70 psia; or about 65 psia.

It should be understood that temperature may be expressed as degrees Celsius (° C.) or Kelvin (K). One of ordinary skill in the art would be able to convert the temperature described herein from one unit to another. Pressure may also be expressed as gauge pressure (barg), which refers to the pressure in bars above ambient or atmospheric pressure. Pressure may also be expressed as bar, atmosphere (atm), pascal (Pa) or pound-force per square inch (psi). It should further be understood that pressure may also be expressed as pounds per square in absolute (psia). One of ordinary skill in the art would be able to convert the pressure described herein from one unit to another.

The method (e.g., the reduction of the compounds of formulae (A″), (A), (A-i) and (A-ii) to the compounds of formulae (I″), (I′), (I), (I-a) and (I-b), as applicable) may be performed with or without stirring. In certain embodiments, the method (e.g., the reduction of the compounds of formulae (A″), (A), (A-i) and (A-ii) to the compounds of formulae (I″), (I′), (I), (I-a) and (I-b), as applicable, is performed with stirring to increase conversion and/or selectivity.

Additionally, the methods described herein may be carried out batch-wise or continuously. The reaction time (in a batch-wise process) or residence time (in a continuous process) will also vary with the reaction conditions and desired yield, but is generally about 1 to 72 hours. In some of the foregoing embodiments, the reaction time or residence time is determined by the rate of conversion of the starting material. In some of the foregoing embodiments, the reaction mixture is reacted for 1 to 24 hours. In some of the foregoing embodiments, the reaction mixture is reacted for 1 to 10 hours. In some of the foregoing embodiments, the reaction mixture is reacted for 1 to 5 hours. In some of the foregoing embodiments, the reaction mixture is reacted for 1 to 3 hours. In some of the foregoing embodiments, the reaction mixture is reacted for less than 2 hours, less than 1 hour, less than 30 minutes, less than 10 minutes, or less than 5 minutes.

Isolation and Purification

The methods described herein may further include isolating and/or purifying the alkylfurans, e.g., the compounds of formula (I″), (I′), (I), (I-a) and (I-b), from the reaction mixture. Any methods known in the art may be employed to isolate and/or purify the alkylfurans. For example, the alkylfurans, e.g., the compounds of formula (I″), (I′), (I), (I-a) and (I-b), may be isolated and/or purified by distillation. In another example, the alkylfurans, e.g., the compounds of formula (I″), (I′), (I), (I-a) and (I-b), may be isolated by distillation, and the isolated alkylfuran may be further purified by chromatography.

It should be understood that in certain variations, the alkylfuran produced is not isolated and/or purified, and may be further used in one or more downstream reactions described herein (e.g., to produce para-xylene and/or terephthalic acid).

Yield, Conversion and Selectivity

The yield of a product takes into account the conversion of the starting materials into the product, and the selectivity for the product over other products that may be formed.

The difference between yield, conversion and selectivity is explained in the examples provided below. For example, with respect to the conversion of a compound of formula (A″) or (A) into a compound of formula (I″), (I′), (I), (I-a) or (I-b), the reaction can be generalized as follows, where "A" represents the moles of the compound of formula (A″) or (A); and "C" represents the moles of the compound of formula (I″), (I′), (I), (I-a) or (I-b); and "a" and "c" are stoichiometric coefficients.

$$aA \rightarrow cC$$

Conversion of A is the percentage of reactant A that has been consumed during the reaction shown above, as expressed by the following equation:

$$\% \text{ Conversion} = \frac{Ao - Af}{Ao} * 100\%,$$

where $A_o$ is the initial number of moles of reactant A; and $A_f$ is the final number of moles of reactant A.

Selectivity is the stoichiometrically relative amount of product C produced from the converted amount of reactant A, as expressed as a percentage by the following equation:

$$\text{Selectivity}(\%) = \frac{Cf * \frac{a}{c}}{Ao - Af} * 100\%,$$

where $A_o$ is the starting moles of reactant A; $A_f$ is the final number of moles of reactant A; and $C_f$ is the number of moles of product C. In some embodiments where "a/c"=1, and the equation can be simplified to:

$$\text{Selectivity}(\%) = \frac{Cf}{Ao - Af} * 100\%.$$

The yield of product C is the percentage of reactant A that is converted into product C, as expressed by the following equation:

Yield (%)=Conversion (%)*Selectivity (%)

In certain embodiments, the methods described herein have a yield of at least 10%, at least 15%, at least 20%, at least 30%, at least 40%, at least 50%, at least 60%, at least 70%, at least 75%, at least 80%, at least 85%, at least 90%, at least 95%, or at least 99% by weight. In other embodiments, the yield is between 10% to 100%, between 10% to 90%, between 15% to 100%, between 15% to 90%, between 20% to 80%, between 30% to 80%, between 40% to 80%, between 50%-80%, or between 60%-80% by weight.

In certain embodiments, the methods described herein have a selectivity of at least 10%, at least 20%, at least 30%, at least 40%, at least 50%, at least 60%, at least 70%, at least 80%, at least 90%, or at least 99%. In other embodiments, the selectivity is between 40% to 99%, between 40% to 95%, between 40% to 90%, between 40% to 80%, between 50% to 99%, between 50% to 95%, between 50% to 90%, between 50% to 80%, between 60% to 99%, between 60% to 95%, between 60% to 90%, between 60% to 80%, between 70% to 99%, between 70% to 95%, between 70% to 90%, or between 70% to 80%.

It should be understood that the choice of catalysts, reagents and solvents, and reaction conditions can impact the yield, conversion and selectivity of the methods described herein. For example, in some variations, when the method is conducted at an operating temperature between 35° C. and 45° C., (i) the yield of alkylfurans produced is at least 85%, (ii) the selectivity of alkylfurans produced is at least 85%, or both (i) and (ii).

Downstream Products

The compounds of formula (I″), (I′), (I), (I-a) and (I-b), including, for example, 2,5-dimethylfuran and 2-methylfuran, produced according to the methods described herein may be suitable for manufacture of one or more plastics, fuels (e.g., transportation fuels) or other compounds. For example, 2,5-dimethylfuran may be converted to para-xylene. See e.g., U.S. 2013/0245316.

Thus, in some aspects, provided is a method of producing para-xylene, by combining 2,5-dimethylfuran produced according to any of the methods described herein and ethylene to produce para-xylene. In other aspects, provided is a method of producing terephthalic acid by: combining 2,5-dimethylfuran produced according to any of the methods described herein and ethylene to produce para-xylene; and oxidizing the para-xylene to terephthalic acid. In yet other aspects, provided is a method of producing polyethylene terephthalate by: combining 2,5-dimethylfuran produced according to any of the methods described herein and ethylene to produce para-xylene; oxidizing the para-xylene to terephthalic acid; and polymerizing terephthalic acid with ethylene glycol to yield polyethylene terephthalate using any methods known in the art.

Compositions

Provided herein are also compositions that include any of the compounds of formula (A″) or (A), catalysts, hydrogen, amide and/or urea reagents and other reagents or solvents described herein. In some embodiments, the compositions may also include any of the acids and/or solvents described herein.

Any of the compounds of formula (A″) or (A), solid-supported metal catalysts and amide or urea reagents described herein may be present in a composition. For example, in some aspects, provided is a composition that includes:

a compound of formula (A):

$$R^{1a}\!\!-\!\!\underset{\text{O}}{\diagdown\!\!\diagup}\!\!-\!\!R^{2a},\quad (A)$$

wherein:
$R^{1a}$ is $C_m$ alkyl, $-(CH_2)_m Y$, $-(CH_2)_{m-1}CH(O)$ or $-(CH_2)_m OH$ wherein:
  m is an integer greater than or equal to 0, provided that when m is 0, $R^{1a}$ is H; and
  Y is halo; and
$R^{2a}$ is $-(CH_2)_{n-1}CH(O)$, $-(CH_2)_n OH$, or $-(CH_2)_n X$, wherein:
  n is an integer greater than or equal to 1; and
  X is halo;
hydrogen; and
a solid-supported metal catalyst comprising a metal component and a basic solid support; and
optionally an amide reagent, or a urea reagent, or a combination thereof.

In some variations, the basic solid support is a solid support that (i) has more basic sites than acidic sites and (ii) chemisorbs at least 0.001 g carbon dioxide/g solid support. In some variations, the basic solid support chemisorbs at least 0.005 g carbon dioxide/g solid support, at least 0.01 g carbon dioxide/g solid support, at least 0.05 g carbon dioxide/g solid support, at least 0.1 g carbon dioxide/g solid support, at least 0.2 g carbon dioxide/g solid support, at least 0.25 g carbon dioxide/g solid support, at least 0.3 g carbon dioxide/g solid support, at least 0.35 g carbon dioxide/g solid support, at least 0.4 g carbon dioxide/g solid support, at least 0.45 g carbon dioxide/g solid support, at least 0.5 g carbon dioxide/g solid support, at least 0.55 g carbon dioxide/g solid support, at least 0.6 g carbon dioxide/g solid support, at least 0.65 g carbon dioxide/g solid support, or at least 0.7 g carbon dioxide/g solid support; or between 0.005 g carbon dioxide/g solid support and 0.75 g carbon dioxide/g solid support, between 0.001 g carbon dioxide/g solid support and 0.75 g carbon dioxide/g solid support, between 0.01 g carbon dioxide/g solid support and 0.75 g carbon dioxide/g solid support, between 0.1 g carbon dioxide/g solid support and 0.75 g carbon dioxide/g solid support, between 0.15 g carbon dioxide/g solid support and 0.75 g carbon dioxide/g solid support, between 0.2 g carbon dioxide/g solid support and 0.75 g carbon dioxide/g solid support, between 0.25 g carbon dioxide/g solid support and 0.75 g carbon dioxide/g solid support, between 0.3 g carbon dioxide/g solid support and 0.75 g carbon dioxide/g solid support, between 0.35 g carbon dioxide/g solid support and 0.75 g carbon dioxide/g solid support, between 0.4 g carbon dioxide/g solid support and 0.75 g carbon dioxide/g solid support, between 0.45 g carbon dioxide/g solid support and 0.75 g carbon dioxide/g solid support, between 0.5 g carbon dioxide/g solid support and 0.75 g carbon dioxide/g solid support, between 0.55 g carbon dioxide/g solid support and 0.75 g carbon dioxide/g solid support, between 0.6 g carbon dioxide/g solid support and 0.75 g carbon dioxide/g solid support, between 0.65 g carbon dioxide/g solid support and 0.75 g carbon dioxide/g solid support, between 0.005 g carbon dioxide/g solid support and 0.7 g carbon dioxide/g solid support, between 0.005 g carbon dioxide/g solid support and 0.65 g carbon dioxide/g solid support, between 0.005 g carbon dioxide/g solid support and 0.6 g carbon dioxide/g solid support, between 0.005 g carbon dioxide/g solid support and 0.55 g carbon dioxide/g solid support, between 0.005 g carbon dioxide/g solid support and 0.5 g carbon dioxide/g solid support, between 0.005 g carbon dioxide/g solid support and 0.45 g carbon dioxide/g solid support, between 0.005 g carbon dioxide/g solid support and 0.4 g carbon dioxide/g solid support, between 0.005 g carbon dioxide/g solid support and 0.35 g carbon dioxide/g solid support, between 0.005 g carbon dioxide/g solid support and 0.3 g carbon dioxide/g solid support, between 0.005 g carbon dioxide/g solid support and 0.25 g carbon dioxide/g solid support, between 0.005 g carbon dioxide/g solid support and 0.2 g carbon dioxide/g solid support, between 0.005 g carbon dioxide/g solid support and 0.15 g carbon dioxide/g solid support, between 0.005 g carbon dioxide/g solid support and 0.1 g carbon dioxide/g solid support, between 0.005 g carbon dioxide/g solid support and 0.01 g carbon dioxide/g solid support, or between 0.25 g carbon dioxide/g solid support and 0.5 g carbon dioxide/g solid support.

In some variations, the number of acidic sites of the basic solid support may be at least 2-fold, at least 5-fold, at least 10-fold, at least 50-fold, at least 100-fold, at least 150-fold, or at least 200-fold, or between 100-fold and 500-fold, between 100-fold and 250-fold than the number of basic sites.

In some variations, the basic solid support includes a metal oxide. In certain variations, the basic solid support includes a basic metal oxide. In certain variations, a basic metal oxide is a metal oxide that has more basic sites than acidic sites. In some variations, the number of acidic sites of the basic metal oxide may be at least 2-fold, at least 5-fold, at least 10-fold, at least 50-fold, at least 100-fold, at least 150-fold, or at least 200-fold, or between 100-fold and 500-fold, between 100-fold and 250-fold lower than the number of basic sites. It should generally be understood that the basicity of the metal oxide refers to the overall basicity of the metal oxide.

In other variations, the basic solid support includes an alkali earth metal oxide.

In some embodiments, the metal oxides that make up the basic solid support are selected from BeO, MgO, CaO, SrO, BaO, ZnO, $Al_2O_3$, $Y_2O_3$, $La_2O_3$, $CeO_2$, $ThO_2$, $TiO_2$, $ZrO_2$ and $SnO_2$. In certain embodiments, the metal oxides that make up the basic solid support are selected from BeO, MgO, CaO, SrO, BaO, $Y_2O_3$, and $La_2O_3$. In one variation, the metal oxide is MgO.

In other variations, the basic solid support includes a mixed metal oxide. In some embodiments, the mixed metal oxides in the basic solid support are selected from $SiO_2$—MgO, $SiO_2$—CaO, $SiO_2$—SrO, $SiO_2$—BaO, $SiO_2$—ZnO, $SiO_2$—$Al_2O_3$, $SiO_2$—$ThO_2$, $SiO_2$—$TiO_2$, $SiO_2$—ZrO, $SiO_2$—$MoO_3$, $SiO_2$—$WO_3$, $Al_2O_3$—MgO, $Al_2O_3$—$ThO_2$, $Al_2O_3$—$TiO_2$, $Al_2O_3$—$ZrO_2$, $Al_2O_3$—$Mn_2O_3$, $Al_2O_3$—$WO_3$, $ZrO_2$—ZnO, $ZrO_2$—$TiO_2$, and $TiO_2$—MgO.

Any combinations of the metal oxides and mixed metal oxides described herein may be included in the basic solid support.

In other variations, the basic solid support is a base-modified solid support as described herein. In certain variations, an acidic solid support or a neutral solid support may be modified to make the solid support basic in nature.

In one variation, the solid-supported metal catalyst in the composition is Pd+Pt/MgO, Pd+Au/MgO, or Pd/MgO. Any combinations of such solid-supported metal catalysts may also be used in the compositions described herein.

In other aspects, provided is a composition that includes: a compound of formula (A):

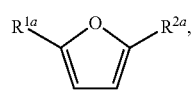

(A)

wherein:
$R^{1a}$ is $C_m$ alkyl, —$(CH_2)_m Y$, —$(CH_2)_{m-1}CH(O)$ or —$(CH_2)_m OH$ wherein:

m is an integer greater than or equal to 0, provided that when m is 0, $R^{1a}$ is H; and
Y is halo; and
$R^{2a}$ is —$(CH_2)_{n-1}CH(O)$, —$(CH_2)_n OH$, or —$(CH_2)_n X$, wherein:
n is an integer greater than or equal to 1; and
X is halo;
hydrogen;
a catalyst comprising a metal component and an acidic solid support; and
an amide reagent, or a urea reagent, or a combination thereof.

In some embodiments, the acidic solid support is a solid support that (i) has more acidic sites than basic sites, and (ii) chemisorbs at least 0.001 g ammonia/g solid support. In some variations, the acidic solid support chemisorbs at least 0.002 g ammonia/g solid support, at least 0.003 g ammonia/g solid support, at least 0.004 g ammonia/g solid support, at least 0.005 g ammonia/g solid support, at least 0.001 g ammonia/g solid support, at least 0.05 g ammonia/g solid support, at least 0.01 g ammonia/g solid support, at least 0.1 g ammonia/g solid support, at least 0.2 g ammonia/g solid support, at least 0.25 g ammonia/g solid support, at least 0.3 g ammonia/g solid support, at least 0.35 g ammonia/g solid support, at least 0.4 g ammonia/g solid support, at least 0.45 g ammonia/g solid support, or at least 0.5 g ammonia/g solid support; or between 0.001 g ammonia/g solid support and 0.5 g ammonia/g solid support, between 0.002 g ammonia/g solid support and 0.5 g ammonia/g solid support, between 0.003 g ammonia/g solid support and 0.5 g ammonia/g solid support, between 0.004 g ammonia/g solid support and 0.5 g ammonia/g solid support, between 0.005 g ammonia/g solid support and 0.5 g ammonia/g solid support, between 0.006 g ammonia/g solid support and 0.5 g ammonia/g solid support, between 0.007 g ammonia/g solid support and 0.5 g ammonia/g solid support, between 0.008 g ammonia/g solid support and 0.5 g ammonia/g solid support, between 0.009 g ammonia/g solid support and 0.5 g ammonia/g solid support, between 0.01 g ammonia/g solid support and 0.5 g ammonia/g solid support, between 0.05 g ammonia/g solid support and 0.5 g ammonia/g solid support, between 0.1 g ammonia/g solid support and 0.5 g ammonia/g solid support, between 0.2 g ammonia/g solid support and 0.5 g ammonia/g solid support, between 0.3 g ammonia/g solid support and 0.5 g ammonia/g solid support, between 0.4 g ammonia/g solid support and 0.5 g ammonia/g solid support, between 0.1 g ammonia/g solid support and 0.3 g ammonia/g solid support, between 0.2 g ammonia/g solid support and 0.25 g ammonia/g solid support, or between 0.25 g ammonia/g solid support and 0.5 g ammonia/g solid support.

In some variations, the number of basic sites of the acidic solid support may be at least 2-fold, at least 5-fold, at least 10-fold, at least 50-fold, at least 100-fold, at least 150-fold, or at least 200-fold, or between 100-fold and 500-fold, between 100-fold and 250-fold lower than the number of acidic sites.

In some variations, the acidic solid support includes a metal oxide. In certain variations, the acidic solid support includes an acidic metal oxide. In certain variations, an acidic metal oxide is a metal oxide that has more acidic sites than basic sites. In some variations, the number of basic sites of the acidic metal oxide may be at least 2-fold, at least 5-fold, at least 10-fold, at least 50-fold, at least 100-fold, at least 150-fold, or at least 200-fold, or between 100-fold and 500-fold, between 100-fold and 250-fold lower than the number of acidic sites. It should generally be understood that the acidity of the metal oxide refers to the overall acidity of the metal oxide.

In some embodiments, the metal oxides in the acidic solid support are selected from $SiO_2$, $ZnO$, $CdO$, $Al_2O_3$, $CeO_2$, $ThO_2$, $TiO_2$, $ZrO_2$, $SnO_2$, $PbO$, $As_2O_3$, $Bi_2O_3$, $Sb_2O_5$, $V_2O_5$, $Cr_2O_3$, $MoO_3$ and $WO_3$. In one variation, the metal oxide is $SiO_2$. In another variation, the metal oxide is $Al_2O_3$.

In other variations, the acidic solid support includes a mixed metal oxide. In some embodiments, the mixed metal oxides in the acidic solid support are selected from $SiO_2$—$Al_2O_3$, $SiO_2$—$TiO_2$, $SiO_2$—$SnO_2$, $SiO_2$—$ZrO_2$, $SiO_2$—$BeO$, $SiO_2$—$MgO$, $SiO_2$—$CaO$, $SiO_2$—$SrO$, $SiO_2$—$ZnO$, $SiO_2$—$Ga_2O_3$, $SiO_2$—$YrO_3$, $Si$—$O_2$—$La_2O_3$, $SiO_2$—$MoO_3$, $SiO_2$—$WO_3$, $SiO_2$—$V_2O_5$, $SiO_2$—$ThO_2$, $Al_2O_3$—$MgO$, $Al_2O_3$—$ZnO$, $Al_2O_3$—$CdO$, $Al_2O_3$—$B_2O_3$, $Al_2O_3$—$ThO_2$, $Al_2O_3$—$TiO_2$, $Al_2O_3$—$ZrO_2$, $Al_2O_3$—$V_2O_5$, $Al_2O_3$—$MoO_3$, $Al_2O_3$—$WO_3$, $Al_2O_3$—$Cr_2O_3$, $Al_2O_3$—$Mn_2O_3$, $Al_2O_3$—$Fe_2O_3$, $Al_2O_3$—$Co_3O_4$, $Al_2O_3$—$NiO$, $TiO_2$—$CuO$, $TiO_2$—$MgO$, $TiO_2$—$ZnO$, $TiO_2$—$CdO$, $TiO_2$—$ZrO_2$, $TiO_2$—$SnO_2$, $TiO_2$—$Bi_2O_3$, $TiO_2$—$Sb_2O_5$, $TiO_2$—$V_2O_5$, $TiO_2$—$Cr_2O_3$, $TiO_2$—$MoO_3$, $TiO_2$—$WO_3$, $TiO_2$—$Mn_2O_3$, $TiO_2$—$Fe_2O_3$, $TiO_2$—$Co_3O_4$, $TiO_2$—$NiO$, $ZrO_2$—$CdO$, $ZnO$—$MgO$, $ZnO$—$Fe_2O_3$, $MoO_3$—$CoO$—$Al_2O_3$, $MoO_3$—$NiO$—$Al_2O_3$, $TiO_2$—$SiO_2$—$MgO$, and $MoO_3$—$Al_2O_3$—$MgO$. Any combinations of the metal oxides and mixed metal oxides described herein may be included in the acidic solid support.

In yet other variations, the acidic solid support includes a zeolite. For example, such zeolites may include ZSM5 and Beta zeolite.

In other variations, the acidic solid support is an acid-modified solid support. A solid support may be modified to make the solid support acidic in nature.

In one variation, the solid-supported metal catalyst in the composition is $Pd/Al_2O_3$; $Pd/ZSM5$; $Pd/Beta$ zeolite; $Pd+Au/Al_2O_3$; $Pd+Ag/Al_2O_3$; or $Pd+Cu/Al_2O_3$. In one variation, the solid-supported metal catalyst is $Pd/Al_2O_3$. Any combinations of such solid-supported metal catalysts may also be used in the compositions described herein.

In some embodiments, the composition further includes an aromatic reagent. Any of the aromatic reagents described herein may be included. In one variation, the aromatic reagent is toluene, benzene, xylene, or mesitylene, or any combinations thereof. In other variations, the amide or urea reagent and the aromatic reagent are present in a mass ratio of between 1:10 and 10:1, or between 1:9 and 3:1.

In yet other aspects, provided is a composition that includes:
a compound of formula (A):

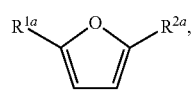

wherein:
$R^{1a}$ is $C_m$ alkyl, —$(CH_2)_mY$, —$(CH_2)_{m-1}CH(O)$ or —$(CH_2)_mOH$ wherein:
m is an integer greater than or equal to 0, provided that when m is 0, $R^{1a}$ is H; and
Y is halo; and
$R^{2a}$ is —$(CH_2)_{n-1}CH(O)$, —$(CH_2)_nOH$, or —$(CH_2)_nX$, wherein:
n is an integer greater than or equal to 1; and
X is halo;
hydrogen;
a catalyst comprising a metal component and a solid support; and an amide reagent, or a urea reagent, or a combination thereof,
wherein the composition is acidic.

The composition may be acidic due to the presence of an acidic solid support in the catalyst. Any of the acidic solid supports described herein may be present.

In other variations, the composition may be acidic due to the presence of acid. Thus, in yet another aspects, provided is a composition that includes:
a compound of formula (A):

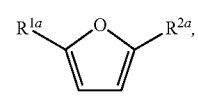

wherein:
$R^{1a}$ is $C_m$ alkyl, —$(CH_2)_mY$, —$(CH_2)_{m-1}CH(O)$ or —$(CH_2)_mOH$ wherein:
m is an integer greater than or equal to 0, provided that when m is 0, $R^{1a}$ is H; and
Y is halo; and
$R^{2a}$ is —$(CH_2)_{n-1}CH(O)$, —$(CH_2)_nOH$, or —$(CH_2)_nX$, wherein:
n is an integer greater than or equal to 1; and
X is halo;
hydrogen;
a catalyst comprising a metal component and a solid support;
an amide reagent, or a urea reagent, or a combination thereof; and
an acid.

For example, in some variations, the acid is a Bronsted acid. In certain variations, the acid is H—X or H—Y, wherein X and Y are as defined for formula (A") or (A) above. In one variation, the acid is hydrochloric acid or sulfonic acid.

In some variations of the composition where the acid may be present, the solid support of the catalyst may be an acidic solid support, as described herein.

In other variations of the composition where the acid may be present, the solid support of the catalyst may be a neutral solid support. In some variations, the neutral solid support is carbon. In one variation, the neutral solid support is activated carbon.

As noted above, in certain variations, any of the metal catalysts described herein may be present in the foregoing compositions. For example, in some variations, the metal component is impregnated, deposited, precipitated, or any combination thereof, onto the basic solid support. In certain variations, the metal component has at least one metal, or at least two metals, or one metal, two metals, or three metals. In one variation, the metal component includes: (i) palladium, or platinum, or a combination thereof; and (ii) gold, silver, or copper, or any combination thereof.

In other variations, such compositions may further include an aromatic reagent. Any of the aromatic reagents described herein may be included. In one variation, the aromatic reagent is toluene, benzene, xylene, or mesitylene, or any combinations thereof. In other variations, the amide or urea reagent and the aromatic reagent are present in a mass ratio of between 1:10 and 10:1, or between 1:9 and 3:1.

As noted above, in certain variations, any of the amide or urea reagents described herein may be present in any of the foregoing compositions. In some variations, an amide reagent is present in the composition. In one variation, the amide reagent is a reagent of formula (i):

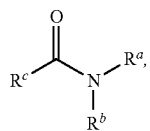
(i)

wherein:
each $R^a$, $R^b$ and $R^c$ is independently H, aliphatic, aryl, or heteroaryl; or $R^a$ and $R^b$ are taken together with the nitrogen atoms to which they are connected to form a cyclic moiety having at least 3 ring atoms.

In other variations, a urea reagent is present in the composition. In one variation, the urea reagent is a reagent of formula (ii):

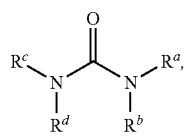
(ii)

wherein:
(A) each $R^a$, $R^b$, $R^c$ and $R^d$ is independently H, aliphatic, aryl or heteroaryl; or (B) $R^a$ and $R^b$ are taken together with the nitrogen atoms to which they are connected to form a cyclic moiety having at least 3 ring atoms; and each $R^c$ and $R^d$ is independently H, aliphatic, aryl or heteroaryl; or (C) each $R^a$ and $R^b$ is independently H, aliphatic, aryl or heteroaryl; and $R^c$ and $R^d$ are taken together with the nitrogen atoms to which they are connected to form a cyclic moiety having at least 3 ring atoms; or (D) $R^a$ and $R^b$ are taken together with the nitrogen atoms to which they are connected to form a cyclic moiety having at least 3 ring atoms; and $R^c$ and $R^d$ are taken together with the nitrogen atoms to which they are connected to form a cyclic moiety having at least 3 ring atoms; or (E) each $R^a$ and $R^c$ is independently H, aliphatic, aryl or heteroaryl; and $R^b$ and $R^d$ are taken together with the nitrogen atoms to which they are connected to form a cyclic moiety having at least 5 ring atoms; or (F) each $R^b$ and $R^d$ is independently H, aliphatic, aryl or heteroaryl; and $R^a$ and $R^c$ are taken together with the nitrogen atoms to which they are connected to form a cyclic moiety having at least 5 ring atoms.

In certain variations, the urea reagent present in the composition is a cyclic urea reagent. In certain variations, the urea reagent is a reagent of formula (iii):

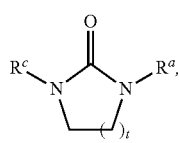
(iii)

wherein:
each $R^a$ and $R^c$ is independently H, aliphatic, aryl or heteroaryl; and t is an integer greater than or equal to 0.

In any of the foregoing variations, the composition may also include an alkylfuran, such as a compound of formula (I″) or (I′). For example, in some variations, the composition may further include a compound of formula (I′):

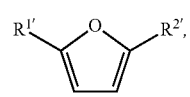
(I′)

wherein:
$R^{1'}$ is $C_m$ alkyl, wherein m is as defined for formula (A), provided that when m is 0, $R^{1'}$ is H; and $R^{2'}$ is $C_n$ alkyl, wherein n is as defined for formula (A).

It should be understood that reference to "about" a value or parameter herein includes (and describes) embodiments that are directed to that value or parameter per se. For example, description referring to "about x" includes description of "x" per se. In other instances, the term "about" when used in association with other measurements, or used to modify a value, a unit, a constant, or a range of values, refers to variations of +/−10%.

It should also be understood that reference to "between" two values or parameters herein includes (and describes) embodiments that include those two values or parameters per se. For example, description referring to "between x and y" includes description of "x" and "y" per se.

As used herein, "aliphatic" refers to a monoradical unbranched or branched hydrocarbon chain that may be saturated (e.g., alkyl) or unsaturated (e.g., alkenyl or alkynyl). In some embodiments, aliphatic as used herein, such as in reagents of formula (i), (ii) and (iii), has 1 to 20 carbon atoms (i.e., $C_{1-20}$ aliphatic), 1 to 8 carbon atoms (i.e., $C_{1-8}$ aliphatic), 1 to 6 carbon atoms (i.e., $C_{1-6}$ aliphatic), or 1 to 4 carbon atoms (i.e., $C_{1-4}$ aliphatic).

"Alkyl" refers to a monoradical unbranched or branched saturated hydrocarbon chain. In some embodiments, alkyl as used herein, such as in compounds of formula (I′) (including, for example, formula (I), formula (I-a) and formula (I-b)) and formula (A) (including, for example, formula (A-i) and (A-ii)), has 1 to 50 carbon atoms (i.e., $C_{1-50}$ alkyl), 1 to 20 carbon atoms (i.e., $C_{1-20}$ alkyl), 1 to 8 carbon atoms (i.e., $C_{1-8}$ alkyl), 1 to 6 carbon atoms (i.e., $C_{1-6}$ alkyl), or 1 to 4 carbon atoms (i.e., $C_{1-4}$ alkyl). Examples of alkyl groups include methyl, ethyl, propyl, isopropyl, n-butyl, sec-butyl, tert-butyl, pentyl, 2-pentyl, isopentyl, neopentyl, hexyl, 2-hexyl, 3-hexyl, and 3-methylpentyl. When an alkyl residue having a specific number of carbons is named, all geometric isomers having that number of carbons may be encompassed; thus, for example, "butyl" can include n-butyl, sec-butyl, isobutyl and t-butyl; "propyl" can include n-propyl and isopropyl.

"Aryl" refers to an aromatic carbocyclic group having a single ring (e.g., phenyl), multiple rings (e.g., biphenyl), or multiple fused rings (e.g., naphthyl, fluorenyl, and anthryl). In certain embodiments, aryl as used herein, such as in compounds of formula (A) (including, for example, formula (A-i) and (A-ii)), has 6 to 50 ring carbon atoms (i.e., $C_{6-50}$ aryl), 6 to 20 ring carbon atoms (i.e., $C_{6-20}$ aryl), or 6 to 12 carbon ring atoms (i.e., $C_{6-12}$ aryl). Aryl, however, does not encompass or overlap in any way with heteroaryl, separately defined below. In certain embodiments, if one or more aryl groups are fused with a heteroaryl ring, the resulting ring system is heteroaryl.

"Heteroaryl" refers to an aromatic group having a single ring, multiple rings, or multiple fused rings, with one or more ring heteroatoms independently selected from nitrogen, oxygen, and sulfur. In some embodiments, heteroaryl is an aromatic, monocyclic or bicyclic ring containing one or more heteroatoms independently selected from nitrogen, oxygen and sulfur with the remaining ring atoms being carbon. In certain embodiments, heteroaryl as used herein, such as in compounds of formula (A) (including, for example, formula (A-i) and (A-ii)), has 3 to 50 ring carbon atoms (i.e., $C_{3-50}$ heteroaryl), 3 to 20 ring carbon atoms (i.e., $C_{3-20}$ heteroaryl), 3 to 12 ring carbon atoms (i.e. $C_{3-12}$ heteroaryl), or 3 to 8 carbon ring atoms (i.e., $C_{3-8}$ heteroaryl); and 1 to 5 heteroatoms, 1 to 4 heteroatoms, 1 to 3 ring heteroatoms, 1 or 2 ring heteroatoms, or 1 ring heteroatom independently selected from nitrogen, oxygen, and sulfur. In one example, a heteroaryl has 3 to 8 ring carbon atoms, with 1 to 3 ring heteroatoms independently selected from nitrogen, oxygen and sulfur. Examples of heteroaryl groups include pyridyl, pyridazinyl, pyrimidinyl, benzothiazolyl, and pyrazolyl. Heteroaryl does not encompass or overlap with aryl as defined above.

Further, it should be understood that when a range of values is listed, it is intended to encompass each value and sub-range within the range. For example, "$C_{1-6}$ alkyl" (which may also be referred to as 1-6C alkyl, C1-C6 alkyl, or C1-6 alkyl) is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

ENUMERATED EMBODIMENTS

The following enumerated embodiments are representative of some aspects of the invention.
1. A method of producing a compound of formula (I'):

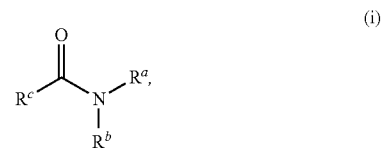

wherein:
   $R^{1'}$ is $C_m$ alkyl, wherein m is an integer greater than or equal to 1; and
   $R^{2'}$ is $C_n$ alkyl, wherein n is an integer greater than or equal to 1,
the method comprising converting a compound of formula (A) to the compound of formula (I') in the presence of hydrogen, a catalyst, and an amide or urea reagent,
wherein:
   the compound of formula (A) is:

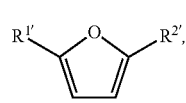

wherein:
   $R^{1a}$ is —$(CH_2)_{m-1}CH(O)$ or —$(CH_2)_m OH$, wherein:
      m is as defined for formula (I'); and
   $R^{2a}$ is —$(CH_2)_{n-1}CH(O)$, —$(CH_2)_n OH$, or —$(CH_2)_n X$, wherein:
      n is as defined for formula (I'); and
      X is halo.

2. The method of embodiment 1, wherein the compound of formula (I') is

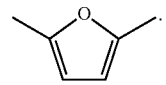

3. The method of embodiment 1 or 2, wherein the reagent has a structure of formula (i):

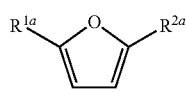

wherein:
   each $R^a$, $R^b$ and $R^c$ is independently H, aliphatic, aryl, or heteroaryl; or
   $R^a$ and $R^b$ are taken together with the nitrogen atoms to which they are connected to form a cyclic moiety having at least 3 ring atoms.

4. The method of embodiment 1 or 2, wherein the reagent has a structure of formula (ii):

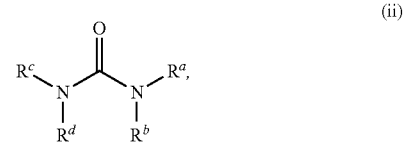

wherein:
   (A) each $R^a$, $R^b$, $R^c$ and $R^d$ is independently H, aliphatic, aryl or heteroaryl; or
   (B) $R^a$ and $R^b$ are taken together with the nitrogen atoms to which they are connected to form a cyclic moiety having at least 3 ring atoms; and each $R^c$ and $R^d$ is independently H, aliphatic, aryl or heteroaryl; or
   (C) each $R^a$ and $R^b$ is independently H, aliphatic, aryl or heteroaryl; and $R^c$ and $R^d$ are taken together with the nitrogen atoms to which they are connected to form a cyclic moiety having at least 3 ring atoms; or
   (D) $R^a$ and $R^b$ are taken together with the nitrogen atoms to which they are connected to form a cyclic moiety having at least 3 ring atoms; and $R^c$ and $R^d$ are taken together with the nitrogen atoms to which they are connected to form a cyclic moiety having at least 3 ring atoms; or
   (E) each $R^a$ and $R^c$ is independently H, aliphatic, aryl or heteroaryl; and $R^b$ and $R^d$ are taken together with the nitrogen atoms to which they are connected to form a cyclic moiety having at least 5 ring atoms; or
   (F) each $R^b$ and $R^d$ is independently H, aliphatic, aryl or heteroaryl; and $R^a$ and $R^c$ are taken together with the nitrogen atoms to which they are connected to form a cyclic moiety having at least 5 ring atoms; and 5. The method of embodiment 1 or 2, wherein the reagent has a structure of formula (ii):

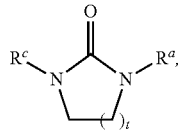

(iii)

wherein:
each $R^a$ and $R^c$ is independently H, aliphatic, aryl or heteroaryl; and
t is an integer greater than or equal to 0.

6. The method of any one of embodiments 1 to 5, wherein $R^{1a}$ is —$(CH_2)_{m-1}CH(O)$.

7. The method of any one of embodiments 1 to 5, wherein $R^{1a}$ is —$(CH_2)_mOH$.

8. The method of any one of embodiments 1 to 7, wherein $R^{2a}$ is —$(CH_2)_{n-1}CH(O)$.

9. The method of any one of embodiments 1 to 7, wherein $R^{2a}$ is —$(CH_2)_nOH$.

10. The method of any one of embodiments 1 to 7, wherein $R^{2a}$ is —$(CH_2)_nX$.

11. The method of any one of embodiments 1 to 5, wherein the compound of formula (A) is

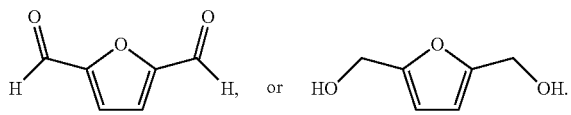

12. The method of embodiment 1 or 2, wherein the compound of formula (A) is

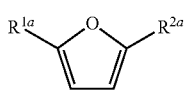

(A)

wherein:
$R^{1a}$ is —$(CH_2)_{m-1}CH(O)$; and
$R^{2a}$ is —$(CH_2)_{n-1}CH(O)$.

13. The method of embodiment 1 or 2, wherein the compound of formula (A) is

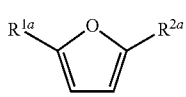

(A)

wherein:
$R^{1a}$ is —$(CH_2)_mOH$; and
$R^{2a}$ is —$(CH_2)_nOH$.

14. The method of any one of embodiments 1 to 7 and 10, wherein X is chloro.

15. The method of embodiment 1 or 2, wherein the reagent of formula (i), (ii) or (iii) is selected from the group consisting of

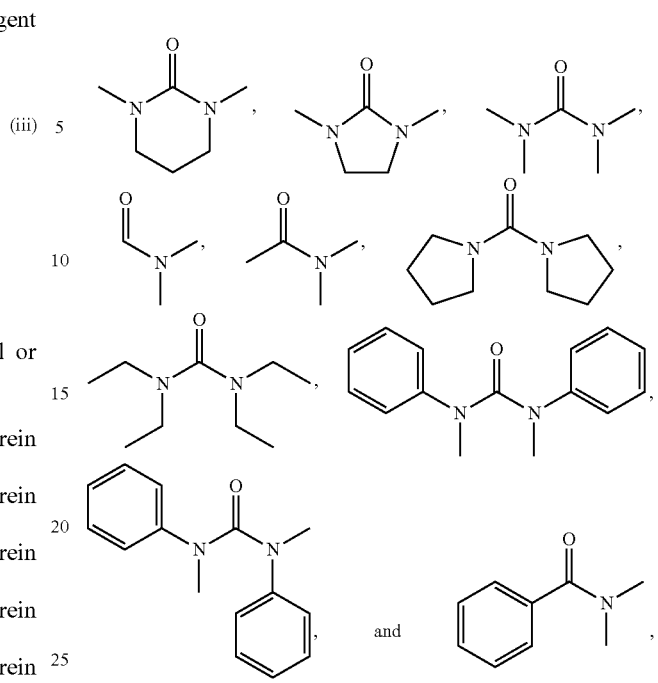

or any combinations thereof.

16. The method of any one of embodiments 1 to 15, wherein the catalyst comprises at least one Group 10 metal.

17. The method of embodiment 16, wherein the catalyst further comprises at least one Group 11 metal.

18. The method of any one of embodiments 1 to 17, wherein the catalyst comprises palladium, or platinum, or any combination thereof.

19. The method of embodiment 18, wherein the catalyst further comprises gold, silver, copper, or any combination thereof.

20. The method of any one of embodiments 1 to 15, wherein the catalyst comprises palladium and at least one additional metal, wherein the palladium and the least one additional metal are present in the catalyst in a weight ratio of 0.5 to 20.

21. The method of any one of embodiments 1 to 15, wherein the catalyst comprises:
(i) palladium;
(ii) palladium and platinum;
(iii) palladium and gold;
(iv) palladium and copper;
(v) palladium and silver;
(vi) platinum;
(vii) platinum and gold;
(viii) platinum and copper; or
(ix) platinum and silver.

22. The method of any one of embodiments 1 to 21, wherein the catalyst has a total metal loading between 0.1% to 15% by weight.

23. The method of any one of embodiments 1 to 15, wherein the catalyst comprises a solid support.

24. The method of embodiment 23, wherein the solid support comprises carbon, a Group 3 metal oxide, a Group 13 metal oxide, a Group 4 metal oxide, a Group 14 metal oxide, or a Group 5 metal oxide, or any combination thereof.

25. The method of embodiment 23, wherein the solid support comprises carbon, silica, alumina, titania, magnesium silicate, aluminosilicate, magnesium oxide, calcium oxide, or zinc oxide, or any combination thereof.

26. The method of embodiment 23, wherein the solid support comprises carbon, alumina, magnesium oxide, or zeolite, or any combination thereof.

27. The method of any one of embodiments 1 to 15, wherein the catalyst is:
Pd/Al$_2$O$_3$;
Pd/C;
Pd+Pt/MgO;
Pd+Au/MgO;
Pd/MgO;
Pd/ZSM5;
Pd/Beta;
Pd+Au+K/C;
Pd+Ag/C;
Pd+Pt/C;
Pt+Cu/C;
Pt+Au/C;
Pt+Ag/C; or
Pd+Au/C,
or any combination thereof.

28. The method of any one of embodiments 1 to 27, wherein the catalyst further comprises a promoter.

29. The method of embodiment 28, wherein the promoter is potassium.

30. The method of any one of embodiments 1 to 15, wherein the catalyst comprises palladium, gold and potassium.

31. The method of any one of embodiments 1 to 30, wherein the compound of formula (A) is converted to the compound of formula (I') in the further presence of acid.

32. The method of embodiment 31, wherein the acid is hydrochloric acid or sulfonic acid.

33. The method of any one of embodiments 1 to 32, wherein the compound of formula (A) is converted to the compound of formula (I') in the further presence of solvent.

34. The method of embodiment 33, wherein the solvent comprises organic solvent.

35. The method of embodiment 33 or 34, wherein the solvent comprises aromatic solvent.

36. The method of any one of embodiments 33 to 35, wherein the solvent comprises at least one mono-aryl compound, at least one di-aryl compound, or at least one tri-aryl compound, or any mixtures thereof.

37. The method of embodiment 36, wherein the at least one mono-aryl compound is toluene or para-xylene.

38. The method of embodiment 33, wherein the solvent comprises one or more aromatic solvents, one or more heavy alkane solvents, one or more ester solvents, one or more silicone oils, or any combinations or mixtures thereof.

39. The method of embodiment 33, wherein the solvent comprises one or more alkyl phenyl solvents.

40. A method of producing a compound of formula (I'):

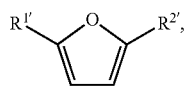
(I')

wherein:
R$^{1'}$ is C$_m$ alkyl, wherein m is an integer greater than or equal to 0, provided that when m is 0, R$^{1'}$ is H; and
R$^{2'}$ is C$_n$ alkyl, wherein n is an integer greater than or equal to 1,
the method comprising converting a compound of formula (A) to the compound of formula (I') in the presence of hydrogen, a catalyst, and an amide or urea reagent,
wherein:
the compound of formula (A) is:

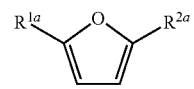
(A)

wherein:
R$^{1a}$ is C$_m$ alkyl, or —(CH$_2$)$_m$Y, wherein:
m is as defined for formula (I'), provided that when m is 0, R$^{1a}$ is H; and
Y is halo; and
R$^{2a}$ is —(CH$_2$)$_{n-1}$CH(O), —(CH$_2$)$_n$OH, or —(CH$_2$)$_n$X, wherein:
n is as defined for formula (I'); and
X is halo; and
the catalyst comprises:
(i) at least two metals; or
(ii) a solid support selected from the group consisting of carbon, silica, alumina, titania, magnesium silicate, aluminosilicate, magnesium oxide, calcium oxide, and zinc oxide, or any combination thereof; or
(iii) both (i) or (ii); or
(iv) palladium and a solid support selected from the group consisting of silica, titania, magnesium silicate, aluminosilicate, magnesium oxide, calcium oxide, and zinc oxide, or any combination thereof; or
(v) platinum and a solid support selected from the group consisting of carbon, silica, alumina, titania, magnesium silicate, aluminosilicate, magnesium oxide, calcium oxide, and zinc oxide, or any combination thereof; or
(vi) palladium, and wherein the catalyst is homogeneous.

41. The method of embodiment 40, wherein at least one of the metals in the catalyst is a Group 10 metal.

42. The method of embodiment 41, wherein at least one of the metals in the catalyst is a Group 11 metal.

43. The method of any one of embodiments 40 to 42, wherein the catalyst comprises palladium and platinum.

44. The method of embodiment 40, wherein the catalyst comprises:
(i) palladium or platinum; and
(ii) gold, silver, or copper, or any combination thereof.

45. The method of embodiment 40, wherein the catalyst comprises palladium and at least one additional metal, wherein the palladium and the least one additional metal are present in the catalyst in a weight ratio of 0.5 to 20.

46. The method of embodiment 40, wherein the catalyst comprises:
(i) palladium;
(ii) palladium and platinum;
(iii) palladium and gold;
(iv) palladium and copper;
(v) palladium and silver;
(vi) platinum;
(vii) platinum and gold;
(viii) platinum and copper; or
(ix) platinum and silver.

47. The method of any one of embodiments 40 to 46, wherein the catalyst has a total metal loading between 0.1% to 15% by weight.

48. The method of any one of embodiments 40 to 47, wherein the catalyst comprises a solid support.

49. The method of embodiment 48, wherein the solid support comprises carbon, a Group 3 metal oxide, a Group 13 metal oxide, a Group 4 metal oxide, a Group 14 metal oxide, or a Group 5 metal oxide, or any combination thereof.

50. The method of embodiment 49, wherein the solid support comprises carbon, silica, alumina, titania, magnesium silicate, aluminosilicate, magnesium oxide, calcium oxide, or zinc oxide, or any combination thereof.

51. The method of embodiment 40, wherein the catalyst is:
Pd+Pt/MgO;
Pd+Au/MgO;
Pd+Au+K/C;
Pd+Ag/C;
Pd+Pt/C;
Pt+Cu/C;
Pt+Au/C;
Pt+Ag/C; or
Pd+Au/C,
or any combination thereof.

52. The method of any one of embodiments 40 to 51, wherein the catalyst further comprises a promoter.

53. The method of embodiment 52, wherein the promoter is potassium.

54. The method of embodiment 40, wherein the catalyst comprises palladium, gold and potassium.

55. The method of any one of embodiments 40 to 54, wherein the reagent has a structure of formula (i):

$$\text{(i)}$$

wherein:
each $R^a$, $R^b$ and $R^c$ is independently H, aliphatic, aryl, or heteroaryl; or
$R^a$ and $R^b$ are taken together with the nitrogen atoms to which they are connected to form a cyclic moiety having at least 3 ring atoms.

56. The method of any one of embodiments 40 to 55, wherein the reagent of formula (i) is other than N,N-dimethylformamide and N,N-dimethylacetamide.

57. The method of any one of embodiments 40 to 55, wherein when $R^c$ is H or methyl, then one of $R^a$ and $R^b$ is other than methyl.

58. The method of any one of embodiments 40 to 54, wherein the reagent has a structure of formula (ii):

$$\text{(ii)}$$

wherein:
(A) each $R^a$, $R^b$, $R^c$ and $R^d$ is independently H, aliphatic, aryl or heteroaryl; or
(B) $R^a$ and $R^b$ are taken together with the nitrogen atoms to which they are connected to form a cyclic moiety having at least 3 ring atoms; and each $R^c$ and $R^d$ is independently H, aliphatic, aryl or heteroaryl; or
(C) each $R^a$ and $R^b$ is independently H, aliphatic, aryl or heteroaryl; and $R^c$ and $R^d$ are taken together with the nitrogen atoms to which they are connected to form a cyclic moiety having at least 3 ring atoms; or
(D) $R^a$ and $R^b$ are taken together with the nitrogen atoms to which they are connected to form a cyclic moiety having at least 3 ring atoms; and $R^c$ and $R^d$ are taken together with the nitrogen atoms to which they are connected to form a cyclic moiety having at least 3 ring atoms; or
(E) each $R^a$ and $R^c$ is independently H, aliphatic, aryl or heteroaryl; and $R^b$ and $R^d$ are taken together with the nitrogen atoms to which they are connected to form a cyclic moiety having at least 5 ring atoms; or
(F) each $R^b$ and $R^d$ is independently H, aliphatic, aryl or heteroaryl; and $R^a$ and $R^c$ are taken together with the nitrogen atoms to which they are connected to form a cyclic moiety having at least 5 ring atoms; and 59. The method of any one of embodiments 40 to 54, wherein the reagent has a structure of formula (ii):

$$\text{(iii)}$$

wherein:
each $R^a$ and $R^c$ is independently H, aliphatic, aryl or heteroaryl; and
t is an integer greater than or equal to 0.

60. The method of any one of embodiments 40 to 54, wherein the reagent of formula (i), (ii) or (iii) is selected from the group consisting of or any combinations thereof.

61. The method of any one of embodiments 40 to 60, wherein the compound of formula (I') is a compound of formula (I-a) or (I-b):

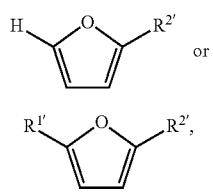
(I-a)

or

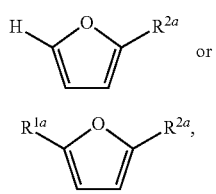
(I-b)

wherein $R^{1'}$ is $C_m$ alkyl, wherein m is an integer greater than or equal to 1.

62. The method of any one of embodiments 40 to 60, wherein the compound of formula (I') is

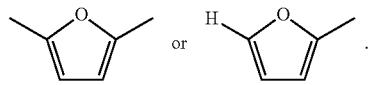.

63. The method of any one of embodiments 40 to 61, wherein the compound of formula (A) is a compound of formula (A-i) or (A-ii):

(A-i)

or (A-ii)

wherein m is an integer greater than or equal to 1.

64. The method of any one of embodiments 40 to 63, wherein $R^{1a}$ is $C_m$ alkyl.

65. The method of any one of embodiments 40 to 63, wherein $R^{1a}$ is —$(CH_2)_mY$.

66. The method of any one of embodiments 40 to 65, wherein $R^{2a}$ is —$(CH_2)_{n-1}CH(O)$.

67. The method of any one of embodiments 40 to 65, wherein $R^{2a}$ is —$(CH_2)_nOH$.

68. The method of any one of embodiments 40 to 65, wherein $R^{2a}$ is —$(CH_2)_nX$.

69. The method of any one of embodiments 40 to 61, wherein the compound of formula (A)

is 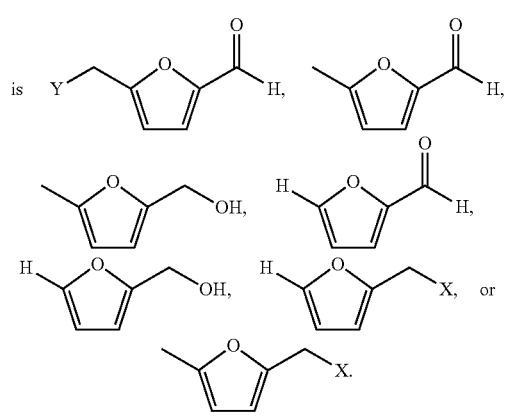

70. The method of any one of embodiments 40 to 61, wherein the compound of formula (A) is

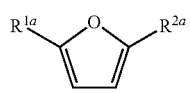
(A)

wherein:
$R^{1a}$ is —$(CH_2)_mY$, wherein:
m is an integer greater than or equal to 1; and
Y is halo; and
$R^{2a}$ is —$(CH_2)_{n-1}CH(O)$, wherein:
n is an integer greater than or equal to 1.

71. The method of any one of embodiments 40 to 61, wherein the compound of formula (A) is:

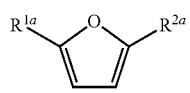
(A)

wherein:
$R^{1a}$ is $C_m$ alkyl, wherein:
m is an integer greater than or equal to 1; and
$R^{2a}$ is —$(CH_2)_{n-1}CH(O)$, wherein:
n is an integer greater than or equal to 1.

72. The method of any one of embodiments 40 to 61, wherein the compound of formula (A) is:

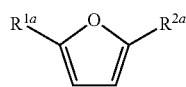
(A)

wherein:
$R^{1a}$ is $C_m$ alkyl, wherein:
m is an integer greater than or equal to 1; and
$R^{2a}$ is —$(CH_2)_nOH$, wherein:
n is an integer greater than or equal to 1.

73. The method of any one of embodiments 40 to 61, wherein the compound of formula (A) is:

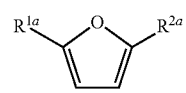
(A)

wherein:
$R^{1a}$ is H; and
$R^{2a}$ is —$(CH_2)_{n-1}CH(O)$, wherein:
n is an integer greater than or equal to 1.

74. The method of any one of embodiments 40 to 61, wherein the compound of formula (A) is:

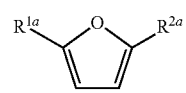
(A)

wherein:
$R^{1a}$ is H; and
$R^{2a}$ is —$(CH_2)_nOH$, wherein:
n is an integer greater than or equal to 1.

75. The method of any one of embodiments 40 to 61, wherein the compound of formula (A) is:

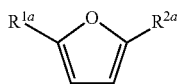

(A)

wherein:
R$^{1a}$ is H; and
R$^{2a}$ is —(CH$_2$)$_n$X, wherein:
n is an integer greater than or equal to 1; and
X is halo.

76. The method of any one of embodiments 40 to 61, wherein the compound of formula (A) is:

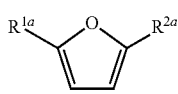

(A)

wherein:
R$^{1a}$ is C$_m$ alkyl, wherein:
m is an integer greater than or equal to 1; and
R$^{2a}$ is —(CH$_2$)$_n$X, wherein:
n is an integer greater than or equal to 1; and
X is halo.

77. The method of any one of embodiments 40 to 70, wherein Y is chloro.

78. The method of any one of embodiments 40 to 65, 68, 69, 75 and 76, wherein X is chloro.

79. The method of any one of embodiments 40 to 78, wherein the compound of formula (A) is converted to the compound of formula (I') in the further presence of acid.

80. The method of embodiment 79, wherein the acid is hydrochloric acid or sulfonic acid.

81. The method of any one of embodiments 40 to 80, wherein the compound of formula (A) is converted to the compound of formula (I') in the further presence of solvent.

82. The method of embodiment 81, wherein the solvent comprises organic solvent.

83. The method of embodiment 81 or 82, wherein the solvent comprises aromatic solvent.

84. The method of any one of embodiments 81 to 83, wherein the solvent comprises at least one mono-aryl compound, at least one di-aryl compound, or at least one tri-aryl compound, or any mixtures thereof.

85. The method of embodiment 84, wherein the at least one mono-aryl compound is toluene or para-xylene.

86. The method of embodiment 81, wherein the solvent comprises one or more aromatic solvents, one or more heavy alkane solvents, one or more ester solvents, one or more silicone oils, or any combinations or mixtures thereof.

87. The method of embodiment 81, wherein the solvent comprises one or more alkyl phenyl solvents.

88. A composition, comprising:
a compound of formula (A):

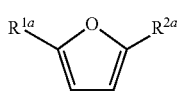

(A)

wherein:
R$^{1a}$ is —(CH$_2$)$_{m-1}$CH(O) or —(CH$_2$)$_m$OH, wherein:
m is an integer greater than or equal to 1; and R$^{2a}$ is —(CH$_2$)$_{n-1}$CH(O), —(CH$_2$)$_n$OH, or —(CH$_2$)$_n$X, wherein:
n is an integer greater than or equal to 1; and
X is halo;
hydrogen;
a catalyst; and
an amide or urea reagent.

89. The composition of embodiment 88, further comprising a compound of formula (I'):

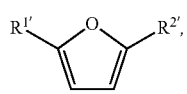

(I')

wherein:
R$^{1'}$ is C$_m$ alkyl, wherein m is as defined for formula (A); and
R$^{2'}$ is C$_n$ alkyl, wherein n is as defined for formula (A).

90. The composition of embodiment 89, wherein the compound of formula (I') is

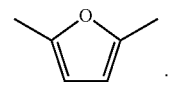

.

91. The composition of any one of embodiments 88 to 90, wherein the reagent has a structure of formula (i):

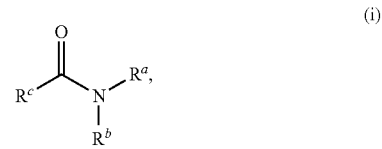

(i)

wherein:
each R$^a$, R$^b$ and R$^c$ is independently H, aliphatic, aryl, or heteroaryl; or
R$^a$ and R$^b$ are taken together with the nitrogen atoms to which they are connected to form a cyclic moiety having at least 3 ring atoms.

92. The composition of any one of embodiments 88 to 90, wherein the reagent has a structure of formula (ii):

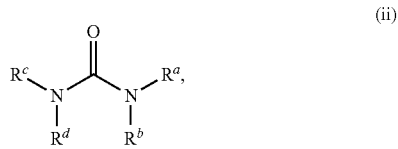

(ii)

wherein:
(A) each R$^a$, R$^b$, R$^c$ and R$^d$ is independently H, aliphatic, aryl or heteroaryl; or
(B) R$^a$ and R$^b$ are taken together with the nitrogen atoms to which they are connected to form a cyclic moiety having at least 3 ring atoms; and each R$^c$ and R$^d$ is independently H, aliphatic, aryl or heteroaryl; or
(C) each R$^a$ and R$^b$ is independently H, aliphatic, aryl or heteroaryl; and R$^c$ and R$^d$ are taken together with the nitrogen atoms to which they are connected to form a cyclic moiety having at least 3 ring atoms; or
(D) $R^a$ and $R^b$ are taken together with the nitrogen atoms to which they are connected to form a cyclic moiety having at least 3 ring atoms; and $R^c$ and $R^d$ are taken together with the nitrogen atoms to which they are connected to form a cyclic moiety having at least 3 ring atoms; or
(E) each $R^a$ and $R^c$ is independently H, aliphatic, aryl or heteroaryl; and $R^b$ and $R^d$ are taken together with the nitrogen atoms to which they are connected to form a cyclic moiety having at least 5 ring atoms; or
(F) each $R^b$ and $R^d$ is independently H, aliphatic, aryl or heteroaryl; and $R^a$ and $R^c$ are taken together with the nitrogen atoms to which they are connected to form a cyclic moiety having at least 5 ring atoms; and 93. The composition of any one of embodiments 88 to 90, wherein the reagent has a structure of formula (ii):

(iii)

wherein:
each $R^a$ and $R^c$ is independently H, aliphatic, aryl or heteroaryl; and
t is an integer greater than or equal to 0.

94. The composition of any one of embodiments 88 to 93, wherein $R^{1a}$ is —$(CH_2)_{m-1}CH(O)$.
95. The composition of any one of embodiments 88 to 93, wherein $R^{1a}$ is —$(CH_2)_mOH$.
96. The composition of any one of embodiments 88 to 95, wherein $R^{2a}$ is —$(CH_2)_{n-1}CH(O)$.
97. The composition of any one of embodiments 88 to 95, wherein $R^{2a}$ is —$(CH_2)_nOH$.
98. The composition of any one of embodiments 88 to 95, wherein $R^{2a}$ is —$(CH_2)_nX$.
99. The composition of any one of embodiments 88 to 93, wherein the compound of formula (A) is 100. The composition of any one of embodiments 88 to 93, wherein the compound of formula (A) is (A)

wherein:
$R^{1a}$ is —$(CH_2)_{m-1}CH(O)$; and
$R^{2a}$ is —$(CH_2)_{n-1}CH(O)$.

101. The composition of any one of embodiments 88 to 93, wherein the compound of formula (A) is (A)

wherein:
$R^{1a}$ is —$(CH_2)_mOH$; and
$R^{2a}$ is —$(CH_2)_nOH$.

102. The composition of any one of embodiments 88 to 93, wherein the reagent of formula (i), (ii) or (iii) is selected from the group consisting of or any combinations thereof.

103. The composition of any one of embodiments 88 to 102, wherein the catalyst comprises at least one Group 10 metal.
104. The composition of embodiment 103, wherein the catalyst further comprises at least one Group 11 metal.
105. The composition of any one of embodiments 88 to 104, wherein the catalyst comprises palladium, or platinum, or any combination thereof.
106. The composition of embodiment 105, wherein the catalyst further comprises gold, silver, or copper, or any combination thereof.
107. The composition of any one of embodiments 88 to 102, wherein the catalyst comprises palladium and at least one additional metal, wherein the palladium and the least one additional metal are present in the catalyst in a weight ratio of 0.5 to 20.
108. The composition of any one of embodiments 88 to 102, wherein the catalyst comprises:
(i) palladium;
(ii) palladium and platinum;
(iii) palladium and gold;
(iv) palladium and copper;
(v) palladium and silver;
(vi) platinum;
(vii) platinum and gold;
(viii) platinum and copper; or
(ix) platinum and silver.

109. The composition of any one of embodiments 88 to 108, wherein the catalyst has a total metal loading between 0.1% to 15% by weight.
110. The composition of any one of embodiments 88 to 102, wherein the catalyst comprises a solid support.
111. The composition of embodiment 110, wherein the solid support comprises carbon, a Group 3 metal oxide, a Group 13 metal oxide, a Group 4 metal oxide, a Group 14 metal oxide, or a Group 5 metal oxide, or any combination thereof.
112. The composition of embodiment 110, wherein the solid support comprises carbon, silica, alumina, titania, magnesium silicate, aluminosilicate, magnesium oxide, calcium oxide, or zinc oxide, or any combination thereof.
113. The composition of any one of embodiments 88 to 102, wherein the catalyst is:
Pd/Al$_2$O$_3$;
Pd/C;
Pd+Pt/MgO;
Pd+Au/MgO;
Pd/MgO;
Pd/ZSM5;
Pd/Beta;
Pd+Au+K/C;
Pd+Ag/C;
Pd+Pt/C;
Pt+Cu/C;
Pt+Au/C;
Pt+Ag/C; or
Pd+Au/C,
or any combination thereof.
114. The composition of any one of embodiments 88 to 113, wherein the catalyst further comprises a promoter.
115. The composition of embodiment 114, wherein the promoter is potassium.
116. The composition of any one of embodiments 88 to 102, wherein the catalyst comprises palladium, gold and potassium.
117. The composition of any one of embodiments 88 to 116, further comprising acid.
118. The composition of embodiment 117, wherein the acid is hydrochloric acid or sulfonic acid.
119. The composition of any one of embodiments 88 to 118, further comprising solvent.
120. The composition of embodiment 119, wherein the solvent comprises organic solvent.
121. The composition of embodiment 119 or 120, wherein the solvent comprises aromatic solvent.
122. The composition of any one of embodiments 119 to 121, wherein the solvent comprises at least one mono-aryl compound, at least one di-aryl compound, or at least one tri-aryl compound, or any mixtures thereof.
123. The composition of embodiment 122, wherein the at least one mono-aryl compound is toluene or para-xylene.
124. The composition of embodiment 119, wherein the solvent comprises one or more aromatic solvents, one or more heavy alkane solvents, one or more ester solvents, one or more silicone oils, or any combinations or mixtures thereof.
125. The composition of embodiment 119, wherein the solvent comprises one or more alkyl phenyl solvents.
126. A composition, comprising:
a compound of formula (A):

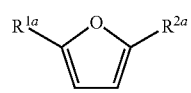 (A)

wherein:
R$^{1a}$ is C$_m$ alkyl, or —(CH$_2$)$_m$Y, wherein:
m is an integer greater than or equal to 0, provided that when m is 0, R$^{1a}$ is H; and
Y is halo; and
R$^{2a}$ is —(CH$_2$)$_{n-1}$CH(O), —(CH$_2$)$_n$OH, or —(CH$_2$)$_n$X, wherein:
m is an integer greater than or equal to 1; and
X is halo; and
an amide or urea reagent;
hydrogen; and
a catalyst comprising:
(i) at least two metals; or
(ii) a solid support selected from the group consisting of carbon, silica, alumina, titania, magnesium silicate, aluminosilicate, magnesium oxide, calcium oxide, and zinc oxide, or any combination thereof; or
(iii) both (i) or (ii); or
(iv) palladium and a solid support selected from the group consisting of silica, titania, magnesium silicate, aluminosilicate, magnesium oxide, calcium oxide, and zinc oxide, or any combination thereof; or
(v) platinum and a solid support selected from the group consisting of carbon, silica, alumina, titania, magnesium silicate, aluminosilicate, magnesium oxide, calcium oxide, and zinc oxide, or any combination thereof; or
(vi) palladium, and wherein the catalyst is homogeneous.
127. The composition of embodiment 126, wherein at least one of the metals in the catalyst is a Group 10 metal.
128. The composition of embodiment 127, wherein at least one of the metals in the catalyst is a Group 11 metal.
129. The composition of any one of embodiments 126 to 128, wherein the catalyst comprises palladium and platinum.
130. The composition of embodiment 126, wherein the catalyst comprises: (i) palladium or platinum; and (ii) gold, silver, or copper, or any combination thereof.
131. The composition of embodiment 126, wherein the catalyst comprises palladium and at least one additional metal, wherein the palladium and the least one additional metal are present in the catalyst in a weight ratio of 0.5 to 20.
132. The composition of embodiment 126, wherein the catalyst comprises:
(i) palladium;
(ii) palladium and platinum;
(iii) palladium and gold;
(iv) palladium and copper;
(v) palladium and silver;
(vi) platinum;
(vii) platinum and gold;
(viii) platinum and copper; or
(ix) platinum and silver.
133. The composition of any one of embodiments 126 to 132, wherein the catalyst has a total metal loading between 0.1% to 15% by weight.
134. The composition of any one of embodiments 126 to 133, wherein the catalyst comprises a solid support.
135. The composition of embodiment 134, wherein the solid support comprises carbon, a Group 3 metal oxide, a Group 13 metal oxide, a Group 4 metal oxide, a Group 14 metal oxide, or a Group 5 metal oxide, or any combination thereof.
136. The composition of embodiment 135, wherein the solid support comprises carbon, silica, alumina, titania, magnesium silicate, aluminosilicate, magnesium oxide, calcium oxide, or zinc oxide, or any combination thereof.

137. The composition of embodiment 126, wherein the catalyst is:
   Pd+Pt/MgO;
   Pd+Au/MgO;
   Pd+Au+K/C;
   Pd+Ag/C;
   Pd+Pt/C;
   Pt+Cu/C;
   Pt+Au/C;
   Pt+Ag/C; or
   Pd+Au/C,
   or any combination thereof.

138. The composition of any one of embodiments 126 to 137, wherein the catalyst further comprises a promoter.

139. The composition of embodiment 138, wherein the promoter is potassium.

140. The composition of embodiment 126, wherein the catalyst comprises palladium, gold and potassium.

141. The composition of any one of embodiments 126 to 140, wherein the reagent is a reagent of formula (i):

$$R^c \underset{R^b}{\overset{O}{\underset{|}{-}\!\!\!\!\!\!\!\!-\!\!-N-R^a}},\quad (i)$$

wherein:
   each $R^a$, $R^b$ and $R^c$ is independently H, aliphatic, aryl, or heteroaryl; or
   $R^a$ and $R^b$ are taken together with the nitrogen atoms to which they are connected to form a cyclic moiety having at least 3 ring atoms.

142. The composition of embodiment 141, wherein the reagent of formula (i) is other than N,N-dimethylformamide and N,N-dimethylacetamide.

143. The composition of embodiment 141, wherein when $R^c$ is H or methyl, then one of $R^a$ and $R^b$ is other than methyl.

144. The composition of any one of embodiments 126 to 140, wherein the reagent is a reagent of formula (ii):

$$R^c\underset{R^d}{\overset{O}{-N-}}\underset{R^b}{-N-}R^a,\quad (ii)$$

wherein:
   (A) each $R^a$, $R^b$, $R^c$ and $R^d$ is independently H, aliphatic, aryl or heteroaryl; or
   (B) $R^a$ and $R^b$ are taken together with the nitrogen atoms to which they are connected to form a cyclic moiety having at least 3 ring atoms; and each $R^c$ and $R^d$ is independently H, aliphatic, aryl or heteroaryl; or
   (C) each $R^a$ and $R^b$ is independently H, aliphatic, aryl or heteroaryl; and $R^c$ and $R^d$ are taken together with the nitrogen atoms to which they are connected to form a cyclic moiety having at least 3 ring atoms; or
   (D) $R^a$ and $R^b$ are taken together with the nitrogen atoms to which they are connected to form a cyclic moiety having at least 3 ring atoms; and $R^c$ and $R^d$ are taken together with the nitrogen atoms to which they are connected to form a cyclic moiety having at least 3 ring atoms; or
   (E) each $R^a$ and $R^c$ is independently H, aliphatic, aryl or heteroaryl; and $R^b$ and $R^d$ are taken together with the nitrogen atoms to which they are connected to form a cyclic moiety having at least 5 ring atoms; or
   (F) each $R^b$ and $R^d$ is independently H, aliphatic, aryl or heteroaryl; and $R^a$ and $R^c$ are taken together with the nitrogen atoms to which they are connected to form a cyclic moiety having at least 5 ring atoms.

145. The composition of any one of embodiments 126 to 140, wherein the reagent is a reagent of formula (iii):

$$R^c-N\underset{(\phantom{X})_t}{\overset{O}{\underset{\phantom{|}}{\bigcup}}}N-R^a,\quad (iii)$$

wherein:
   each $R^a$ and $R^c$ is independently H, aliphatic, aryl or heteroaryl; and
   t is an integer greater than or equal to 0.

146. The composition of any one of embodiments 126 to 140, wherein the reagent of formula (i), (ii) or (iii) is selected from the group consisting of

[chemical structures]

or any combinations thereof.

147. The composition of any one of embodiments 126 to 146, further comprising a compound of formula (I'):

$$R^{1'}\!\!-\!\!\underset{\phantom{X}}{\overset{O}{\bigcirc}}\!\!-\!\!R^{2'},\quad (I')$$

wherein:
   $R^{1'}$ is $C_m$ alkyl, wherein m is an integer greater than or equal to 0, provided that when m is 0, $R^{1'}$ is H; and $R^{2'}$ is $C_n$ alkyl, wherein n is an integer greater than or equal to 1.

148. The composition of embodiment 147, wherein the compound of formula (I') is a compound of formula (I-a) or (I-b):

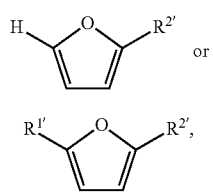

(I-a)

or (I-b)

wherein $R^{1'}$ is $C_m$ alkyl, wherein m is an integer greater than or equal to 1.

149. The composition of embodiment 147, wherein the compound of formula (I') is

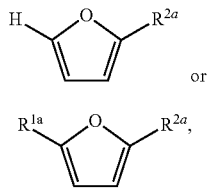

or

.

150. The composition of any one of embodiments 126 to 149, wherein the compound of formula (A) is a compound of formula (A-i) or (A-ii):

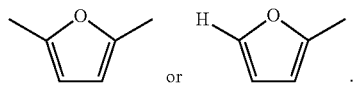

(A-i)

or (A-ii)

wherein m is an integer greater than or equal to 1.

151. The composition of any one of embodiments 126 to 150, wherein $R^{1a}$ is $C_m$ alkyl.
152. The composition of any one of embodiments 126 to 150, wherein $R^{1a}$ is —(CH$_2$)$_m$Y.
153. The composition of any one of embodiments 126 to 152, wherein $R^{2a}$ is —(CH$_2$)$_{n-1}$CH(O).
154. The composition of any one of embodiments 126 to 152, wherein $R^{2a}$ is —(CH$_2$)$_n$OH.
155. The composition of any one of embodiments 126 to 152, wherein $R^{2a}$ is —(CH$_2$)$_n$X.
156. The composition of any one of embodiments 126 to 149, wherein the compound of formula (A) is

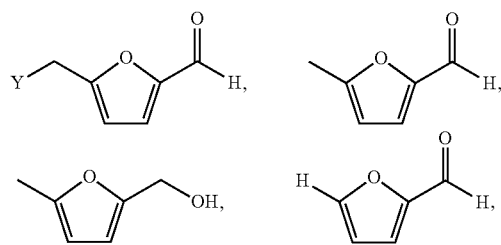

157. The composition of any one of embodiments 126 to 149, wherein the compound of formula (A) is

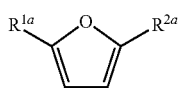

(A)

wherein:
$R^{1a}$ is —(CH$_2$)$_m$Y, wherein:
m is an integer greater than or equal to 1; and
Y is halo; and
$R^{2a}$ is —(CH$_2$)$_{n-1}$CH(O), wherein:
n is an integer greater than or equal to 1.

158. The composition of any one of embodiments 126 to 149, wherein the compound of formula (A) is:

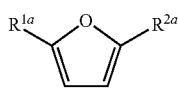

(A)

wherein:
$R^{1a}$ is $C_m$ alkyl, wherein:
m is an integer greater than or equal to 1; and
$R^{2a}$ is —(CH$_2$)$_{n-1}$CH(O), wherein:
n is an integer greater than or equal to 1.

159. The composition of any one of embodiments 126 to 149, wherein the compound of formula (A) is:

(A)

wherein:
$R^{1a}$ is $C_m$ alkyl, wherein:
m is an integer greater than or equal to 1; and
$R^{2a}$ is —(CH$_2$)$_n$OH, wherein:
n is an integer greater than or equal to 1.

160. The composition of any one of embodiments 126 to 149, wherein the compound of formula (A) is:

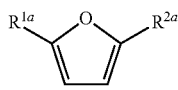

(A)

wherein:
$R^{1a}$ is H; and
$R^{2a}$ is —(CH$_2$)$_{n-1}$CH(O), wherein:
n is an integer greater than or equal to 1.

161. The composition of any one of embodiments 126 to 149, wherein the compound of formula (A) is:

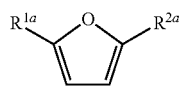

wherein:
R$^{1a}$ is H; and
R$^{2a}$ is —(CH$_2$)$_n$OH, wherein:
n is an integer greater than or equal to 1.

162. The composition of any one of embodiments 126 to 149, wherein the compound of formula (A) is:

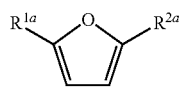

wherein:
R$^{1a}$ is H; and
R$^{2a}$ is —(CH$_2$)$_n$X, wherein:
n is an integer greater than or equal to 1; and
X is halo.

163. The composition of any one of embodiments 126 to 149, wherein the compound of formula (A) is:

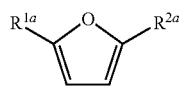

wherein:
R$^{1a}$ is C$_m$ alkyl, wherein:
m is an integer greater than or equal to 1; and
R$^{2a}$ is —(CH$_2$)$_n$X, wherein:
n is an integer greater than or equal to 1; and
X is halo.

164. The composition of any one of embodiments 126 to 157, wherein Y is chloro.

165. The composition of any one of embodiments 126 to 152, 155, 156, 162 and 163, wherein X is chloro.

166. The composition of any one of embodiments 126 to 165, wherein the compound of formula (A) is converted to the compound of formula (I') in the further presence of acid.

167. The composition of embodiment 166, wherein the acid is hydrochloric acid or sulfonic acid.

168. The composition of any one of embodiments 126 to 167, wherein the compound of formula (A) is converted to the compound of formula (I') in the further presence of solvent.

169. The composition of embodiment 168, wherein the solvent comprises organic solvent.

170. The composition of embodiment 168 or 169, wherein the solvent comprises aromatic solvent.

171. The composition of any one of embodiments 168 to 170, wherein the solvent comprises at least one mono-aryl compound, at least one di-aryl compound, or at least one tri-aryl compound, or any mixtures thereof.

172. The composition of embodiment 171, wherein the at least one mono-aryl compound is toluene or para-xylene.

173. The composition of embodiment 168, wherein the solvent comprises one or more aromatic solvents, one or more heavy alkane solvents, one or more ester solvents, one or more silicone oils, or any combinations or mixtures thereof.

174. The composition of embodiment 168, wherein the solvent comprises one or more alkyl phenyl solvents.

175. A method of producing para-xylene, comprising:
combining a compound of formula (I') produced according to the method of any one of embodiments 1 to 87 and ethylene to produce para-xylene, wherein the compound of formula (I') is 2,5-dimethylfuran.

176. A method of producing terephthalic acid, comprising:
combining a compound of formula (I') produced according to the method of any one of embodiments 1 to 87 and ethylene to produce para-xylene, wherein the compound of formula (I') is 2,5-dimethylfuran; and
oxidizing the para-xylene to terephthalic acid.

177. A method of producing polyethylene terephthalate, comprising:
combining a compound of formula (I') produced according to the method of any one of embodiments 1 to 87 and ethylene to produce para-xylene, wherein the compound of formula (I') is 2,5-dimethylfuran;
oxidizing the para-xylene to terephthalic acid; and
polymerizing terephthalic acid with ethylene glycol to produce polyethylene terephthalate.

178. A method of producing a compound of formula (I"):

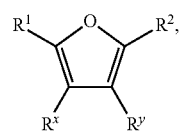

wherein:
R$^{1'}$ is C$_m$ alkyl, wherein m is an integer greater than or equal to 0, provided that when m is 0, R$^{1'}$ is H;
R$^{2'}$ is C$_n$ alkyl, wherein n is an integer greater than or equal to 1; and
R$^x$ and R$^y$ are independently H or alkyl,
the method comprising converting a compound of formula (A") to the compound of formula (I") in the presence of (1) hydrogen and (2) a solid-supported metal catalyst comprising a metal component and a basic solid support, and (3) optionally an amide reagent, a urea reagent, or a combination thereof, to produce additional compound of formula (I'), wherein:
the compound of formula (A") is:

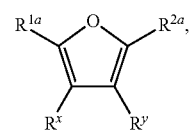

wherein:
R$^{1a}$ is C$_m$ alkyl, —(CH$_2$)$_m$Y, —(CH$_2$)$_{m-1}$CH(O) or —(CH$_2$)$_m$OH wherein:
m is as defined for formula (I"), provided that when m is 0, R$^{1a}$ is H; and
Y is halo; and $R^{2a}$ is —$(CH_2)_{n-1}CH(O)$, —$(CH_2)_nOH$, or —$(CH_2)_nX$, wherein:
  n is as defined for formula (I''); and
  X is halo; and
$R^x$ and $R^y$ are as defined for formula (I''),
the basic solid support is a solid support that (i) has more basic sites than acidic sites and (ii) chemisorbs at least 0.001 g carbon dioxide/g solid support.

179. The method of embodiment 178, wherein:
the compound of formula (I'') is a compound of formula (I'):

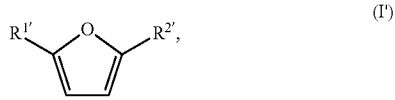

(I')

wherein:
  $R^{1'}$ is $C_m$ alkyl, wherein m is an integer greater than or equal to 0, provided that when m is 0, $R^{1'}$ is H; and
  $R^{2'}$ is $C_n$ alkyl, wherein n is an integer greater than or equal to 1; and
the compound of formula (A'') is a compound of formula (A):

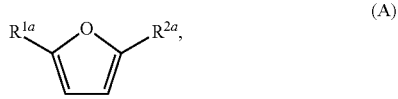

(A)

wherein:
  $R^{1a}$ is $C_m$ alkyl, —$(CH_2)_mY$, —$(CH_2)_{m-1}CH(O)$ or —$(CH_2)_mOH$ wherein:
    m is as defined for formula (I'), provided that when m is 0, $R^{1a}$ is H; and
    Y is halo; and
  $R^{2a}$ is —$(CH_2)_{n-1}CH(O)$, —$(CH_2)_nOH$, or —$(CH_2)_nX$, wherein:
    n is as defined for formula (I'); and
    X is halo.

180. The method of embodiment 178 or 179, wherein the basic solid support comprises a basic metal oxide.

181. The method of embodiment 178 or 179, wherein the basic solid support comprises a solid support modified by an alkali metal or an alkali earth metal.

182. The method of embodiment 178 or 179, wherein the basic solid support comprises a solid support modified by a base.

183. The method of embodiment 178 or 179, wherein the basic solid support comprises BeO, MgO, CaO, SrO, BaO, ZnO, $Al_2O_3$, $Y_2O_3$, $La_2O_3$, $CeO_2$, $ThO_2$, $TiO_2$, $ZrO_2$ or $SnO_2$, or any combinations thereof.

184. The method of embodiment 178 or 179, wherein the catalyst is:
  Pd+Pt/MgO;
  Pd+Au/MgO; or
  Pd/MgO,
or any combination thereof.

185. The method of embodiment 178 to 184, further comprising isolating the compound of formula (I'').

186. The method of embodiment 178 to 185, wherein the converting the compound of formula (A'') to the compound of formula (I'') in the presence of (1) hydrogen and (2) the solid-supported metal catalyst produces a residual solid-supported metal catalyst, and the method further comprises isolating the residual solid-supported metal catalyst.

187. The method of embodiment 178 to 186, wherein the converting the compound of formula (A'') to the compound of formula (I'') in the presence of (1) hydrogen and (2) the solid-supported metal catalyst produces a residual solid-supported metal catalyst, and the method further comprises:
regenerating the residual solid-supported metal catalyst to produce a regenerated solid-supported metal catalyst; and
combining the regenerated solid-supported metal catalyst with additional compound of formula (A'') in the presence of additional hydrogen and optionally additional amide reagent, urea reagent, or a combination thereof, to produce additional compound of formula (I'').

188. A method of producing a compound of formula (I''):

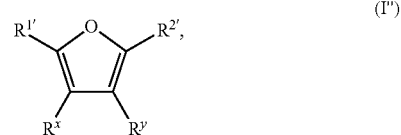

(I'')

wherein:
  $R^{1'}$ is $C_m$ alkyl, wherein m is an integer greater than or equal to 0, provided that when m is 0, $R^{1'}$ is H;
  $R^{2'}$ is $C_n$ alkyl, wherein n is an integer greater than or equal to 1; and
  $R^x$ and $R^y$ are independently H or alkyl,
the method comprising converting a compound of formula (A'') to the compound of formula (I'') in the presence of (1) hydrogen, (2) a catalyst comprising a metal component and an acidic solid support, and (3) an amide reagent, a urea reagent, or a combination thereof,
wherein:
the compound of formula (A'') is:

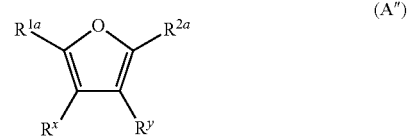

(A'')

wherein:
  $R^{1a}$ is —$(CH_2)_{m-1}CH(O)$ or —$(CH_2)_mOH$, wherein:
    m is as defined for formula (I''), provided that when m is 0, $R^{1a}$ is H; and
    Y is halo;
  $R^{2a}$ is —$(CH_2)_{n-1}CH(O)$, —$(CH_2)_nOH$, or —$(CH_2)_nX$, wherein:
    n is as defined for formula (I''); and
    X is halo;
  $R^x$ and $R^y$ are as defined for formula (I''); and
the acidic solid support is a solid support that (i) has more acidic sites than basic sites, and (ii) chemisorbs at least 0.001 g ammonia/g solid support.

189. The method of embodiment 188, wherein:
the compound of formula (I'') is a compound of formula (I'):

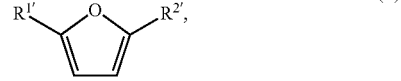

(I')

wherein:
  $R^{1'}$ is $C_m$ alkyl, wherein m is an integer greater than or equal to 0, provided that when m is 0, $R^{1'}$ is H; and
  $R^{2'}$ is $C_n$ alkyl, wherein n is an integer greater than or equal to 1; and
the compound of formula (A'') is a compound of formula (A):

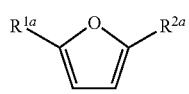

(A)

wherein:
$R^{1a}$ is —$(CH_2)_{m-1}CH(O)$ or —$(CH_2)_mOH$, wherein:
m is as defined for formula (I'), provided that when m is 0, $R^{1a}$ is H; and
Y is halo; and
$R^{2a}$ is —$(CH_2)_{n-1}CH(O)$, —$(CH_2)$—OH, or —$(CH_2)_nX$, wherein:
n is as defined for formula (I'); and
X is halo.

190. The method of embodiment 188 or 189, wherein the acidic solid support comprises zeolite, an acidic metal oxide, or an acidic mixed metal oxide, or any combination thereof.
191. The method of embodiment 188 or 189, wherein the acidic solid support comprises $SiO_2$, ZnO, CdO, $Al_2O_3$, $CeO_2$, $ThO_2$, $TiO_2$, $ZrO_2$, $SnO_2$, PbO, $As_2O_3$, $Bi_2O_3$, $Sb_2O_5$, $V_2O_5$, $Cr_2O_3$, $MoO_3$, $WO_3$, $SiO_2$—$Al_2O_3$, $SiO_2$—$TiO_2$, $SiO_2$—$SnO_2$, $SiO_2$—$ZrO_2$, $SiO_2$—BeO, $SiO_2$—MgO, $SiO_2$—CaO, $SiO_2$—SrO, $SiO_2$—ZnO, $SiO_2$—$Ga_2O_3$, $SiO_2$—$YrO_3$, Si—$O_2$—$La_2O_3$, $SiO_2$—$MoO_3$, $SiO_2$—$WO_3$, $SiO_2$—$V_2O_5$, $SiO_2$—$ThO_2$, $Al_2O_3$—MgO, $Al_2O_3$—ZnO, $Al_2O_3$—CdO, $Al_2O_3$—$B_2O_3$, $Al_2O_3$—$ThO_2$, $Al_2O_3$—$TiO_2$, $Al_2O_3$—$ZrO_2$, $Al_2O_3$—$V_2O_5$, $Al_2O_3$—$MoO_3$, $Al_2O_3$—$WO_3$, $Al_2O_3$—$Cr_2O_3$, $Al_2O_3$—$Mn_2O_3$, $Al_2O_3$—$Fe_2O_3$, $Al_2O_3$—$Co_3O_4$, $Al_2O_3$—NiO, $TiO_2$—CuO, $TiO_2$—MgO, $TiO_2$—ZnO, $TiO_2$—CdO, $TiO_2$—$ZrO_2$, $TiO_2$—$SnO_2$, $TiO_2$—$Bi_2O_3$, $TiO_2$—$Sb_2O_5$, $TiO_2$—$V_2O_5$, $TiO_2$—$Cr_2O_3$, $TiO_2$—$MoO_3$, $TiO_2$—$WO_3$, $TiO_2$—$Mn_2O_3$, $TiO_2$—$Fe_2O_3$, $TiO_2$—$Co_3O_4$, $TiO_2$—NiO, $ZrO_2$—CdO, ZnO—MgO, ZnO—$Fe_2O_3$, $MoO_3$—CoO—$Al_2O_3$, $MoO_3$—NiO—$Al_2O_3$, $TiO_2$—$SiO_2$—MgO, $MoO_3$—$Al_2O_3$—MgO, ZSM5, or Beta zeolite, or any combination thereof.
192. The method of embodiment 191, wherein the acidic solid support is $Al_2O_3$, or $SiO_2$, or any combination thereof.
193. The method of embodiment 188 or 189, wherein the catalyst is:
Pd/$Al_2O_3$;
Pd/ZSM5;
Pd/Beta zeolite;
Pd+Au/$Al_2O_3$;
Pd+Ag/$Al_2O_3$; and
Pd+Cu/$Al_2O_3$,
or any combination thereof.
194. The method of embodiment 193, wherein the catalyst is Pd/$Al_2O_3$.
195. The method of any one of embodiments 188 to 194, wherein the compound of formula (A") is converted to the compound of formula (I") in the presence of (1) hydrogen, (2) the catalyst, (3) the amide reagent, the urea reagent, or a combination thereof, and (4) an aromatic reagent.
196. The method of embodiment 195, wherein the amide reagent, the urea reagent, or a combination thereof, and the aromatic reagent are present in a mass ratio of between 1:10 and 10:1.
197. The method of embodiment 195 or 196, wherein the aromatic reagent comprises at least one mono-aryl compound, at least one di-aryl compound, or at least one tri-aryl compound, or any mixtures thereof.
198. The method of embodiment 195 or 196, wherein the aromatic reagent comprises an alkyl benzene.
199. The method of embodiment 195 or 196, wherein the aromatic reagent comprises a linear alkyl benzene.
200. The method of embodiment 195 or 196, wherein the aromatic reagent comprises toluene, benzene, xylene, or mesitylene, or any combination thereof.
201. The method of embodiment 188 to 200, further comprising isolating the compound of formula (I").
202. The method of embodiment 188 to 201, wherein the converting of the compound of formula (A") to the compound of formula (I") in the presence of (1) hydrogen, (2) the catalyst, and (3) the amide reagent, the urea reagent, or a combination thereof, produces a residual solid-supported metal catalyst, and the method further comprises isolating the residual solid-supported metal catalyst.
203. The method of embodiment 188 to 202, wherein the converting of the compound of formula (A") to the compound of formula (I") in the presence of (1) hydrogen, (2) the catalyst, and (3) the amide reagent, the urea reagent, or a combination thereof, produces a residual solid-supported metal catalyst, and the method further comprises:
regenerating the residual solid-supported metal catalyst to produce a regenerated solid-supported metal catalyst; and
combining the regenerated solid-supported metal catalyst with additional compound of formula (A") in the presence of additional hydrogen and additional amide reagent, urea reagent, or a combination thereof, to produce additional compound of formula (I").
204. A method of producing a compound of formula (I"):

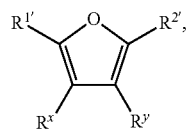

(I")

wherein:
$R^{1'}$ is $C_m$ alkyl, wherein m is an integer greater than or equal to 0, provided that when m is 0, $R^{1'}$ is H;
$R^{2'}$ is $C_n$ alkyl, wherein n is an integer greater than or equal to 1; and
$R^x$ and $R^y$ are independently H or alkyl,
the method comprising converting a compound of formula (A") to the compound of formula (I") in the presence of (1) hydrogen, (2) a catalyst comprising a metal component and a solid support, and (3) an amide reagent, a urea reagent, or a combination thereof, under acidic conditions,
wherein:
the compound of formula (A") is:

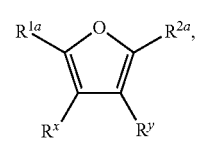

(A")

wherein:
$R^{1a}$ is —$(CH_2)_{m-1}CH(O)$ or —$(CH_2)_mOH$, wherein:
m is as defined for formula (I"), provided that when m is 0, $R^{1a}$ is H; and
Y is halo;
$R^{2a}$ is —$(CH_2)_{n-1}CH(O)$, —$(CH_2)_nOH$, or —$(CH_2)_nX$, wherein:
n is as defined for formula (I"); and
X is halo; and
$R^x$ and $R^y$ are as defined for formula (I").

205. The method of embodiment 204, wherein:
the compound of formula (I") is a compound of formula (I'):

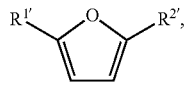 (I')

wherein:
R$^{1'}$ is C$_m$ alkyl, wherein m is an integer greater than or equal to 0, provided that when m is 0, R$^{1'}$ is H; and
R$^{2'}$ is C$_n$ alkyl, wherein n is an integer greater than or equal to 1; and
the compound of formula (A") is a compound of formula (A):

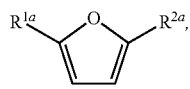 (A)

wherein:
R$^{1a}$ is —(CH$_2$)$_{m-1}$CH(O) or —(CH$_2$)$_m$OH, wherein:
m is as defined for formula (I'), provided that when m is 0, R$^{1a}$ is H; and
Y is halo; and
R$^{2a}$ is —(CH$_2$)$_{n-1}$CH(O), —(CH$_2$)$_n$OH, or —(CH$_2$)$_n$X, wherein:
n is as defined for formula (I'); and
X is halo.

206. The method of embodiment 204 or 205, wherein the solid support is an acidic support that (i) has more acidic sites than basic sites, and (ii) chemisorbs at least 0.001 g ammonia/g solid support.

207. The method of embodiment 206, wherein the acidic solid support comprises zeolite, an acidic metal oxide, or an acidic mixed metal oxide, or any combination thereof.

208. The method of embodiment 206, wherein the acidic solid support comprises SiO$_2$, ZnO, CdO, Al$_2$O$_3$, CeO$_2$, ThO$_2$, TiO$_2$, ZrO$_2$, SnO$_2$, PbO, As$_2$O$_3$, Bi$_2$O$_3$, Sb$_2$O$_5$, V$_2$O$_5$, Cr$_2$O$_3$, MoO$_3$, WO$_3$, SiO$_2$—Al$_2$O$_3$, SiO$_2$—TiO$_2$, SiO$_2$—SnO$_2$, SiO$_2$—ZrO$_2$, SiO$_2$—BeO, SiO$_2$—MgO, SiO$_2$—CaO, SiO$_2$—SrO, SiO$_2$—ZnO, SiO$_2$—Ga$_2$O$_3$, SiO$_2$—YrO$_3$, Si—O$_2$—La$_2$O$_3$, SiO$_2$—MoO$_3$, SiO$_2$—WO$_3$, SiO$_2$—V$_2$O$_5$, SiO$_2$—ThO$_2$, Al$_2$O$_3$—MgO, Al$_2$O$_3$—ZnO, Al$_2$O$_3$—CdO, Al$_2$O$_3$—B$_2$O$_3$, Al$_2$O$_3$—ThO$_2$, Al$_2$O$_3$—TiO$_2$, Al$_2$O$_3$—ZrO$_2$, Al$_2$O$_3$—V$_2$O$_5$, Al$_2$O$_3$—MoO$_3$, Al$_2$O$_3$—WO$_3$, Al$_2$O$_3$—Cr$_2$O$_3$, Al$_2$O$_3$—Mn$_2$O$_3$, Al$_2$O$_3$—Fe$_2$O$_3$, Al$_2$O$_3$—Co$_3$O$_4$, Al$_2$O$_3$—NiO, TiO$_2$—CuO, TiO$_2$—MgO, TiO$_2$—ZnO, TiO$_2$—CdO, TiO$_2$—ZrO$_2$, TiO$_2$—SnO$_2$, TiO$_2$—Bi$_2$O$_3$, TiO$_2$—Sb$_2$O$_5$, TiO$_2$—V$_2$O$_5$, TiO$_2$—Cr$_2$O$_3$, TiO$_2$—MoO$_3$, TiO$_2$—WO$_3$, TiO$_2$—Mn$_2$O$_3$, TiO$_2$—Fe$_2$O$_3$, TiO$_2$—Co$_3$O$_4$, TiO$_2$—NiO, ZrO$_2$—CdO, ZnO—MgO, ZnO—Fe$_2$O$_3$, MoO$_3$—CoO—Al$_2$O$_3$, MoO$_3$—NiO—Al$_2$O$_3$, TiO$_2$—SiO$_2$—MgO, MoO$_3$—Al$_2$O$_3$—MgO, ZSM5, or Beta zeolite, or any combination thereof.

209. The method of embodiment 206, wherein the acidic solid support is Al$_2$O$_3$, or SiO$_2$, or any combination thereof.

210. The method of embodiment 204 or 205, wherein the solid support is a neutral support, and wherein the compound of formula (A) is converted to the compound of formula (I') in the presence of (1) hydrogen, (2) the catalyst, (3) an amide reagent, a urea reagent, or a combination thereof, and (4) an acid.

211. The method of embodiment 210, wherein the neutral support comprises carbon.

212. The method of embodiment 204 or 205, wherein the catalyst is:
Pd/Al$_2$O$_3$;
Pd/C;
Pd+Pt/MgO;
Pd+Au/MgO;
Pd/MgO;
Pd/ZSM5;
Pd/Beta zeolite;
Pd+Au+K/C;
Pd+Ag/C;
Pd+Pt/C;
Pt+Cu/C;
Pt+Au/C;
Pt+Ag/C; or
Pd+Au/C; or
or any combination thereof.

213. The method of embodiment 212, wherein the catalyst is Pd/Al$_2$O$_3$ or Pd/C.

214. The method of any one of embodiments 210 to 213, wherein the compound of formula (A") is converted to the compound of formula (I") in the presence of (1) hydrogen, (2) the catalyst, (3) the amide reagent, the urea reagent, or a combination thereof, (4) the acid, and (5) an aromatic reagent.

215. The method of embodiment 214, wherein the amide reagent, the urea reagent, or a combination thereof, and the aromatic reagent are present in a mass ratio of between 1:10 and 10:1.

216. The method of embodiment 214 or 215, wherein the aromatic reagent comprises at least one mono-aryl compound, at least one di-aryl compound, or at least one tri-aryl compound, or any mixtures thereof.

217. The method of embodiment 214 or 215, wherein the aromatic reagent comprises an alkyl benzene.

218. The method of embodiment 214 or 215, wherein the aromatic reagent comprises a linear alkyl benzene.

219. The method of embodiment 214 or 215, wherein the aromatic reagent comprises toluene, benzene, xylene, or mesitylene, or any combination thereof.

220. The method of any one of embodiments 210 to 219, wherein the acid is:
(i) generated in situ;
(ii) a Bronsted acid;
(iii) H—X or H—Y, wherein X and Y are as defined for formula (A) above; or
(iv) hydrochloric acid or sulfonic acid.

221. The method of embodiment 204 to 220, further comprising isolating the compound of formula (I").

222. The method of embodiment 204 to 221, wherein the converting of the compound of formula (A") to the compound of formula (I") in the presence of (1) hydrogen, (2) the catalyst, and (3) the amide reagent, the urea reagent, or a combination thereof, under acidic conditions, produces a residual solid-supported metal catalyst, and the method further comprises isolating the residual solid-supported metal catalyst.

223. The method of embodiment 204 to 222, wherein the converting of the compound of formula (A") to the compound of formula (I") in the presence of (1) hydrogen, (2) the catalyst, and (3) the amide reagent, the urea reagent, or a combination thereof, under acidic conditions, produces a residual solid-supported metal catalyst, and the method further comprises:

regenerating the residual solid-supported metal catalyst to produce a regenerated solid-supported metal catalyst; and combining the regenerated solid-supported metal catalyst with additional compound of formula (A″) in the presence of additional hydrogen and additional amide reagent, urea reagent, or a combination thereof, to produce additional compound of formula (I″).

224. A method of producing a compound of formula (I″):

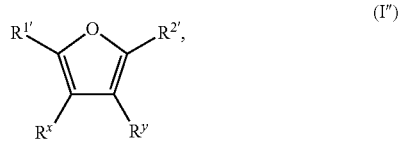
(I″)

wherein:
$R^{1'}$ is $C_m$ alkyl, wherein m is an integer greater than or equal to 0, provided that when m is 0, $R^{1'}$ is H;
$R^{2'}$ is $C_n$ alkyl, wherein n is an integer greater than or equal to 1; and
$R^x$ and $R^y$ are independently H or alkyl,
the method comprising converting a compound of formula (A″) to the compound of formula (I″) in the presence of (1) hydrogen, (2) a catalyst comprising a metal component and a solid support, (3) an amide reagent, a urea reagent, or a combination thereof, and (4) an acid,
wherein:
the compound of formula (A″) is:

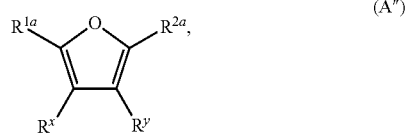
(A″)

wherein:
$R^{1a}$ is $-(CH_2)_{m-1}CH(O)$ or $-(CH_2)_mOH$, wherein:
m is as defined for formula (I″), provided that when m is 0, $R^{1a}$ is H; and
Y is halo;
$R^{2a}$ is $-(CH_2)_{n-1}CH(O)$, $-(CH_2)_nOH$, or $-(CH_2)_nX$, wherein:
n is as defined for formula (I″); and
X is halo; and
$R^x$ and $R^y$ are as defined for formula (I″).

225. The method of embodiment 224, wherein:
the compound of formula (I″) is a compound of formula (I′):

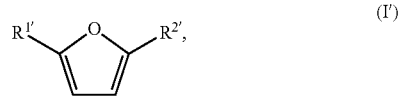
(I′)

wherein:
$R^{1'}$ is $C_m$ alkyl, wherein m is an integer greater than or equal to 0, provided that when m is 0, $R^{1'}$ is H; and
$R^{2'}$ is $C_n$ alkyl, wherein n is an integer greater than or equal to 1; and
the compound of formula (A″) is a compound of formula (A):

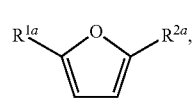
(A)

wherein:
$R^{1a}$ is $-(CH_2)_{m-1}CH(O)$ or $-(CH_2)_mOH$, wherein:
m is as defined for formula (I′), provided that when m is 0, $R^{1a}$ is H; and
Y is halo; and
$R^{2a}$ is $-(CH_2)_{n-1}CH(O)$, $-(CH_2)_nOH$, or $-(CH_2)_nX$, wherein:
n is as defined for formula (I′); and
X is halo.

226. The method of embodiment 224 or 225, wherein the solid support is an acidic support that (i) has more acidic sites than basic sites, and (ii) chemisorbs at least 0.001 g ammonia/g solid support.

227. The method of embodiment 226, wherein the acidic solid support comprises zeolite, an acidic metal oxide, or an acidic mixed metal oxide, or any combination thereof.

228. The method of embodiment 226, wherein the acidic solid support comprises $SiO_2$, ZnO, CdO, $Al_2O_3$, $CeO_2$, $ThO_2$, $TiO_2$, $ZrO_2$, $SnO_2$, PbO, $As_2O_3$, $Bi_2O_3$, $Sb_2O_5$, $V_2O_5$, $Cr_2O_3$, $MoO_3$, $WO_3$, $SiO_2$—$Al_2O_3$, $SiO_2$—$TiO_2$, $SiO_2$—$SnO_2$, $SiO_2$—$ZrO_2$, $SiO_2$—BeO, $SiO_2$—MgO, $SiO_2$—CaO, $SiO_2$—SrO, $SiO_2$—ZnO, $SiO_2$—$Ga_2O_3$, $SiO_2$—$YrO_3$, Si—$O_2$—$La_2O_3$, $SiO_2$—$MoO_3$, $SiO_2$—$WO_3$, $SiO_2$—$V_2O_5$, $SiO_2$—$ThO_2$, $Al_2O_3$—MgO, $Al_2O_3$—ZnO, $Al_2O_3$—CdO, $Al_2O_3$—$B_2O_3$, $Al_2O_3$—$ThO_2$, $Al_2O_3$—$TiO_2$, $Al_2O_3$—$ZrO_2$, $Al_2O_3$—$V_2O_5$, $Al_2O_3$—$MoO_3$, $Al_2O_3$—$WO_3$, $Al_2O_3$—$Cr_2O_3$, $Al_2O_3$—$Mn_2O_3$, $Al_2O_3$—$Fe_2O_3$, $Al_2O_3$—$Co_3O_4$, $Al_2O_3$—NiO, $TiO_2$—CuO, $TiO_2$—MgO, $TiO_2$—ZnO, $TiO_2$—CdO, $TiO_2$—$ZrO_2$, $TiO_2$—$SnO_2$, $TiO_2$—$Bi_2O_3$, $TiO_2$—$Sb_2O_5$, $TiO_2$—$V_2O_5$, $TiO_2$—$Cr_2O_3$, $TiO_2$—$MoO_3$, $TiO_2$—$WO_3$, $TiO_2$—$Mn_2O_3$, $TiO_2$—$Fe_2O_3$, $TiO_2$—$Co_3O_4$, $TiO_2$—NiO, $ZrO_2$—CdO, ZnO—MgO, ZnO—$Fe_2O_3$, $MoO_3$—CoO—$Al_2O_3$, $MoO_3$—NiO—$Al_2O_3$, $TiO_2$—$SiO_2$—MgO, $MoO_3$—$Al_2O_3$—MgO, ZSM5, or Beta zeolite, or any combination thereof.

229. The method of embodiment 228, wherein the acidic solid support is $Al_2O_3$, or $SiO_2$, or any combination thereof.

230. The method of embodiment 224 or 225, wherein the solid support is a neutral support.

231. The method of embodiment 229, wherein the neutral support comprises carbon.

232. The method of any one of embodiments 224 to 231, wherein the acid is:
(i) generated in situ;
(ii) a Bronsted acid;
(iii) H—X or H—Y, wherein X and Y are as defined for formula (A) above; or
(iv) hydrochloric acid or sulfonic acid.

233. The method of any one of embodiments 224 to 232, wherein the compound of formula (A″) is converted to the compound of formula (I″) in the presence of (1) hydrogen, (2) the catalyst, (3) the amide reagent, the urea reagent, or a combination thereof, (4) the acid, and (5) an aromatic reagent.

234. The method of embodiment 233, wherein the amide reagent, the urea reagent, or a combination thereof, and the aromatic reagent are present in a mass ratio of between 1:10 and 10:1.

235. The method of embodiment 224 to 234, further comprising isolating the compound of formula (I″).

236. The method of embodiment 224 to 235, wherein the converting of the compound of formula (A") to the compound of formula (I") in the presence of (1) hydrogen, (2) the catalyst, (3) the amide reagent, a urea reagent, or a combination thereof, and (4) the acid produces a residual solid-supported metal catalyst, and the method further comprises isolating the residual solid-supported metal catalyst.

237. The method of embodiment 224 to 236, wherein the converting of the compound of formula (A") to the compound of formula (I") in the presence of (1) hydrogen, (2) the catalyst, (3) the amide reagent, a urea reagent, or a combination thereof, and (4) the acid produces a residual solid-supported metal catalyst, and the method further comprises:

regenerating the residual solid-supported metal catalyst to produce a regenerated solid-supported metal catalyst; and combining the regenerated solid-supported metal catalyst with additional compound of formula (A") in the presence of additional hydrogen, additional amide reagent, urea reagent, or a combination thereof, and additional acid to produce additional compound of formula (I").

238. The method of any one of embodiments 178 to 237, wherein the compound of formula (I") is produced at a yield of at least 25%; and a selectivity of at least 25%.

239. The method of any one of embodiments 178 to 238, wherein the compound of formula (A") and the hydrogen are present in a mass ratio between 1:2.9 and 1:3.8.

240. The method of any one of embodiments 178 to 239, wherein the compound of formula (A") is converted to the compound of formula (I') at a temperature of less than 50° C.

241. The method of any one of embodiments 178 to 240, wherein the metal component is impregnated, deposited, precipitated, or any combination thereof, onto the solid support.

242. The method of any one of embodiments 178 to 241, wherein the metal component comprises:
(i) at least one metal;
(ii) at least two metals;
(iii) one metal, two metals, or three metals;
(iv) at least one Group 10 metal; or
(v) at least one Group 10 metal, and at least one Group 11 metal.

243. The method of any one of embodiments 178 to 242, wherein the metal component comprises:
(i) palladium, or platinum, or a combination thereof; and
(ii) gold, silver, or copper, or any combination thereof.

244. The method of any one of embodiments 178 to 243, wherein the metal component comprises palladium and at least one additional metal, wherein the palladium and the least one additional metal are present in the catalyst in a weight ratio of 0.1 to 20.

245. The method of any one of embodiments 178 to 244, wherein the metal component comprises:
(i) palladium;
(ii) palladium and platinum;
(iii) palladium and gold;
(iv) palladium and copper;
(v) palladium and silver;
(vi) platinum;
(vii) platinum and gold;
(viii) platinum and copper; or
(ix) platinum and silver.

246. The method of any one of embodiments 178 to 245, wherein the catalyst has a total metal loading between 0.1% to 20% by weight.

247. The method of any one of embodiments 178 to 246, wherein the amide reagent is a reagent of formula (i):

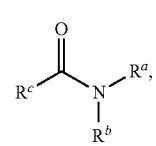

wherein:
each $R^a$, $R^b$ and $R^c$ is independently H, aliphatic, aryl, or heteroaryl; or
$R^a$ and $R^b$ are taken together with the nitrogen atoms to which they are connected to form a cyclic moiety having at least 3 ring atoms.

248. The method of embodiment 247, wherein the reagent of formula (i) is other than N,N-dimethylformamide and N,N-dimethylacetamide.

249. The method of embodiment 247, wherein when $R^c$ is H or methyl, then one of $R^a$ and $R^b$ is other than methyl.

250. The method of any one of embodiments 178 to 246, wherein the urea reagent is a reagent of formula (ii):

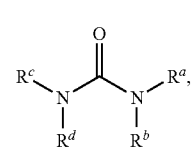

wherein:
(A) each $R^a$, $R^b$, $R^c$ and $R^d$ is independently H, aliphatic, aryl or heteroaryl; or
(B) $R^a$ and $R^b$ are taken together with the nitrogen atoms to which they are connected to form a cyclic moiety having at least 3 ring atoms; and each $R^c$ and $R^d$ is independently H, aliphatic, aryl or heteroaryl; or
(C) each $R^a$ and $R^b$ is independently H, aliphatic, aryl or heteroaryl; and $R^c$ and $R^d$ are taken together with the nitrogen atoms to which they are connected to form a cyclic moiety having at least 3 ring atoms; or
(D) $R^a$ and $R^b$ are taken together with the nitrogen atoms to which they are connected to form a cyclic moiety having at least 3 ring atoms; and $R^c$ and $R^d$ are taken together with the nitrogen atoms to which they are connected to form a cyclic moiety having at least 3 ring atoms; or
(E) each $R^a$ and $R^c$ is independently H, aliphatic, aryl or heteroaryl; and $R^b$ and $R^d$ are taken together with the nitrogen atoms to which they are connected to form a cyclic moiety having at least 5 ring atoms; or
(F) each $R^b$ and $R^d$ is independently H, aliphatic, aryl or heteroaryl; and $R^a$ and $R^c$ are taken together with the nitrogen atoms to which they are connected to form a cyclic moiety having at least 5 ring atoms.

251. The method of any one of embodiments 178 to 246, wherein the urea reagent is a cyclic urea reagent.

252. The method of any one of embodiments 178 to 251, wherein the urea reagent is a reagent of formula (iii):

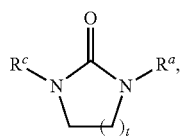

(iii)

wherein:

each $R^a$ and $R^c$ is independently H, aliphatic, aryl or heteroaryl; and t is an integer greater than or equal to 0.

253. The method of embodiment 252, wherein t is an integer greater than or equal to 1.

254. The method of embodiment 253, wherein t is 1 or 2.

255. The method of any one of embodiments 178 to 246, wherein the amide or urea reagent is selected from the group consisting of

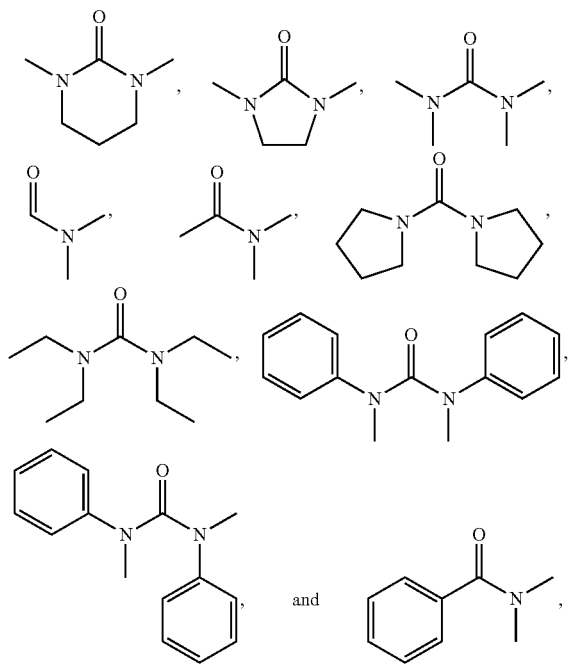

or any combinations thereof.

256. The method of any one of embodiments 178 to 246, wherein the urea reagent is

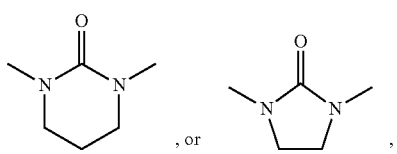

or a combination thereof.

257. The method of any one of embodiments 178 to 256, wherein $R^{1a}$ is $C_m$ alkyl.

258. The method of any one of embodiments 178 to 256, wherein $R^{1a}$ is $—(CH_2)_mY$.

259. The method of any one of embodiments 178 to 256, wherein $R^{1a}$ is $—(CH_2)_{m-1}CH(O)$.

260. The method of any one of embodiments 178 to 256, wherein $R^{1a}$ is $—(CH_2)_mOH$.

261. The method of any one of embodiments 178 to 260, wherein $R^{2a}$ is $—(CH_2)_{n-1}CH(O)$.

262. The method of any one of embodiments 178 to 260, wherein $R^{2a}$ is $—(CH_2)_nOH$.

263. The method of any one of embodiments 178 to 260, wherein $R^{2a}$ is $—(CH_2)_nX$.

264. The method of any one of embodiments 178 to 263, wherein m is 0.

265. The method of any one of embodiments 178 to 263, wherein m is 1.

266. The method of any one of embodiments 178 to 265, wherein n is 1.

267. A method of producing a compound of formula (J):

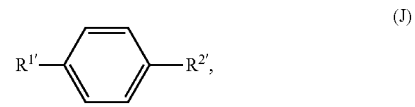

(J)

wherein:

$R^{1'}$ is $C_m$ alkyl, wherein m is an integer greater than or equal to 0, provided that when m is 0, $R^{1'}$ is H; and $R^{2'}$ is $C_n$ alkyl, wherein n is an integer greater than or equal to 1, the method comprising:

combining a compound of formula (I') produced according to the method of any one of embodiments 178 to 266 and ethylene to produce the compound of formula (J).

268. The method of embodiment 267, wherein m is 0.

269. The method of embodiment 267, wherein m is 1.

270. The method of any one of embodiments 267 to 269, wherein n is 1.

271. A composition, comprising:

a compound of formula (A"):

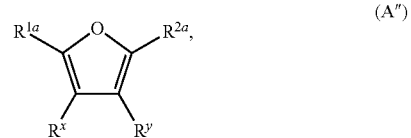

(A")

wherein:

$R^{1a}$ is $C_m$ alkyl, $—(CH_2)_mY$, $—(CH_2)_{m-1}CH(O)$ or $—(CH_2)_mOH$ wherein:

m is as defined for formula (I"), provided that when m is 0, $R^{1a}$ is H; and

Y is halo; and $R^{2a}$ is $—(CH_2)_{n-1}CH(O)$, $—(CH_2)_nOH$, or $—(CH_2)_nX$, wherein:

n is as defined for formula (I"); and

X is halo; and $R^x$ and $R^y$ are independently H or alkyl;

hydrogen;

a solid-supported metal catalyst comprising a metal component and a basic solid support, wherein the basic solid support is a solid support that (i) has more basic sites than acidic sites and (ii) chemisorbs at least 0.001 g carbon dioxide/g solid support; and optionally an amide reagent, a urea reagent, or a combination thereof.

272. The composition of embodiment 271, wherein:

the compound of formula (I") is a compound of formula (I'):

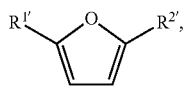

wherein:
R$^{1'}$ is C$_m$ alkyl, wherein m is an integer greater than or equal to 0, provided that when m is 0, R$^{1'}$ is H; and
R$^{2'}$ is C$_n$ alkyl, wherein n is an integer greater than or equal to 1; and
the compound of formula (A") is a compound of formula (A):

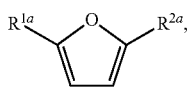

wherein:
R$^{1a}$ is C$_m$ alkyl, —(CH$_2$)$_m$Y, —(CH$_2$)$_{m-1}$CH(O) or —(CH$_2$)$_m$OH wherein:
  m is as defined for formula (I'), provided that when m is 0, R$^{1a}$ is H; and
  Y is halo; and
R$^{2a}$ is —(CH$_2$)$_{n-1}$CH(O), —(CH$_2$)$_n$OH, or —(CH$_2$)$_n$X, wherein:
  n is as defined for formula (I'); and
  X is halo.

273. The composition of embodiment 271 or 272, wherein the basic solid support comprises a basic metal oxide.

274. The composition of embodiment 271 or 272, wherein the basic solid support comprises a solid support modified by an alkali metal or an alkali earth metal.

275. The composition of embodiment 271 or 272, wherein the basic solid support comprises a solid support modified by a base.

276. The composition of embodiment 271 or 272, wherein the basic solid support comprises BeO, MgO, CaO, SrO, BaO, ZnO, Al$_2$O$_3$, Y$_2$O$_3$, La$_2$O$_3$, CeO$_2$, ThO$_2$, TiO$_2$, ZrO$_2$ or SnO$_2$, or any combinations thereof.

277. The composition of embodiment 271 or 272, wherein the catalyst is:
  Pd+Pt/MgO;
  Pd+Au/MgO; or
  Pd/MgO,
or any combination thereof.

278. A composition, comprising:
  a compound of formula (A"):

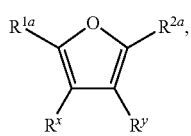

wherein:
R$^{1a}$ is C$_m$ alkyl, —(CH$_2$)$_m$Y, —(CH$_2$)$_{m-1}$CH(O) or —(CH$_2$)$_m$OH wherein:
  m is as defined for formula (I"), provided that when m is 0, R$^{1a}$ is H; and
  Y is halo; and
R$^{2a}$ is —(CH$_2$)$_{n-1}$CH(O), —(CH$_2$)$_n$OH, or —(CH$_2$)$_n$X, wherein:
  n is as defined for formula (I"); and
  X is halo; and
R$^x$ and R$^y$ are independently H or alkyl;
hydrogen;
a catalyst comprising a metal component and an acidic solid support, wherein the acidic solid support is a solid support that (i) has more acidic sites than basic sites, and (ii) chemisorbs at least 0.001 g ammonia/g solid support; and
an amide reagent, a urea reagent, or a combination thereof.

279. The composition of embodiment 278, wherein:
the compound of formula (I") is a compound of formula (I'):

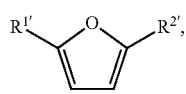

wherein:
R$^{1'}$ is C$_m$ alkyl, wherein m is an integer greater than or equal to 0, provided that when m is 0, R$^{1'}$ is H; and
R$^{2'}$ is C$_n$ alkyl, wherein n is an integer greater than or equal to 1; and
the compound of formula (A") is a compound of formula (A):

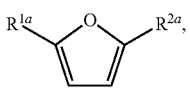

wherein:
R$^{1a}$ is C$_m$ alkyl, —(CH$_2$)$_m$Y, —(CH$_2$)$_{m-1}$CH(O) or —(CH$_2$)$_m$OH wherein:
  m is as defined for formula (I'), provided that when m is 0, R$^{1a}$ is H; and
  Y is halo; and
R$^{2a}$ is —(CH$_2$)$_{n-1}$CH(O), —(CH$_2$)$_n$OH, or —(CH$_2$)$_n$X, wherein:
  n is as defined for formula (I'); and
  X is halo.

280. The composition of embodiment 278 or 279, wherein the acidic solid support comprises zeolite, an acidic metal oxide, or an acidic mixed metal oxide, or any combination thereof.

281. The composition of embodiment 278 or 279, wherein the acidic solid support comprises SiO$_2$, ZnO, CdO, Al$_2$O$_3$, CeO$_2$, ThO$_2$, TiO$_2$, ZrO$_2$, SnO$_2$, PbO, As$_2$O$_3$, Bi$_2$O$_3$, Sb$_2$O$_5$, V$_2$O$_5$, Cr$_2$O$_3$, MoO$_3$, WO$_3$, SiO$_2$—Al$_2$O$_3$, SiO$_2$—TiO$_2$, SiO$_2$—SnO$_2$, SiO$_2$—ZrO$_2$, SiO$_2$—BeO, SiO$_2$—MgO, SiO$_2$—CaO, SiO$_2$—SrO, SiO$_2$—ZnO, SiO$_2$—Ga$_2$O$_3$, SiO$_2$—YrO$_3$, Si—O$_2$—La$_2$O$_3$, SiO$_2$—MoO$_3$, SiO$_2$—WO$_3$, SiO$_2$—V$_2$O$_5$, SiO$_2$—ThO$_2$, Al$_2$O$_3$—MgO, Al$_2$O$_3$—ZnO, Al$_2$O$_3$—CdO, Al$_2$O$_3$—B$_2$O$_3$, Al$_2$O$_3$—ThO$_2$, Al$_2$O$_3$—TiO$_2$, Al$_2$O$_3$—ZrO$_2$, Al$_2$O$_3$—V$_2$O$_5$, Al$_2$O$_3$—MoO$_3$, Al$_2$O$_3$—WO$_3$, Al$_2$O$_3$—Cr$_2$O$_3$, Al$_2$O$_3$—Mn$_2$O$_3$, Al$_2$O$_3$—Fe$_2$O$_3$, Al$_2$O$_3$—Co$_3$O$_4$, Al$_2$O$_3$—NiO, TiO$_2$—CuO, TiO$_2$—MgO, TiO$_2$—ZnO, TiO$_2$—CdO, TiO$_2$—ZrO$_2$, TiO$_2$—SnO$_2$, TiO$_2$—Bi$_2$O$_3$, TiO$_2$—Sb$_2$O$_5$, TiO$_2$—V$_2$O$_5$, TiO$_2$—Cr$_2$O$_3$, TiO$_2$—MoO$_3$, TiO$_2$—WO$_3$, TiO$_2$—Mn$_2$O$_3$, TiO$_2$—Fe$_2$O$_3$, TiO$_2$—Co$_3$O$_4$, TiO$_2$—NiO, ZrO$_2$—CdO, ZnO—MgO, ZnO—Fe$_2$O$_3$, MoO$_3$—CoO—Al$_2$O$_3$, MoO$_3$—NiO—Al$_2$O$_3$, TiO$_2$—SiO$_2$—MgO, MoO$_3$—Al$_2$O$_3$—MgO, ZSM5, or Beta zeolite, or any combination thereof.

282. The composition of embodiment 281, wherein the acidic solid support is Al$_2$O$_3$, or SiO$_2$, or any combination thereof.

283. The composition of embodiment 278 or 279, wherein the catalyst is:
Pd/Al$_2$O$_3$;
Pd/ZSM5;
Pd/Beta zeolite;
Pd+Au/Al$_2$O$_3$;
Pd+Ag/Al$_2$O$_3$; and
Pd+Cu/Al$_2$O$_3$,
or any combination thereof.

284. The composition of embodiment 283, wherein the catalyst is Pd/Al$_2$O$_3$.

285. A composition, comprising:
a compound of formula (A"):

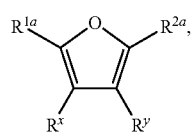

wherein:
$R^{1a}$ is C$_m$ alkyl, —(CH$_2$)$_m$Y, —(CH$_2$)$_{m-1}$CH(O) or —(CH$_2$)$_m$OH wherein:
m is as defined for formula (I"), provided that when m is 0, $R^{1a}$ is H; and
Y is halo; and
$R^{2a}$ is —(CH$_2$)$_{n-1}$CH(O), —(CH$_2$)$_n$OH, or —(CH$_2$)$_n$X, wherein:
n is as defined for formula (I"); and
X is halo; and
$R^x$ and $R^y$ are independently H or alkyl;
hydrogen;
a catalyst comprising a metal component and a solid support;
an amide reagent, a urea reagent, or a combination thereof; and
an acid.

286. The composition of embodiment 285, wherein the solid support is an acidic support that (i) has more acidic sites than basic sites, and (ii) chemisorbs at least 0.001 g ammonia/g solid support.

287. The composition of embodiment 286, wherein the acidic solid support comprises zeolite, an acidic metal oxide, or an acidic mixed metal oxide, or any combination thereof.

288. The composition of embodiment 286, wherein the acidic solid support comprises SiO$_2$, ZnO, CdO, Al$_2$O$_3$, CeO$_2$, ThO$_2$, TiO$_2$, ZrO$_2$, SnO$_2$, PbO, As$_2$O$_3$, Bi$_2$O$_3$, Sb$_2$O$_5$, V$_2$O$_5$, Cr$_2$O$_3$, MoO$_3$, WO$_3$, SiO$_2$—Al$_2$O$_3$, SiO$_2$—TiO$_2$, SiO$_2$—SnO$_2$, SiO$_2$—ZrO$_2$, SiO$_2$—BeO, SiO$_2$—MgO, SiO$_2$—CaO, SiO$_2$—SrO, SiO$_2$—ZnO, SiO$_2$—Ga$_2$O$_3$, SiO$_2$—YrO$_3$, Si—O$_2$—La$_2$O$_3$, SiO$_2$—MoO$_3$, SiO$_2$—WO$_3$, SiO$_2$—V$_2$O$_5$, SiO$_2$—ThO$_2$, Al$_2$O$_3$—MgO, Al$_2$O$_3$—ZnO, Al$_2$O$_3$—CdO, Al$_2$O$_3$—B$_2$O$_3$, Al$_2$O$_3$—ThO$_2$, Al$_2$O$_3$—TiO$_2$, Al$_2$O$_3$—ZrO$_2$, Al$_2$O$_3$—V$_2$O$_5$, Al$_2$O$_3$—MoO$_3$, Al$_2$O$_3$—WO$_3$, Al$_2$O$_3$—Cr$_2$O$_3$, Al$_2$O$_3$—Mn$_2$O$_3$, Al$_2$O$_3$—Fe$_2$O$_3$, Al$_2$O$_3$—Co$_3$O$_4$, Al$_2$O$_3$—NiO, TiO$_2$—CuO, TiO$_2$—MgO, TiO$_2$—ZnO, TiO$_2$—CdO, TiO$_2$—ZrO$_2$, TiO$_2$—SnO$_2$, TiO$_2$—Bi$_2$O$_3$, TiO$_2$—Sb$_2$O$_5$, TiO$_2$—V$_2$O$_5$, TiO$_2$—Cr$_2$O$_3$, TiO$_2$—MoO$_3$, TiO$_2$—WO$_3$, TiO$_2$—Mn$_2$O$_3$, TiO$_2$—Fe$_2$O$_3$, TiO$_2$—Co$_3$O$_4$, TiO$_2$—NiO, ZrO$_2$—CdO, ZnO—MgO, ZnO—Fe$_2$O$_3$, MoO$_3$—CoO—Al$_2$O$_3$, MoO$_3$—NiO—Al$_2$O$_3$, TiO$_2$—SiO$_2$—MgO, MoO$_3$—Al$_2$O$_3$—MgO, ZSM5, or Beta zeolite, or any combination thereof.

289. The composition of embodiment 288, wherein the acidic solid support is Al$_2$O$_3$, or SiO$_2$, or any combination thereof.

290. The composition of embodiment 285, wherein the solid support is a neutral support.

291. The composition of embodiment 290, wherein the neutral support comprises carbon.

292. The composition of embodiment 285, wherein the catalyst is:
Pd/Al$_2$O$_3$;
Pd/C;
Pd+Pt/MgO;
Pd+Au/MgO;
Pd/MgO;
Pd/ZSM5;
Pd/Beta zeolite;
Pd+Au+K/C;
Pd+Ag/C;
Pd+Pt/C;
Pt+Cu/C;
Pt+Au/C;
Pt+Ag/C; or
Pd+Au/C; or
or any combination thereof.

293. The composition of embodiment 292, wherein the catalyst is Pd/Al$_2$O$_3$ or Pd/C.

294. The composition of any one of embodiments 271 to 293, further comprising an aromatic reagent.

295. The composition of embodiment 294, wherein the urea reagent and the aromatic reagent are present in a mass ratio of between 1:10 and 10:1.

296. The composition of any one of embodiments 271 to 295, wherein the metal component is impregnated, deposited, precipitated, or any combination thereof, onto the solid support.

297. The composition of any one of embodiments 271 to 296, wherein the metal component comprises:
(i) at least one metal;
(ii) at least two metals;
(iii) one metal, two metals, or three metals;
(iv) at least one Group 10 metal; or
(v) at least one Group 10 metal, and at least one Group 11 metal.

298. The composition of any one of embodiments 271 to 297, wherein the metal component comprises:
(i) palladium, or platinum, or a combination thereof; and
(ii) gold, silver, or copper, or any combination thereof.

299. The composition of any one of embodiments 271 to 298, wherein the metal component comprises palladium and at least one additional metal, wherein the palladium and the least one additional metal are present in the catalyst in a weight ratio of 0.1 to 20.

300. The composition of any one of embodiments 271 to 299, wherein the metal component comprises:
(i) palladium;
(ii) palladium and platinum;
(iii) palladium and gold;
(iv) palladium and copper;
(v) palladium and silver;
(vi) platinum;
(vii) platinum and gold;
(viii) platinum and copper; or
(ix) platinum and silver.

301. The composition of any one of embodiments 271 to 300, wherein the catalyst has a total metal loading between 0.1% to 20% by weight.

302. The composition of any one of embodiments 271 to 301, wherein the amide reagent is a reagent of formula (i):

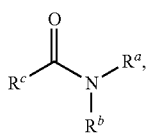
(i)

wherein:
each $R^a$, $R^b$ and $R^c$ is independently H, aliphatic, aryl, or heteroaryl; or
$R^a$ and $R^b$ are taken together with the nitrogen atoms to which they are connected to form a cyclic moiety having at least 3 ring atoms.

303. The composition of embodiment 302, wherein the reagent of formula (i) is other than N,N-dimethylformamide and N,N-dimethylacetamide.

304. The composition of embodiment 302, wherein when $R^c$ is H or methyl, then one of $R^a$ and $R^b$ is other than methyl.

305. The composition of any one of embodiments 271 to 301, wherein the urea reagent is a reagent of formula (ii):

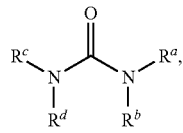
(ii)

wherein:
(A) each $R^a$, $R^b$, $R^c$ and $R^d$ is independently H, aliphatic, aryl or heteroaryl; or
(B) $R^a$ and $R^b$ are taken together with the nitrogen atoms to which they are connected to form a cyclic moiety having at least 3 ring atoms; and each $R^c$ and $R^d$ is independently H, aliphatic, aryl or heteroaryl; or
(C) each $R^a$ and $R^b$ is independently H, aliphatic, aryl or heteroaryl; and $R^c$ and $R^d$ are taken together with the nitrogen atoms to which they are connected to form a cyclic moiety having at least 3 ring atoms; or
(D) $R^a$ and $R^b$ are taken together with the nitrogen atoms to which they are connected to form a cyclic moiety having at least 3 ring atoms; and $R^c$ and $R^d$ are taken together with the nitrogen atoms to which they are connected to form a cyclic moiety having at least 3 ring atoms; or
(E) each $R^a$ and $R^c$ is independently H, aliphatic, aryl or heteroaryl; and $R^b$ and $R^d$ are taken together with the nitrogen atoms to which they are connected to form a cyclic moiety having at least 5 ring atoms; or
(F) each $R^b$ and $R^d$ is independently H, aliphatic, aryl or heteroaryl; and $R^a$ and $R^c$ are taken together with the nitrogen atoms to which they are connected to form a cyclic moiety having at least 5 ring atoms.

306. The composition of any one of embodiments 271 to 301, wherein the urea reagent is a cyclic urea reagent.

307. The composition of any one of embodiments 271 to 301, wherein the urea reagent is a reagent of formula (iii):

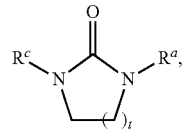
(iii)

wherein:
each $R^a$ and $R^c$ is independently H, aliphatic, aryl or heteroaryl; and
t is an integer greater than or equal to 0.

308. The composition of any one of embodiments 271 to 301, wherein the amide or urea reagent is selected from the group consisting of

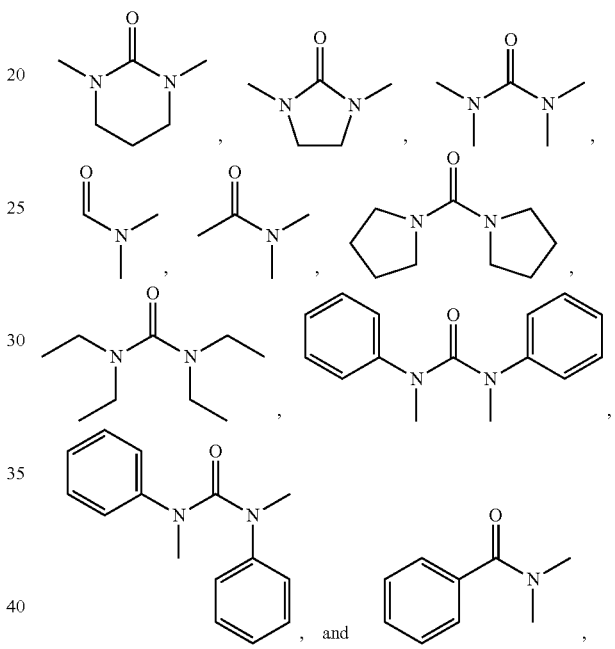
, and or any combinations thereof.

309. The composition of any one of embodiments 271 to 301, wherein the urea reagent is

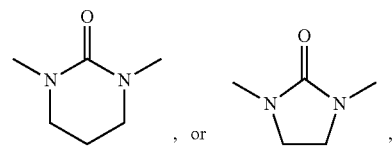
, or or a combination thereof.

310. The composition of any one of embodiments 271 to 309, wherein $R^{1a}$ is $C_m$ alkyl.

311. The composition of any one of embodiments 271 to 309, wherein $R^{1a}$ is $-(CH_2)_m Y$.

312. The composition of any one of embodiments 271 to 309, wherein $R^{1a}$ is $-(CH_2)_{m-1} CH(O)$.

313. The composition of any one of embodiments 271 to 309, wherein $R^{1a}$ is $-(CH_2)_m OH$.

314. The composition of any one of embodiments 271 to 313, wherein $R^{2a}$ is $-(CH_2)_{n-1} CH(O)$.

315. The composition of any one of embodiments 271 to 313, wherein $R^{2a}$ is $-(CH_2)_n OH$.

316. The composition of any one of embodiments 271 to 313, wherein $R^{2a}$ is —$(CH_2)_nX$.
317. The composition of any one of embodiments 271 to 316, wherein m is 0.
318. The composition of any one of embodiments 271 to 316, wherein m is 1.
319. The composition of any one of embodiments 271 to 318, wherein n is 1.
320. A method of producing toluene, comprising:
combining a compound of formula (I') produced according to the method of any one of embodiments 1 to 87, 178 to 270 and ethylene to produce toluene, wherein the compound of formula (I') is 5-methylfuran.

EXAMPLES

The following Examples are merely illustrative and are not meant to limit any aspects of the present disclosure in any way.

Example 1

Synthesis of 2,5-dimethylfuran (DMF) from 5-(chloromethyl)furfural (CMF)

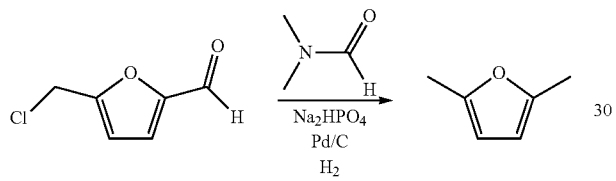

Reaction No. 1:
In a 250 mL Parr container (cooled to room temperature) was added 22.5 mL of N,N-dimethylformamide (DMFD) and Na$_2$HPO$_4$ (0.51 eq, 17.802 mmol, 2.5272 g). To 502 mg of 10% Pd/C was added 1 ml of DMFD and the wet paste was stirred for 1 min with a spatula. The synthesized wet paste was then added to the reaction flask under air. The remaining Pd/C paste in the vial was washed with 1.5 ml of DMFD. The reaction was then preheated to 35° C. (23 min, max T reached 42° C.) under shaking and argon (purge line connected to Argon line). CMF (5 g, 34.587 mmol) was added and the reaction was first stirred 2 min and then charged with H$_2$ up to 50 psi (charged and purged 4 times to 20 psi). The flask was refilled to 50 psi when the pressure was observed to drop to 40 psi. When H$_2$ was charged, a leak observed. H$_2$ was flushed and Argon was added while a screw was tightened. 2 g of Na$_2$HPO$_4$ was added under argon after purging with H$_2$. After about 80 minutes, the reaction mixture was diluted to 100 ml with acetone and an aliquot was taken for analysis by GCMS coupled with FID. Selectivity from CMF to DMF: 79%; Yield from CMF to DMF: 72%.

Reaction No. 2:
In a 250 mL Parr container (cooled to room temperature) was added 5.0058 g (34.628 mmol) of CMF followed by 25 mL of DMFD, Na$_2$HPO$_4$ (0.6 eq, 20.76 mmol, 2.9471 g) and under Argon 502 mg of 10% Pd/C. The reaction flask was then preheated to 35° C. (30 min, max T reached 45° C.) under shaking and Argon (purge line connected to Argon line). The reaction was then charged with H$_2$ up to 50 psi (charged and purged 4 times to 20 psi). The flask was refilled to 50 psi every time the pressure dropped to 40 psi. After about 142 minutes, the reaction mixture was diluted to 100 ml with acetone and an aliquot was taken for analysis by GCMS coupled with FID. Selectivity from CMF to DMF: 80%; Yield from CMF to DMF: 76%.

Example 2

Synthesis of 5-methylfuran-2-carbaldehyde (MF) from 5-(chloromethyl)furfural (CMF)

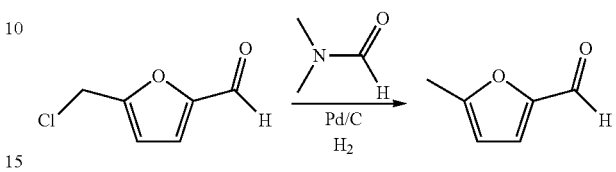

In a 250 mL Parr container (cooled to room temperature) was added 5.0012 g (34.596 mmol) of CMF (97%) followed by 25 mL of DMFD and under Argon 50 mg of 10% Pd/C. The reaction mixture was charged with H$_2$ up to 2 psi (charged and purged 4 times to 20 psi). When a 1 psi drop was observed, the flask was refilled to 2 psi until 65 psi was reached. After about 73 minutes, the reaction mixture was diluted in 100 ml volumetric flask with dichloromethane and an aliquot was taken for analysis by GCMS coupled with FID. Selectivity from MF to CMF: 99%; conversion from MF to CMF: 97%.

Example 3

Synthesis of 2,5-dimethylfuran (DMF) from 5-methylfuran-2-carbaldehyde (MF)

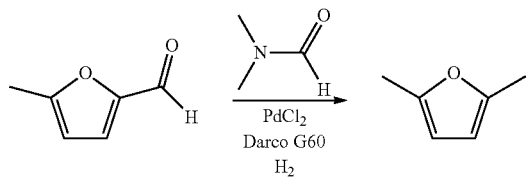

To a 250 ml Parr Shaker, 3.8051 g (34.51 mmol) of MF was added followed by 25 ml of DMFD and under Argon 100 mg of PdCl$_2$ and 500 mg of carbon Darco G60. The reaction was then charged with H$_2$ up to 50 psi (charged and purged 4 times). When a 10 psi drop was observed, the flask was recharged to 50 psi. After about 105 minutes, the reaction mixture was diluted to 100 ml and an aliquot was taken for analysis by GCMS coupled with FID. Selectivity from MF to DMF: 68%; conversion from MF to DMF: 100%; conversion from MF to (5-methylfuran-2-yl)methanol (MFA): 96%.

Example 4

Synthesis of 2,5-dimethylfuran (DMF) from 5-(chloromethyl)furfural (CMF)

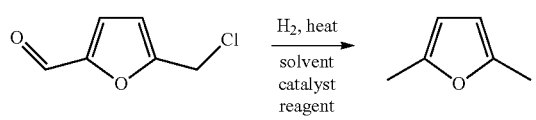

This Example demonstrates the production of 2,5-dimethylfuran (DMF) from 5-(chloromethyl)furfural (CMF) using various catalysts, solvents and other reagents.

To a 250 ml Parr shaker bottle was added CMF (5 g, 34.62 mmol) and 25 ml of Solvent A (as listed in Table 1 below). The CMF was dissolved in a mixture of organic Solvent A and Reagent B (as listed in Table 1 below), by stirring at room temperature for 5-10 minutes. Then, the catalyst (50 mg of Pd on support, as listed in Table 1 below) was either immersed in Reagent B up to the incipient wetness point and transferred to the container, or added directly into the container under argon. The reaction mixture was heated to 30-35° C., and the reaction flask was installed into the Parr Shaker. The flask was charged with hydrogen up to 50 psig (charged and purged 4 times to 20 psig). The flask was shaken to initiate the reaction, and the flask was refilled to 50 psig every time the pressure was observed to drop to about 40 psig. After 180 psig of hydrogen was consumed (2.96 eq of hydrogen), the Parr Shaker was stopped, and hydrogen was flushed out of the flask. The reaction mixture was then transferred into a 100 ml volumetric flask and diluted with acetone. An aliquot of the reaction mixture was taken, and products were quantitatively measured on GC.

TABLE 1

Summary of reactions and results

| Catalyst | CMF loading[a] (g/mL) | Solvent A, weight % | Reagent B, weight % | Reaction time | DMF selectivity (%) | DMF yield (%) |
|---|---|---|---|---|---|---|
| Pd/Al$_2$O$_3$ | 16 | Toluene, 77% | 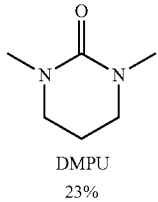<br>DMPU<br>23% | 120 min | 82-84 | 82-84 |
| Pd/Al$_2$O$_3$ | 16 | — | 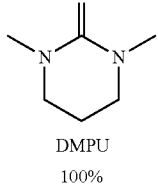<br>DMPU<br>100% | 120 min | 17 | 15 |
| Pd/Al$_2$O$_3$ | 16 | Toluene, 77% | 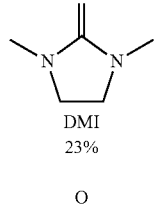<br>DMI<br>23% | 70 min | 63 | 63 |
| Pd/Al$_2$O$_3$ | 16 | Toluene, 78% | 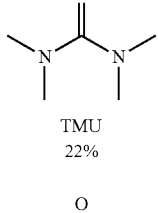<br>TMU<br>22% | 186 min | 59 | 59 |
| Pd/Al$_2$O$_3$ | 16 | — | 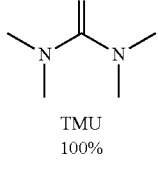<br>TMU<br>100% | 300 min | 61 | 61 |
| Pd/Al$_2$O$_3$ | 16 | — | 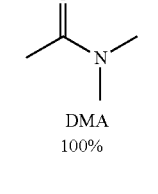<br>DMA<br>100% | 86 min | 36 | 17 |

TABLE 1-continued

Summary of reactions and results

| Catalyst | CMF loading[a] (g/mL) | Solvent A, weight % | Reagent B, weight % | Reaction time | DMF selectivity (%) | DMF yield (%) |
|---|---|---|---|---|---|---|
| Pd/Al$_2$O$_3$ | 16 | — | 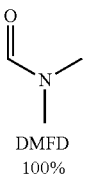 DMFD 100% | 120 min | 83 | 83 |
| Pd/Al$_2$O$_3$ | 26 | — | 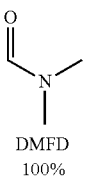 DMFD 100% | 120 min | 81 | 81 |
| Pd/C | 16 | — | 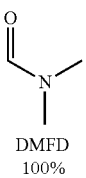 DMFD 100% | 70 min | 82 | 82 |
| Pd/C | 16 | Toluene, 48% | 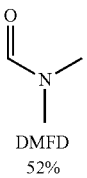 DMFD 52% | 48 min | 82 | 82 |
| Pd/Al$_2$O$_3$ | 16 | Dowtherm ™ G, 78% | 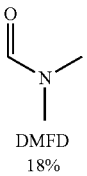 DMFD 18% | 222 min | 64 | 59 |

[a]CMF loading = mass (g) of CMF per total volume (mL) of reaction in solvent mix (Solvent A + Reagent B)

Example 5

Synthesis of Methylfuran from Furfural

This Example demonstrates the synthesis of methylfuran from furfural. To a 250 mL parr hydrogenation flask was added palladium (II) chloride (199.0 mg), Darco G-60 activated carbon (999.0 mg), dimethylpropyleneurea (5 ml), and toluene (15 ml). The flask was then sealed and placed into a Parr hydrogenation apparatus. The headspace was then purged 4× with 10 psig of hydrogen. The flask was then pressurized with hydrogen to 20 psig and the bottle was shaken for 20 minutes. After the metal reduction step, the flask was then depressurized from hydrogen and furfural (3.314 g, 34.492 mmol) was then added to the flask via pipette transfer using an additional 5 ml of toluene. The flask was then re-purged with hydrogen in a similar manner as described above, and the flask was filled with hydrogen to 50 psig, and the reduction was started. The reaction temperature and consumption of hydrogen over time were monitored, and the values are summarized in Table 2 below.

TABLE 2

| Time (min) continuous | Temperature Reaction (° C.) | Total Hydrogen Consumed (mmol) |
|---|---|---|
| 3.7 | 27 to 29 | 6.63 |
| 7.5 | 30 | 12.16 |
| 11.3 | 31 | 17.69 |
| 15.2 | 33 | 23.22 |
| 19.3 | 33 | 29.85 |
| 23.5 | 34 | 35.38 |
| 28.3 | 34 | 40.91 |
| 33.9 | 33 | 46.43 |
| 41.5 | 32 | 51.95 |
| 52.8 | 30 | 57.47 |
| 72.4 | 29 | 62.98 |
| 105.6 | 28 | 68.49 |

After about 106 minutes, the flask was depressurized and removed from the apparatus. The reaction mixture was then diluted to 100 ml in acetone, followed by a 5× dilution in acetone for GCMS analysis.

For the GCMS analysis, 1 uL of sample/standard was injected into an Agilent 6890 GC with FID detection with a 5:1 split ratio at a flow rate of 2.3 mL/min of helium carrier gas and onto the Agilent 5975 MSD with a split ratio of 25:1 at a flow rate of 1.5 mL/min of helium carrier gas. The temperature program started with an initial temperature of 35° C. and ramped up to a final temperature of 240° C. at 60° C./min and was held at 240° C. for 4 minutes. 2-Methylfuran was observed at 1.83 minutes for MS detection and at 1.86 minutes for FID detection. Thus, based on this GCMS analysis, 2-methylfuran was observed to be produced.

Example 6

Synthesis of 2,5-dimethylfuran (DMF) from 5-(chloromethyl)furfural (CMF)

This Example demonstrates the synthesis of DMF from CMF. To a 250 ml Parr hydrogenation bottle was added CMF (5 g; 34 mmol). Dowtherm-G (10 ml) was then added and the CMF was allowed to dissolve with light mixing under ambient conditions for a few minutes until a homogeneous solution was observed. In a separate vial, dimethylformamide (2 ml) was then added to 5% Pd/Alumina (994.3 mg) and the resulting slurry was mixed under ambient conditions for about 30 seconds. The slurry was then pipetted into the reaction flask, and 3 mL of dimethylformamide was used to quantitatively transfer the catalyst. Then, 10 mL of Dowtherm-G was used to wash the residual dimethylformamide from the vial into the reaction flask. The mixture was then heated to about 25° C. before placing the reaction flask into a Parr Shaker. The head space of the flask and the ballast connected to the hydrogen cylinder were then flushed with hydrogen (15 psig of hydrogen in the bottle head space) for about 1 minute. The flask was then purged 4× with 10 psig of hydrogen and filled to 40 psig. The first ballast reading was then taken and the pressure was increased to 50 psig. The consumption of hydrogen over time was monitored, and the values are summarized in Table 3 below.

TABLE 3

| Time (min) continuous | Total Hydrogen Consumed (mmol) |
|---|---|
| 4.6 | 6.702 |
| 9.8 | 13.415 |
| 15.9 | 19.004 |
| 22.0 | 24.602 |
| 28.6 | 30.178 |
| 36.5 | 35.771 |
| 45.8 | 42.464 |
| 56.4 | 48.047 |
| 68.6 | 53.636 |
| 83.0 | 59.231 |
| 100.0 | 64.826 |
| 123.0 | 70.421 |
| 150.0 | 77.132 |
| 175.1 | 83.850 |
| 222 | 88.321 |

The yield of DMF was observed to be about 59%, and the selectivity of DMF was observed to be about 64%. 2-Methylfurfural was also observed to have been produced.

Example 7

Synthesis of 2,5-dimethylfuran (DMF) from 5-(chloromethyl)furfural (CMF) Using Various Catalysts This Example demonstrates the production of 2,5-dimethylfuran (DMF) and 2,5-hexanedione (HD) from 5-(chloromethyl)furfural (CMF) using various catalysts.

Catalyst Preparation

The following is an exemplary procedure to prepare the catalysts used in this Example. A carbon support was first dried at 80° C. in a vacuum oven. After drying, 24.1 grams (about 50 cc) of the carbon support was placed on a watch glass. An aqueous solution, consisting of 0.837 g of palladium chloride and 1.33 grams of hexachloroplatinic acid in 29.5 grams of water, was used then slowly added to the dried support. This impregnated support was dried overnight. The dried material was placed in a one inch diameter tube, the tube was placed in a vertical tube furnace and then purged with nitrogen and finally reduced in flowing hydrogen (95% $H_2$+5% $N_2$), at a flow rate of about 120 cc/minute. Reduction was accomplished by heating the catalyst from room temperature to 220° C. at 10° C./minute and then holding at 220° C. for two hours in the hydrogen flow. After the reduction was complete, the sample was cooled to room temperature, purged with nitrogen, and then placed in a sample container. The final nominal composition of the catalyst prepared according to this procedure was 2.0% Pd+2.0% Pt/Carbon.

Hydrogenation of CMF

The following is an exemplary procedure to hydrogenate CMF to produce DMF and/or HD. A hastelloy reactor was loaded with about 17 cc of catalyst. The reactor was sealed and, after purging with nitrogen, a flow of hydrogen was started through the bed. During a run, the hydrogen flow rate was about 150 cc/minute. Once the reactor reached temperature, about 55° C., a flow of solvent (as described in Tables 4a, 4b and 4c below) was run through the catalyst bed with about 40 cc of solvent. During this process, the pressure was adjusted to about 50 psig. This startup sequence took place over about 60 minutes. Once the catalyst bed was fully saturated with solvent, at temperature, a flow of 25 wt % CMF in solvent was started. The initial flow rate was 0.25 ml/min. The reaction product was sampled periodically with care taken to trap (at 0° C.) any effluent that was entrained in the vapor stream leaving the reactor. Product analysis was done via GC using a dodecane standard that was part of the feed stream.

The various catalysts tested are summarized in the tables below, along with data about conversion into DMF, HD and other products. As used in the tables below:

"CMF" refers to 5-(chloromethyl)furfural;
"DMF" refers to 2,5-dimethylfuran;
"lights" refers to any compounds that elute before DMF in the GC analysis;
"HD" refers to 2,5-hexanedione;
"MF" refers to 5-methylfurfural (or 5-methylfuran-2-carbaldehyde);
"MF-OH" refers to (5-methylfuran-2-yl)methanol;
"heavies" refers to any compounds that elute after the dodecane standard used in the GC analysis;
"DMFD" refers to N,N-dimethylformamide.

TABLE 4a

Experiments performed with toluene as solvent

| Catalyst | Liq Flow (ml/hr) | % CMF Conversion | Selectivity | | | | | |
|---|---|---|---|---|---|---|---|---|
| | | | lights | DMF | HD | MF | MF-OH | heavies |
| 2% Pd + 2% Ag/C | 15 | 36 | 0 | 1 | 0 | 97 | 1 | 1 |
| 3% Pt + 1% Ag/C | 15 | 54 | 0 | 2 | 4 | 90 | 1 | 3 |
| 3% Pd + 1% Au/C | 15 | 82 | 0 | 3 | 14 | 75 | 1 | 8 |
| 3% Au + 2% Cu/C | 15 | 1 | 0 | 0 | 0 | 100 | 0 | 0 |
| 2% Pd + 2% Pt/C | 15 | 97 | 8 | 14 | 32 | 11 | 1 | 32 |
| 3% Pd + 0.5% Au/C | 15 | 97 | 1 | 15 | 30 | 24 | 1 | 25 |
| 3% Pd + 1% Ag/C | 15 | 80 | 0 | 5 | 4 | 88 | 1 | 2 |
| 4% Pt + 0.5% Cu/C | 15 | 41 | 0 | 1 | 4 | 54 | 2 | 35 |
| 3% Pd + 0.5% Au + 0.3% K/C | 15 | 70 | 0 | 2 | 6 | 63 | 0.3 | 20 |
| 3% Pd + 0.5% Au + 0.6% K/C | 15 | 48 | 0 | 3 | 8 | 47 | 1 | 35 |
| 4.0% Pd/C Cl free | 15 | 64 | 0.1 | 3 | 6 | 23 | 0.6 | 40 |

TABLE 4b

Experiments performed with toluene as solvent

| Catalyst | Liq Flow (ml/hr) | % CMF Conversion | Selectivity | | | | | |
|---|---|---|---|---|---|---|---|---|
| | | | lights | DMF | HD | MF | MF-OH | heavies |
| 4% Pd/MgO | 15 | 20 | 0.1 | 11 | 0 | 75 | 1 | 1 |
| 4% Pd/ZSM5 | 15 | 68 | 0.2 | 8 | 3 | 21 | 3 | 50 |
| 3% Pd + 0.5% Au/MgO | 15 | 40 | 0 | 8 | 0 | 77 | 6 | 0 |
| 3% Pd + 0.5% Au/MgO | 15 | 49 | 0 | 9 | 0.7 | 75 | 3 | 1 |
| 2.5% Pd + 1.5% Pt/MgO | 15 | 35 | 0 | 7 | 0.1 | 70 | 6 | 0 |
| 3.5% Pd + 0.3% Au/MgAl2O4 | 15 | 61 | 0.2 | 7 | 0.8 | 27 | 9 | 40 |
| 3.5% Pd + 0.3% Au/CaO | 15 | 73 | 0 | 19 | 1 | 47 | 4 | 20 |
| 3.5% Pd + 0.2% Au/MgO | 15 | 97 | 0.3 | 14 | 4 | 14 | 3 | 60 |
| 2.0% Pd + 0.4% Au/MgO | 15 | 43 | 0 | 4 | 2 | 83 | 2 | 0 |
| 2.0% Pd + 0.4% Au/MgO | 15 | 44 | 0 | 7 | 4 | 78 | 4 | 0 |
| 2.0% Pd + 0.4% Au/MgO | 15 | 64 | 0 | 18 | 2 | 64 | 6 | 3 |

TABLE 4c

Experiments performed with DMFD as solvent

| Catalyst | Liq Flow (ml/hr) | % CMF Conversion | Selectivity | | | | | |
|---|---|---|---|---|---|---|---|---|
| | | | lights | DMF | HD | MF | MF-OH | heavies |
| 3% Pd + 1% Au/C | 15 | 100 | 10 | 72 | 1 | 7 | 1 | 9 |
| 3% Pt + 1% Ag/C | 15 | 99.6 | 2 | 1 | 0.2 | 93 | 0.2 | 3 |

Example 8

Synthesis of 2,5-dimethylfuran (DMF) from 5-(chloromethyl)furfural (CMF) and 5-methylfurfural (MF)

This Example demonstrates the production of 2,5-dimethylfuran (DMF) and other products from 5-(chloromethyl)furfural (CMF) or 5-methylfurfural (MF) using various catalysts and reagents. The catalyst preparation and hydrogenation of CMF were performed in accordance with the procedures set forth in Example 7 above. The catalysts (including preparation details such as catalyst precursor and solvent), solvent, amide/urea reagent (as applicable), and feed used in this Example and the resulting product distribution are summarized in Table 5 below.

As used in the table below:

"Aq" refers to aqueous;

"Non" refers to non-aqueous;

"CMF" refers to 5-(chloromethyl)furfural;

"DMF" refers to 2,5-dimethylfuran;

"MF" refers to 5-methylfurfural (or 5-methylfuran-2-carbaldehyde);

"OverHyd" refers to over hydrogenation, and includes products in which the furan ring has been hydrogenated. Examples of such products include dimethyl tetrahydrofuran;

"Useable" refers to methyfurfural, methylfurfural alcohol, and dimethyl furan;

"GC Heavies" refers to any compounds that elute after the dodecane standard used in the GC analysis;

"Other Heavies" refers to any remaining compounds that have low solubility in the product stream; and "DMFD" refers to N,N-dimethylformamide.

TABLE 5

| No | Cat. | Cat. Prep. Precursor/ Solvent | Cmpd of Formula (A) | Amide/Urea Reag. | % Conv | DMF | MF | Over Hyd | Useable | GC Heavies | Other Heavies |
|---|---|---|---|---|---|---|---|---|---|---|---|
| 1 | 3.0% Pd + 1.0% Au/SiO2 | Chlorides/Aq | CMF | | 78 | 2 | 11 | 0.7 | 18 | 14 | 65 |
| 2 | 3% Pd + 0.1% Au/MgO | Acetates/Non | CMF | | 44 | 4 | 72 | 0 | 76 | 2 | 10 |
| 3 | 3% Pd + 1% Co/Carbon | Nitrates/Aq | CMF | | 75 | 1 | 40 | 0 | 46 | 6 | 40 |
| 4 | 3% Pd + 1% Fe/Carbon | Nitrates/Aq | CMF | | 48 | 2 | 22 | 0 | 30 | 5 | 45 |
| 5 | 3% Pd + 1% Sn/Carbon | AcAc/CHCl3 | CMF | | 89 | 1 | 65 | | 68 | 4 | 30 |
| 6 | 3% Pd/MgO | AcAc/CHCl3 | CMF | | 20 | 3 | 72 | 0 | 78 | 3 | 15 |
| 7 | 3% Pd/MgO | Diamine Chloride/Aq | CMF | | 98 | 28 | 21 | 0 | 56 | 18 | 20 |
| 8 | 3% Pd/MgO | Disodium Chloride/Aq | CMF | | 95 | 22 | 13 | 0.7 | 42 | 27 | 36 |
| 9 | 3% Pd/MgO | Nitrates/Aq | CMF | | 99 | 36 | 2 | 2 | 42 | 31 | 34 |
| 10 | 2% Pd/ZrO2 | Acetates/Non | CMF | | 99.8 | 1 | 3 | 11 | 8 | 25 | 65 |
| 11 | 3% Pd/MgO | Diamine HCO3/Aq | CMF | | 49 | 8 | 55 | 0.2 | 68 | 1 | 30 |
| 12 | 3% Pd/MgO | Diamine HCO3/Aq | CMF | | 54 | 14 | 70 | 0 | 91 | 3 | 6 |
| 13 | 3% Pd/MgO | Diamine HCO3/Aq | CMF | | 50 | 15 | 48 | 0 | 80 | 4 | 20 |
| 14 | 3% Pd/MgO | Diamine HCO3/Aq | CMF | | 99.9 | 52 | 7 | 0.2 | 62 | 14 | 26 |
| 15 | 2% Pd/SiC | Chlorides/Aq | CMF | | 26 | 7 | 24 | 2 | 38 | 11 | 58 |
| 16 | 2% Pd/MgO via deposit ion-precipitation | Chlorides/Aq | CMF | | 93 | 17 | 27 | 0 | 45 | 12 | 54 |
| 17 | 3% Pd/MgO | Diamine HCO3/Aq | CMF | | 100 | 58 | 1 | 1 | 62 | 34 | 10 |
| 18 | 2.0% Pd + 0.3% Au/MgO | Acetates/Non | CMF | DMFD | 99.9 | reactor plug | | | | | |
| 19 | 3.0% Pd + 1.0% Au/C | Chlorides/Aq | CMF | DMFD | 99.9 | 59 | 25 | 0 | 87 | 12 | 0 |
| 20 | 3.0% Pd + 1.0% Ag/C | Nitrates/Aq | CMF | DMFD | 99.9 | 19 | 74 | 0 | 95 | 2 | 0 |
| 21 | 1.0% Pd + 0.3% Au/C | Chlorides/Aq | CMF | DMFD | 99.9 | 13 | 83 | 0 | 96 | 2 | 0 |
| 22 | 1.1% Pd/Al2O3 | Chlorides/Aq | CMF | DMFD | 99.9 | 63 | 3 | 6 | 68 | 28 | 3 |
| 23 | 1.1% Pd/Al2O3 | Chlorides/Aq | CMF | DMFD | 99.9 | 67 | 1 | 0 | 79 | 30 | 0 |
| 24 | 5.0% Pd/Al2O3 | Chlorides/Aq | CMF | DMFD | 99.9 | 67 | 0.1 | 0 | 71 | 28 | 0 |
| 25 | 3.0% Pd + 1.0% Au/C | Chlorides/Aq | MF | | 51 | 40 | NA | 0 | 42 | 32 | 15 |
| 26 | 3% Pd/Al2O3 | Acetates/Non | MF | | 97 | 6 | NA | 1 | 90 | 5 | 3 |
| 27 | 3% Pd/Al2O3 | Chlorides/Aq | MF | | 82 | 10 | NA | 0.4 | 57 | 40 | 4 |
| 28 | 3% Pd + 1% Au/Al2O3 | Chlorides/Aq | MF | | 99 | 5 | NA | 18 | 65 | 30 | 0 |
| 29 | 3% Pd + 1% Cu/Al2O3 | Chlorides/Aq | MF | | 99.5 | 8 | NA | 8 | 20 | 38 | 41 |
| 30 | 3% Pd/Al2O3 | Acetates/Non | MF | DMFD | 98 | 2 | NA | | | 0 | 0 |
| 31 | 5% Pd/Al2O3 | Chlorides/Aq | MF | DMFD | 98 | 3 | NA | | | 0 | 0 |

Example 9

Synthesis of 2,5-dimethylfuran (DMF) from 5-(chloromethyl)furfural (CMF)

This Example demonstrates the production of 2,5-dimethylfuran (DMF) from 5-(chloromethyl)furfural (CMF) using various catalysts, reagents and reaction temperatures. Reactions 1, 2, 7 and 8 below were performed according to the protocol set forth in Example 4 above. Reactions 3-6 were performed according to the protocol below. The catalysts, CMF loading, aromatic reagent and amount, amine/urea reagent and amount and temperature are set forth in Table 6 below.

Protocol for Reactions 3-6:

In a batch reactor fitted with a cooling jacket, a gas entrainment impeller with baffle, was added the amide or urea reagent and the aromatic reagent, followed by CMF and the catalyst according to Table 6 below under an inert atmosphere (argon). The headspace was purged with hydrogen (charged to 5 psi and purged 10 times). The hydrogen was charged to the reactor to 50 psi, and the hydrogen pressure was maintained at 50 psi by controlled addition of hydrogen through a valve from the bottom of the reactor. The gas entrainment impeller was used to agitate the solution. The temperature of the reaction was maintained at the temperature provided in Table 6 below with the use of the chiller and modulating stirring rate. The reaction was allowed to stir until 3.4 (+/−0.4) moles of hydrogen were consumed. This reaction produced 2,5-dimethylfuran with the selectivities and yields set forth in Table 6 below.

It should be understood that "DMPU" refers to 1,3-dimethyl-3,4,5,6-tetrahydro-2(1H)-pyrimidinone, and "DMFD" refers to "N,N-dimethylformamide".

$R^{2'}$ is $C_n$ alkyl, wherein n is an integer greater than or equal to 1, the method comprising converting a compound of formula (A) to the compound of formula (I') in the presence of (1) hydrogen, (2) a solid-supported metal catalyst comprising a metal component and an acidic solid support, and (3) a urea reagent, wherein:

the compound of formula (A) is:

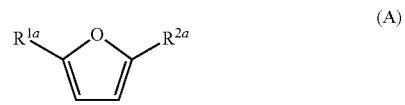

(A)

wherein:

$R^{1a}$ is —$(CH_2)_{m-1}CH(O)$ or —$(CH_2)_m OH$, wherein:
m is as defined for formula (I'), provided that when m is 0, $R^{1a}$ is H; and Y is halo; and $R^{2a}$ is —$(CH_2)_{n-1}CH(O)$, —$(CH_2)_n OH$, or —$(CH_2)_n X$, wherein:

TABLE 6

Summary of reactions and results

| No. | Catalyst | CMF loading[a] | Aromatic Reagent Weight % | Amide/Urea Reagent Weight % | Temperature of Reaction Mixture (° C.) | DMF Selectivity (%) | DMF Yield (%) |
|---|---|---|---|---|---|---|---|
| 1 | Pd/Al$_2$O$_3$ | 20 | 0% | 100% DMPU | Not controlled, exothermic reaction | 17 | 15 |
| 2 | Pd/Al$_2$O$_3$ | 20 | 77% toluene | 23% DMPU | Not controlled, exothermic reaction | 84 | 84 |
| 3 | Pd/Al$_2$O$_3$ | 20 | 77% toluene | 23% DMPU | 35-43 | 92 | 92 |
| 4 | Pd/C | 20 | 11% toluene | 89% DMFD | 35-43 | 93 | 93 |
| 5 | Pd/C | 20 | .1-.5% Toluene | ~99% DMFD | 45-52 | 25 | 25 |
| 6 | Pd/C | 20 | 0.1% Toluene | 99% DMFD | 35-43 | 88 | 88 |
| 7 | Pd/C | 20 | 100% | 0% | Not controlled, exothermic reaction | 50 | 50 |
| 8 | Pd/C | 40 | 0% | 100 | Not controlled, exothermic reaction | 90 | 86 |

[a]CMF loading = mass (g) of CMF per total volume (mL) of reaction in solvent mix (Solvent A + Reagent B)

What is claimed is:

1. A method of producing a compound of formula (I'):

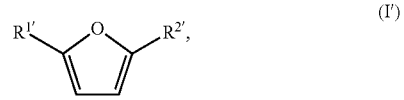

(I')

wherein:

$R^{1'}$ is $C_m$ alkyl, wherein m is an integer greater than or equal to 0, provided that when m is 0, $R^{1'}$ is H; and n is as defined for formula (I'); and X is halo; and the acidic solid support is a solid support that (i) has more acidic sites than basic sites, and (ii) chemisorbs at least 0.001 g ammonia/g solid support.

2. The method of claim 1, wherein the acidic solid support comprises zeolite, an acidic metal oxide, or an acidic mixed metal oxide, or any combination thereof.

3. The method of claim 1, wherein the acidic solid support comprises SiO$_2$, ZnO, CdO, Al$_2$O$_3$, CeO$_2$, ThO$_2$, TiO$_2$, ZrO$_2$, SnO$_2$, PbO, As$_2$O$_3$, Bi$_2$O$_3$, Sb$_2$O$_5$, V$_2$O$_5$, Cr$_2$O$_3$, MoO$_3$, WO$_3$, SiO$_2$—Al$_2$O$_3$, SiO$_2$—TiO$_2$, SiO$_2$—SnO$_2$, SiO$_2$—ZrO$_2$, SiO$_2$—BeO, SiO$_2$—MgO, SiO$_2$—CaO, SiO$_2$—SrO, SiO$_2$—ZnO, SiO$_2$—Ga$_2$O$_3$, SiO$_2$—YrO$_3$, Si—O$_2$—La$_2$O$_3$, SiO$_2$—MoO$_3$, SiO$_2$—WO$_3$, SiO$_2$—V$_2$O$_5$, SiO$_2$—ThO$_2$, Al$_2$O$_3$—MgO, Al$_2$O$_3$—ZnO, Al$_2$O$_3$—CdO, Al$_2$O$_3$—B$_2$O$_3$, Al$_2$O$_3$—ThO$_2$, Al$_2$O$_3$—TiO$_2$, Al$_2$O$_3$—ZrO$_2$, Al$_2$O$_3$—V$_2$O$_5$, Al$_2$O$_3$—MoO$_3$, Al$_2$O$_3$—WO$_3$, Al$_2$O$_3$—Cr$_2$O$_3$, Al$_2$O$_3$—Mn$_2$O$_3$, Al$_2$O$_3$—Fe$_2$O$_3$, Al$_2$O$_3$—Co$_3$O$_4$, Al$_2$O$_3$—NiO, TiO$_2$—CuO, TiO$_2$—MgO, TiO$_2$—ZnO, TiO$_2$—CdO, TiO$_2$—ZrO$_2$, TiO$_2$—SnO$_2$, TiO$_2$—Bi$_2$O$_3$, TiO$_2$—Sb$_2$O$_5$, TiO$_2$—V$_2$O$_5$, TiO$_2$—Cr$_2$O$_3$, TiO$_2$—MoO$_3$, TiO$_2$—WO$_3$, TiO$_2$—Mn$_2$O$_3$, TiO$_2$—Fe$_2$O$_3$, TiO$_2$—Co$_3$O$_4$, TiO$_2$—NiO, ZrO$_2$—CdO, ZnO—MgO, ZnO—Fe$_2$O$_3$, MoO$_3$—CoO—Al$_2$O$_3$, MoO$_3$—NiO—Al$_2$O$_3$, TiO$_2$—SiO$_2$—MgO, MoO$_3$—Al$_2$O$_3$—MgO, ZSM5, or Beta zeolite, or any combination thereof.

4. The method of claim 3, wherein the acidic solid support comprises Al$_2$O$_3$, or SiO$_2$, or any combination thereof.

5. The method of claim 1, wherein the solid-supported metal catalyst is:
Pd/Al$_2$O$_3$;
Pd/ZSM5;
Pd/Beta zeolite;
Pd+Au/Al$_2$O$_3$;
Pd+Ag/Al$_2$O$_3$; and
Pd+Cu/Al$_2$O$_3$,
or any combination thereof.

6. The method of claim 5, wherein the solid-supported metal catalyst is Pd/Al$_2$O$_3$.

7. The method of claim 1, wherein the compound of formula (A) is converted to the compound of formula (I') in the presence of (1) hydrogen, (2) the solid-supported metal catalyst, (3) a urea reagent, and (4) an aromatic reagent.

8. A method of producing a compound of formula (I'):

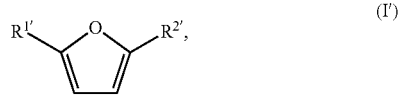

(I')

wherein:
R$^{1'}$ is C$_m$ alkyl, wherein m is an integer greater than or equal to 0, provided that when m is 0, R$^{1'}$ is H; and
R$^{2'}$ is C$_n$ alkyl, wherein n is an integer greater than or equal to 1,
the method comprising converting a compound of formula (A) to the compound of formula (I') in the presence of (1) hydrogen, (2) a solid-supported metal catalyst comprising a metal component and a solid support, and (3) a urea reagent under acidic conditions,
wherein:
the compound of formula (A) is:

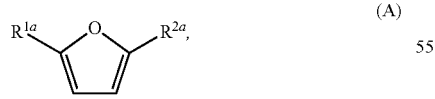

(A)

wherein:
R$^{1a}$ is —(CH$_2$)$_{m-1}$CH(O) or —(CH$_2$)$_m$OH, wherein:
m is as defined for formula (I'), provided that when m is 0, R$^{1a}$ is H; and
Y is halo; and
R$^{2a}$ is —(CH$_2$)$_{n-1}$CH(O), —(CH$_2$)$_n$OH, or —(CH$_2$)$_n$X, wherein:
n is as defined for formula (I'); and
X is halo.

9. The method of claim 8, wherein the compound of formula (A) is converted to the compound of formula (I') in the presence of (1) hydrogen, (2) the solid-supported metal catalyst, (3) the urea reagent, and (4) an aromatic reagent.

10. The method of claim 8, wherein the solid support is an acidic support.

11. The method of claim 8, wherein the solid support is a neutral support, and wherein the compound of formula (A) is converted to the compound of formula (I') in the presence of (1) hydrogen, (2) the solid-supported metal catalyst, (3) the urea reagent, and (4) an acid.

12. The method of claim 11, wherein the neutral support comprises carbon.

13. The method of claim 11, wherein the solid support is a neutral support, and wherein the compound of formula (A) is converted to the compound of formula (I') in the presence of (1) hydrogen, (2) the solid-supported metal catalyst, (3) the urea reagent, (4) the acid, and (5) an aromatic reagent.

14. A method of producing a compound of formula (I'):

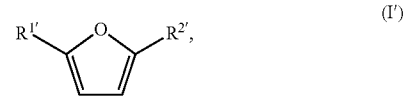

(I')

wherein:
R$^{1'}$ is C$_m$ alkyl, wherein m is an integer greater than or equal to 0, provided that when m is 0, R$^{1'}$ is H; and
R$^{2'}$ is C$_n$ alkyl, wherein n is an integer greater than or equal to 1,
the method comprising converting a compound of formula (A) to the compound of formula (I') in the presence of (1) hydrogen, (2) a solid-supported metal catalyst comprising a metal component and a solid support, (3) a urea reagent, and (4) an acid, wherein:
the compound of formula (A) is:

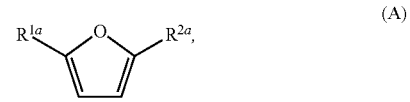

(A)

wherein:
R$^{1a}$ is —(CH$_2$)$_{m-1}$CH(O) or —(CH$_2$)$_m$OH, wherein:
m is as defined for formula (I'), provided that when m is 0, R$^{1a}$ is H; and
Y is halo; and
R$^{2a}$ is —(CH$_2$)$_{n-1}$CH(O), —(CH$_2$)$_n$OH, or —(CH$_2$)$_n$X, wherein:
n is as defined for formula (I'); and
X is halo;
the solid support is:
an acidic support that (i) has more acidic sites than basic sites, and (ii) chemisorbs at least 0.001 g ammonia/g solid support, or
a neutral support.

15. The method of claim 11, wherein the acid is:
(i) generated in situ;
(ii) a Bronsted acid;
(iii) H—X or H—Y, wherein X and Y are as defined for formula (A) above; or
(iv) hydrochloric acid or sulfonic acid.

16. The method of claim 14, wherein the compound of formula (A) is converted to the compound of formula (I') in the presence of (1) hydrogen, (2) the solid-supported metal catalyst, (3) the urea reagent, (4) the acid, and (5) an aromatic reagent.

17. The method of claim 7, wherein the urea reagent and the aromatic reagent are present in a mass ratio of between 1:10 and 10:1.

18. The method of claim 1, wherein the compound of formula (I') is produced at a yield of at least 25%; and a selectivity of at least 25%.

19. The method of claim 1, wherein the compound of formula (A) and the hydrogen are present in a mass ratio between 1:2.9 and 1:3.8.

20. The method of claim 1, wherein the compound of formula (A) is converted to the compound of formula (I') at a temperature of less than 50° C.

21. The method of claim 1, wherein the metal component is impregnated, deposited, precipitated, or any combination thereof, onto the solid support.

22. The method of claim 1, wherein the metal component comprises:
(i) at least one metal;
(ii) at least two metals;
(iii) one metal, two metals, or three metals;
(iv) at least one Group 10 metal; or
(v) at least one Group 10 metal, and at least one Group 11 metal.

23. The method of claim 1, wherein the metal component comprises:
(i) palladium, or platinum, or a combination thereof; and
(ii) gold, silver, or copper, or any combination thereof.

24. The method of claim 1, wherein the metal component comprises palladium and at least one additional metal, wherein the palladium and the least one additional metal are present in the catalyst in a weight ratio of 0.1 to 20.

25. The method of claim 1, wherein the metal component comprises:
(i) palladium;
(ii) palladium and platinum;
(iii) palladium and gold;
(iv) palladium and copper;
(v) palladium and silver;
(vi) platinum;
(vii) platinum and gold;
(viii) platinum and copper; or
(ix) platinum and silver.

26. The method of claim 1, wherein the catalyst has a total metal loading between 0.1% to 20% by weight.

27. The method of claim 1, wherein the urea reagent is a reagent of formula (ii):

$$R^c\underset{R^d}{\overset{}{N}}-\underset{O}{\overset{\|}{C}}-\underset{R^b}{\overset{}{N}}R^a \quad (ii)$$

wherein:
(A) each $R^a$, $R^b$, $R^c$ and $R^d$ is independently H, aliphatic, aryl or heteroaryl; or
(B) $R^a$ and $R^b$ are taken together with the nitrogen atoms to which they are connected to form a cyclic moiety having at least 3 ring atoms; and each $R^c$ and $R^d$ is independently H, aliphatic, aryl or heteroaryl; or
(C) each $R^a$ and $R^b$ is independently H, aliphatic, aryl or heteroaryl; and $R^c$ and $R^d$ are taken together with the nitrogen atoms to which they are connected to form a cyclic moiety having at least 3 ring atoms; or
(D) $R^a$ and $R^b$ are taken together with the nitrogen atoms to which they are connected to form a cyclic moiety having at least 3 ring atoms; and $R^c$ and $R^d$ are taken together with the nitrogen atoms to which they are connected to form a cyclic moiety having at least 3 ring atoms; or
(E) each $R^a$ and $R^c$ is independently H, aliphatic, aryl or heteroaryl; and $R^b$ and $R^d$ are taken together with the nitrogen atoms to which they are connected to form a cyclic moiety having at least 5 ring atoms; or
(F) each $R^b$ and $R^d$ is independently H, aliphatic, aryl or heteroaryl; and $R^a$ and $R^c$ are taken together with the nitrogen atoms to which they are connected to form a cyclic moiety having at least 5 ring atoms.

28. The method of claim 1, wherein the urea reagent is a cyclic urea reagent.

29. The method of claim 1, wherein the urea reagent is a reagent of formula (iii):

$$(iii)$$

wherein:
each $R^a$ and $R^c$ is independently H, aliphatic, aryl or heteroaryl; and
t is an integer greater than or equal to 0.

30. The method of claim 1, wherein the urea reagent is or a combination thereof.

31. The method of claim 7, wherein the aromatic reagent comprises:
(i) at least one mono-aryl compound, at least one di-aryl compound, or at least one tri-aryl compound, or any mixtures thereof;
(ii) an alkyl benzene;
(iii) a linear alkyl benzene; or
(iv) toluene, benzene, xylene, or mesitylene, or any combination thereof.

32. The method of claim 1, wherein:
(i) m is 0 or 1;
(ii) n is 1; or
both (i) and (ii).

33. A method of producing a compound of formula (J):

$$(J)$$

wherein:
$R^{1'}$ is $C_m$ alkyl, wherein m is an integer greater than or equal to 0, provided that when m is 0, $R^{1'}$ is H; and $R^{2'}$ is $C_n$ alkyl, wherein n is an integer greater than or equal to 1, the method comprising:
   combining a compound of formula (I') produced according to the method of claim 1, and ethylene to produce the compound of formula (J).

34. A composition, comprising:
a compound of formula (A):

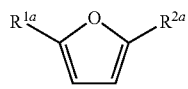
(A)

wherein:
   $R^{1a}$ is —$(CH_2)_{m-1}CH(O)$ or —$(CH_2)_m OH$, wherein:
      m is an integer greater than or equal to 0, provided that when m is 0, $R^{1a}$ is H; and
      Y is halo; and
   $R^{2a}$ is —$(CH_2)_{n-1}CH(O)$, —$(CH_2)_n OH$, or —$(CH_2)_n X$, wherein:
      n is an integer greater than or equal to 1; and
      X is halo;

hydrogen;
a catalyst comprising a metal component and an acidic solid support, wherein the acidic solid support is a solid support that (i) has more acidic sites than basic sites, and (ii) chemisorbs at least 0.001 g ammonia/g solid support; and
a urea reagent.

35. A composition, comprising:
a compound of formula (A):

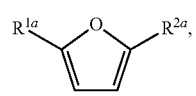
(A)

wherein:
   $R^{1a}$ is —$(CH_2)_{m-1}CH(O)$ or —$(CH_2)_m OH$, wherein:
      m is an integer greater than or equal to 0, provided that when m is 0, $R^{1a}$ is H; and
      Y is halo; and
   $R^{2a}$ is —$(CH_2)_{n-1}CH(O)$, —$(CH_2)_n OH$, or —$(CH_2)_n X$, wherein:
      n is an integer greater than or equal to 1; and
      X is halo;

hydrogen;
a catalyst comprising a metal component and a solid support, wherein the solid support is:
   an acidic solid support (i) having more acidic sites than basic sites, and (ii) chemisorbs at least 0.001 g ammonia/g solid support, or
   a neutral support;
a urea reagent; and
an acid.

36. The composition of claim 34, further comprising an aromatic reagent.

* * * * *